(12) United States Patent
Ono et al.

(10) Patent No.: US 11,435,666 B2
(45) Date of Patent: Sep. 6, 2022

(54) SALT COMPOUND, CHEMICALLY AMPLIFIED RESIST COMPOSITION, AND PATTERNING PROCESS

(71) Applicant: Shin-Etsu Chemical Co., Ltd., Tokyo (JP)

(72) Inventors: Emiko Ono, Joetsu (JP); Masayoshi Sagehashi, Joetsu (JP); Masahiro Fukushima, Joetsu (JP); Yuki Kera, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/669,780

(22) Filed: Oct. 31, 2019

(65) Prior Publication Data
US 2020/0159115 A1 May 21, 2020

(30) Foreign Application Priority Data
Nov. 15, 2018 (JP) ............................. JP2018-214718

(51) Int. Cl.
| | |
|---|---|
| G03F 7/004 | (2006.01) |
| G03F 7/038 | (2006.01) |
| C07D 307/77 | (2006.01) |
| C07C 381/12 | (2006.01) |
| C07C 309/12 | (2006.01) |

(Continued)

(52) U.S. Cl.
CPC .......... *G03F 7/0045* (2013.01); *C07C 309/12* (2013.01); *C07C 381/12* (2013.01); *C07D 307/77* (2013.01); *C07D 311/00* (2013.01); *C07D 327/06* (2013.01); *C07D 333/08* (2013.01); *C07D 333/76* (2013.01); *C08F 220/18* (2013.01); *G03F 7/0382* (2013.01); *G03F 7/0397* (2013.01); *G03F 7/162* (2013.01); *G03F 7/168* (2013.01); *G03F 7/2006* (2013.01); *G03F 7/2043* (2013.01); *G03F 7/322* (2013.01); *G03F 7/325* (2013.01); *G03F 7/38* (2013.01)

(58) Field of Classification Search
CPC .......................... C07C 3091/12; C07C 381/12
See application file for complete search history.

(56) References Cited

U.S. PATENT DOCUMENTS

| | | | |
|---|---|---|---|
| 7,875,746 B2 | 1/2011 | Wada | |
| 8,227,183 B2 | 7/2012 | Tsubaki et al. | |

(Continued)

FOREIGN PATENT DOCUMENTS

| | | |
|---|---|---|
| JP | 2006-84530 A | 3/2006 |
| JP | 2006-84660 A | 3/2006 |

(Continued)

OTHER PUBLICATIONS

Office Action dated Aug. 27, 2020, issued in counterpart TW Application No. 108141094. (10 pages).

(Continued)

*Primary Examiner* — Amanda C. Walke
(74) *Attorney, Agent, or Firm* — WHDA, LLP

(57) ABSTRACT

A novel salt having an amide bond in its anion structure is provided. A chemically amplified resist composition comprising the salt has advantages including minimal defects and improved values of sensitivity, LWR, MEF and CDU, when processed by lithography using high-energy radiation such as KrF excimer laser, ArF excimer laser, EB or EUV.

21 Claims, 4 Drawing Sheets

(51) Int. Cl.
*C07D 311/00* (2006.01)
*C07D 333/76* (2006.01)
*C07D 333/08* (2006.01)
*C07D 327/06* (2006.01)
*C08F 220/18* (2006.01)
*G03F 7/039* (2006.01)
*G03F 7/32* (2006.01)
*G03F 7/16* (2006.01)
*G03F 7/20* (2006.01)
*G03F 7/38* (2006.01)

(56) References Cited

U.S. PATENT DOCUMENTS

| | | | | |
|---|---|---|---|---|
| 8,283,106 | B2 * | 10/2012 | Maeda | C09D 133/16 |
| | | | | 430/270.1 |
| 8,647,812 | B2 * | 2/2014 | Fujii | G03F 7/2041 |
| | | | | 430/270.1 |
| 9,069,246 | B2 * | 6/2015 | Takizawa | G03F 7/004 |
| 9,551,931 | B2 * | 1/2017 | Ito | C08F 220/26 |
| 9,904,167 | B2 * | 2/2018 | Tsuchimura | C07D 335/16 |
| 10,095,111 | B2 * | 10/2018 | Nihashi | G03F 7/38 |
| 10,120,278 | B2 * | 11/2018 | Fukushima | G03F 7/162 |
| 10,180,626 | B2 * | 1/2019 | Fujiwara | G03F 7/0397 |
| 10,261,417 | B2 * | 4/2019 | Goto | C07C 309/06 |
| 10,613,437 | B2 * | 4/2020 | Hatakeyama | C07C 309/48 |
| 11,163,232 | B2 * | 11/2021 | Hatakeyama | C07C 309/09 |
| 2006/0166135 | A1 | 7/2006 | Wada | |
| 2006/0210921 | A1 | 9/2006 | Watanabe | |
| 2010/0255419 | A1 * | 10/2010 | Kodama | G03F 7/0045 |
| | | | | 430/270.1 |
| 2011/0003247 | A1 | 1/2011 | Ohashi et al. | |
| 2011/0217654 | A1 | 9/2011 | Yamato et al. | |
| 2016/0033862 | A1 | 2/2016 | Shibuya | |
| 2016/0116840 | A1 | 4/2016 | Tsuchimura | |
| 2016/0349612 | A1 | 12/2016 | Fujiwara et al. | |
| 2017/0115566 | A1 * | 4/2017 | Hatakeyama | G03F 7/2037 |
| 2017/0369616 | A1 | 12/2017 | Hatakeyama et al. | |
| 2018/0267402 | A1 | 9/2018 | Hatakeyama et al. | |
| 2018/0364571 | A1 * | 12/2018 | Nishio | G03F 7/0392 |
| 2019/0033716 | A1 * | 1/2019 | Ohashi | G03F 7/0046 |
| 2019/0113843 | A1 | 4/2019 | Hatakeyama et al. | |
| 2019/0361343 | A1 | 11/2019 | Onishi et al. | |
| 2019/0361344 | A1 * | 11/2019 | Yamazaki | G03F 7/0397 |
| 2019/0361345 | A1 | 11/2019 | Ikeda et al. | |

FOREIGN PATENT DOCUMENTS

| | | | |
|---|---|---|---|
| JP | 2006-201711 | A | 8/2006 |
| JP | 2006-258980 | A | 9/2006 |
| JP | 2006-330098 | A | 12/2006 |
| JP | 2008-281974 | A | 11/2008 |
| JP | 2008-281975 | A | 11/2008 |
| JP | 2010-8912 | A | 1/2010 |
| JP | 2010-134279 | A | 6/2010 |
| JP | 4554665 | B2 | 9/2010 |
| JP | 2011-13479 | A | 1/2011 |
| JP | 2011-16746 | A | 1/2011 |
| JP | 2011-148766 | A | 8/2011 |
| JP | 2011-184434 | A | 9/2011 |
| JP | 2012032602 | A * | 2/2012 |
| JP | 2012-136505 | A | 7/2012 |
| JP | 2013-520458 | A | 6/2013 |
| JP | 2015-63470 | A | 4/2015 |
| JP | 2015-63471 | A | 4/2015 |
| JP | 2016-177256 | A | 10/2016 |
| JP | 2018-5224 | A | 1/2018 |
| JP | 2018-155908 | A | 10/2018 |
| JP | 2018-199781 | A | 12/2018 |
| JP | 2019-074731 | A | 5/2019 |
| JP | 2019-207299 | A | 12/2019 |
| JP | 2019-207300 | A | 12/2019 |
| JP | 2019-207408 | A | 12/2019 |
| KR | 10-2012-0072076 | A | 7/2012 |
| TW | 201512267 | A | 4/2015 |
| TW | 201708188 | A | 3/2017 |
| WO | 2009/019793 | A1 | 2/2009 |
| WO | 2009/033069 | A1 | 3/2009 |
| WO | 2011/104127 | A1 | 9/2011 |
| WO | 2014/034190 | A1 | 3/2014 |
| WO | 2014/185288 | A1 | 11/2014 |
| WO | 2017/179727 | A1 | 10/2017 |

OTHER PUBLICATIONS

Grande, D. et al, "Novel Routes to Functional (Meso)Porous Cross-Linked Polymers Using (Semi-)Interpenetrating Polymer Networks as Nanostructured Precursors", Macromolecular Symposia, 2010, 291-292 pp. 168-176, cited in JP Office Action dated Aug. 10, 2021. (9 pages).

Gopakumar, A. et al, "UV-Imprint Resists Generated from Polymerizable Ionic Liquids and Titania Nanoparticles", The Journal of Physical Chemistry C, 2014,118, pp. 16743-16748, cited in JP Office Action dated Aug. 10, 2021. (6 pages).

Office Action dated Aug. 10, 2021, issued in counterpart JP Application No. 2018-214718, with machine translation. (15 pages).

* cited by examiner

SALT COMPOUND, CHEMICALLY AMPLIFIED RESIST COMPOSITION, AND PATTERNING PROCESS

CROSS-REFERENCE TO RELATED APPLICATION

This non-provisional application claims priority under 35 U.S.C. § 119(a) on Patent Application No. 2018-214718 filed in Japan on Nov. 15, 2018, the entire contents of which are hereby incorporated by reference.

TECHNICAL FIELD

This invention relates to a novel salt compound, a chemically amplified resist composition, and a pattern forming process.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, the self-aligned double patterning (SADP) process of adding film to opposite sidewalls of lines of a resist pattern resulting from ArF lithography for thereby forming two patterns with half line width from one pattern is successful in manufacturing microelectronic devices at the 20-nm node in a mass scale. As the miniaturization technology for microelectronic devices of the next generation 10-nm node, the self-aligned quadruple patterning (SAQP) which is double repetition of SADP is a candidate. It is pointed out that this process is quite expensive because formation of sidewall film by CVD and processing by dry etching are repeated several times. Extreme ultraviolet (EUV) lithography of wavelength 13.5 nm is capable of forming a pattern with a size of the order of 10 nm via single exposure, with development efforts to implement the EUV lithography in practice being accelerated.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. The ArF immersion lithography is now implemented on the commercial stage. The immersion lithography requires a resist material which is substantially insoluble in water.

In the photolithography using an ArF excimer laser (wavelength 193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polymers of acrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Recently a highlight is put on the negative tone resist adapted for organic solvent development as well as the positive tone resist adapted for alkaline development. It would be desirable if a very fine hole pattern, which is not achievable with the positive tone, is resolvable through negative tone exposure. To this end, a positive resist material featuring a high resolution is subjected to organic solvent development to form a negative pattern. An attempt to double a resolution by combining two developments, alkali development and organic solvent development is under study. As the ArF resist material for negative tone development with organic solvent, positive ArF resist compositions of the prior art design may be used. Such pattern forming processes are described in Patent Documents 1 to 3.

To meet the current rapid progress of microfabrication technology, development efforts are put on not only the process, but also the resist material. Studies have also been made on photoacid generators (PAGs). Commonly used are sulfonium salts of triphenylsulfonium cation with perfluoroalkanesulfonic acid anion. These salts generate perfluoroalkanesulfonic acids, especially perfluorooctanesulfonic acid (PFOS), which are considered problematic with respect to their non-degradability, biological concentration and toxicity. It is rather restricted to apply these salts to the resist material. Instead, PAGs capable of generating perfluorobutanesulfonic acid are currently used, but are awkward to achieve a high resolution because of substantial diffusion of the generated acid in the resist material. To address the problem, partially fluorinated alkane sulfonic acids and salts thereof are developed. For instance, Patent Document 1 refers to the prior art PAGs capable of generating $\alpha,\alpha$-difluoroalkanesulfonic acid, such as di(4-tert-butylphenyl) iodonium 1,1-difluoro-2-(1-naphthyl)ethanesulfonate and PAGs capable of generating $\alpha,\alpha,\beta,\beta$-tetrafluoroalkanesulfonic acid. Despite a reduced degree of fluorine substitution, these PAGs still have the following problems. Since they do not have a decomposable substituent group such as ester structure, they are unsatisfactory from the aspect of environmental safety due to ease of decomposition. The molecular design to change the size of alkanesulfonic acid is limited. Fluorine-containing starting reactants are expensive.

As the circuit line width is reduced, the degradation of contrast by acid diffusion becomes more serious for the resist material. The reason is that the pattern feature size is approaching the diffusion length of acid. This invites a lowering of mask fidelity and a degradation of pattern rectangularity because a dimensional shift on wafer (known as mask error factor (MEF)) relative to a dimensional shift on mask is exaggerated. Accordingly, to gain more benefits from a reduction of exposure light wavelength and an increase of lens NA, the resist material is required to increase a dissolution contrast or restrain acid diffusion, as compared with the prior art materials. One approach is to lower the bake temperature for suppressing acid diffusion and hence, improving MEF. A low bake temperature, however, inevitably leads to a low sensitivity.

Incorporating a polar group into PAG is effective for suppressing acid diffusion. Patent Documents 4 and 5 describe salt compounds having an amide group in their anion structure. A resist composition comprising this PAG, however, is still insufficient in precise control of acid diffusion, and its lithography performance is unsatisfactory when evaluated totally in terms of LWR as an index of pattern roughness and resolution.

As the PAG which is effective for controlling acid diffusion, for example, Patent Document 6 describes a PAG of betaine structure (having both cation and anion structures in one molecule) capable of generating perfluoroalkanesulfonic acid. When the PAG of betaine structure generates an acid, it becomes an apparently giant compound by forming a salt compound between molecules or with another PAG if added concurrently. As a result, there are presumably obtained advantages including improved dissolution contrast, suppressed acid diffusion, and improved lithography performance. However, since the PAG of betaine structure is less soluble in resist solvents and likely to assume a dimer form, it will partially agglomerate in the resist film, resulting in less uniform dispersion within the resist film and inviting degradations of LWR and CDU.

As the PAG which has a high solubility in organic solvents and causes less defect development, there are known compounds containing an anion having an acid generating site of imide acid or methide acid structure. Patent Documents 7 to 10 describe PAGs of imide or methide acid type. However, the PAGs described therein allow for noticeable acid diffusion, and their lithography performance is unsatisfactory to the current requirement to form resist patterns at high resolution.

CITATION LIST

Patent Document 1: JP-A 2008-281974

Patent Document 2: JP-A 2008-281975

Patent Document 3: JP 4554665 (U.S. Pat. No. 8,227,183)

Patent Document 4: JP-A 2010-134279

Patent Document 5: KR-A 10-2012-0072076

Patent Document 6: JP-A 2011-016746

Patent Document 7: JP-A 2010-008912

Patent Document 8: JP-A 2006-084660

Patent Document 9: JP-A 2006-084530 Patent Document 10: JP-A 2006-330098 (U.S. Pat. No. 7,875,746)

DISCLOSURE OF THE INVENTION

An object of the invention is to provide a salt compound suited for use in resist compositions. Another object is to provide a chemically amplified resist composition which forms a pattern with advantages including minimal defects and improved sensitivity, LWR, MEF, and CDU when processed by photolithography using high-energy radiation such as KrF excimer laser, ArF excimer laser, EB or EUV as the light source; and a patterning process using the resist composition.

The inventors have found that the above and other objects are attained by a photoacid generator in the form of an onium salt having a specific structure, and a chemically amplified resist composition comprising the photoacid generator is a quite effective resist material for precise micropatterning, having lithography performance advantages including reduced acid diffusion, and improved EL, MEF, CDU and LWR.

In one aspect, the invention provides a salt compound having the formula (A).

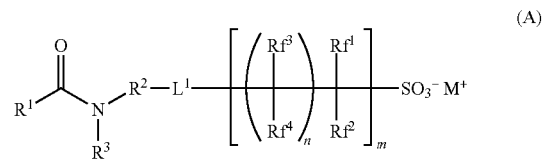

Herein $R^1$ is a $C_1$-$C_{20}$ monovalent hydrocarbon group which may contain a heteroatom, $R^2$ is a $C_1$-$C_{20}$ divalent hydrocarbon group which may contain a heteroatom, $R^3$ is hydrogen or a $C_1$-$C_{12}$ monovalent hydrocarbon group, $R^1$ and $R^3$ may bond together to form a ring with the carbon and nitrogen atoms to which they are attached, $R^{f1}$, $R^{f2}$, $R^{f3}$ and $R^{f4}$ are each independently hydrogen, fluorine or trifluoromethyl, $L^1$ is a single bond, —CO—O—, —O—CO—, —O—CO—O— or —O—, $M^+$ is a monovalent organic cation, m is 0 or 1, and n is 0 or 1.

In a preferred embodiment, m is 1, n is 1, $R^{f1}$ and $R^{f2}$ are fluorine, $R^{f3}$ and $R^{f4}$ are hydrogen.

In another preferred embodiment, m is 1, n is 1, $R^{f1}$ and $R^{f2}$ are fluorine, $R^{f3}$ is trifluoromethyl, and $R^{f4}$ is hydrogen.

In a preferred embodiment, $R^1$ is a lactone structure-containing group.

Preferably, $M^+$ is a sulfonium cation having the formula (A1), an iodonium cation having the formula (A2) or an ammonium cation having the formula (A3).

Herein $R^{11}$ to $R^{19}$ are each independently a $C_1$-$C_{20}$ monovalent hydrocarbon group which may contain a heteroatom.

In a second aspect, the invention provides a photoacid generator comprising the salt compound defined above.

In a third aspect, the invention provides a chemically amplified resist composition comprising the photoacid generator defined above.

The resist composition may further comprise a base resin containing a polymer comprising recurring units having the formula (a) and recurring units having the formula (b).

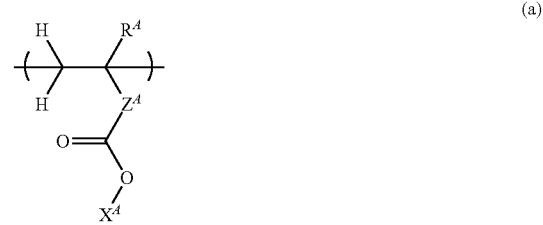

-continued

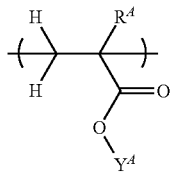
(b)

Herein $R^A$ is each independently hydrogen, fluorine, methyl or trifluoromethyl, $Z^A$ is a single bond, phenylene, naphthylene or (backbone)-C(=O)—O—Z'—, Z' is a $C_1$-$C_{10}$ alkanediyl group which may contain a hydroxyl moiety, ether bond, ester bond or lactone ring, or a phenylene or naphthylene group, $X^A$ is an acid labile group, and $Y^A$ is hydrogen or a polar group containing at least one structure selected from the group consisting of hydroxyl, cyano, carbonyl, carboxyl, ether bond, ester bond, sulfonate bond, carbonate bond, lactone ring, sultone ring and carboxylic anhydride.

The resist composition may further comprise an organic solvent.

The resist composition may further comprise a quencher. Preferably, the quencher contains a compound having the formula (1a) or (1b).

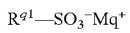
(1a)

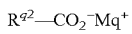
(1b)

Herein $R^{q1}$ is hydrogen or a $C_1$-$C_{40}$ monovalent hydrocarbon group which may contain a heteroatom, excluding the hydrocarbon group in which the hydrogen atom bonded to the carbon atom at α-position relative to the sulfo group is substituted by fluorine or fluoroalkyl, $R^{q2}$ is hydrogen or a $C_1$-$C_{40}$ monovalent hydrocarbon group which may contain a heteroatom, and $Mq^+$ is an onium cation.

Also preferably, the quencher contains an amine compound.

The resist composition may further comprise a photoacid generator other than the photoacid generator defined above.

Preferably, the other photoacid generator has the formula (3) or (4).

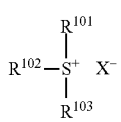
(3)

Herein $R^{101}$, $R^{102}$ and $R^{103}$ are each independently a $C_1$-$C_{20}$ monovalent hydrocarbon group which may contain a heteroatom, any two of $R^{101}$, $R^{102}$ and $R^{103}$ may bond together to form a ring with the sulfur atom to which they are attached, and $X^-$ is an anion selected from the following formulae (3A) to (3D):

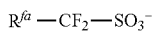
(3A)

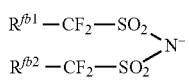
(3B)

$$R^{fc1}-CF_2-SO_2-\underset{\underset{R^{fc3}}{|}}{\overset{\overset{R^{fc2}}{|}}{\underset{|}{\overset{|}{C^-}}}}\begin{matrix}CF_2\\|\\SO_2\\|\\SO_2\\|\\CF_2\end{matrix}$$
(3C)

$$R^{fd}-\underset{}{\overset{O}{\overset{\|}{C}}}-O-\underset{\underset{CF_3}{|}}{\overset{\overset{CF_3}{|}}{C}}-CH_2-SO_3^-$$
(3D)

wherein $R^{fa}$, $R^{fb1}$, $R^{fb2}$, $R^{fc1}$, $R^{fc2}$ and $R^{fc3}$ are each independently fluorine or a $C_1$-$C_{40}$ monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a $C_1$-$C_{40}$ monovalent hydrocarbon group which may contain a heteroatom, $$R^{201}-S^+-R^{203}-L^A-\underset{\underset{X^d}{|}}{\overset{\overset{X^c}{|}}{C}}-\underset{\underset{X^b}{|}}{\overset{\overset{X^a}{|}}{C}}-SO_3^-$$
$$\underset{R^{202}}{|}$$
(4)

wherein $R^{201}$ and $R^{202}$ are each independently a $C_1$-$C_{30}$ monovalent hydrocarbon group which may contain a heteroatom, $R^{203}$ is a $C_1$-$C_{30}$ divalent hydrocarbon group which may contain a heteroatom, any two of $R^{201}$, $R^{202}$ and $R^{203}$ may bond together to form a ring with the sulfur atom to which they are attached, $L^A$ is a single bond, ether bond or a $C_1$-$C_{20}$ divalent hydrocarbon group which may contain a heteroatom, $X^a$, $X^b$, $X^c$ and $X^d$ are each independently hydrogen, fluorine or trifluoromethyl, at least one of $X^a$, $X^b$, $X^c$ and $X^d$ is fluorine or trifluoromethyl.

The resist composition may further comprise a surfactant which is insoluble or substantially insoluble in water and soluble in alkaline developer, and/or a surfactant which is insoluble or substantially insoluble in water and alkaline developer.

In a fourth aspect, the invention provides a pattern forming process comprising the steps of applying the chemically amplified resist composition defined above onto a substrate to form a resist film thereon, exposing a selected region of the resist film to KrF excimer laser, ArF excimer laser, EB or EUV, and developing the exposed resist film in a developer.

In a preferred embodiment, the developing step uses an alkaline aqueous solution as the developer, thereby forming a positive pattern in which an exposed region of the resist film is dissolved away and an unexposed region of the resist film is not dissolved.

In another preferred embodiment, the developing step uses an organic solvent as the developer, thereby forming a negative pattern in which an unexposed region of the resist film is dissolved away and an exposed region of the resist film is not dissolved.

Preferably, the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

In a preferred embodiment, the exposure step is carried out by immersion lithography while a liquid having a refractive index of at least 1.0 is held between the resist film and a projection lens.

The process may further comprise the step of forming a protective film on the resist film prior to the exposure step, wherein immersion lithography is carried out while the liquid is held between the protective film and the projection lens.

Advantageous Effects of Invention

The PAG in the form of the inventive salt compound generates an acid which is less diffusive in resist solvent and developer. When processed by lithography, a chemically amplified resist composition comprising the salt compound forms a pattern of good profile with a minimal LWR.

DESCRIPTION OF THE PREFERRED EMBODIMENTS

Figure 1:
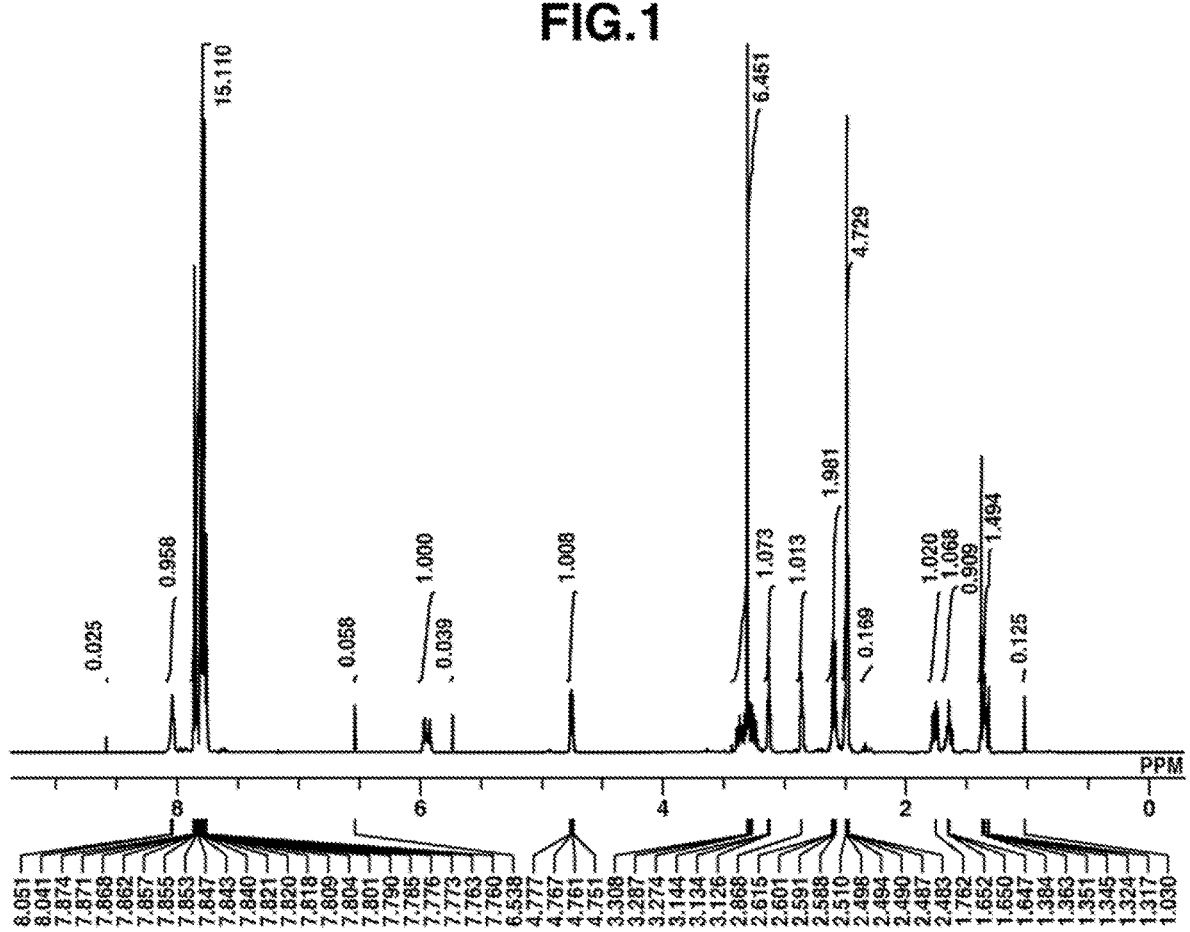
FIG. 1 is a diagram showing $^1$H-NMR spectrum of the compound in Example 1-1.

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line denotes a valence bond. It is understood that for some structures represented by chemical formulae, there can exist enantiomers and diastereomers because of the presence of asymmetric carbon atoms. In such a case, a single formula collectively represents all such isomers. The isomers may be used alone or in admixture.

The abbreviations have the following meaning.
EB: electron beam
EUV: extreme ultraviolet
PAG: photoacid generator
PEB: post-exposure bake
LWR: line width roughness
EL: exposure latitude
MEF: mask error factor
CDU: critical dimension uniformity
DOF: depth of focus
Salt Compound The invention provides a salt compound having the formula (A).

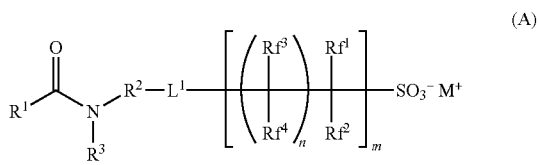

In formula (A), $R^1$ is a $C_1$-$C_{20}$ monovalent hydrocarbon group which may contain a heteroatom. $R^2$ is a $C_1$-$C_{20}$ divalent hydrocarbon group which may contain a heteroatom. $R^3$ is hydrogen or a $C_1$-$C_{12}$ monovalent hydrocarbon group. $R^1$ and $R^3$ may bond together to form a ring with the carbon and nitrogen atoms to which they are attached.

The $C_1$-$C_{20}$ monovalent hydrocarbon group which may contain a heteroatom, represented by $R^1$, may be straight, branched or cyclic. Examples include straight, branched or cyclic alkyl groups such as methyl, ethyl, propyl, isopropyl, n-butyl, sec-butyl, tert-butyl, n-pentyl, tert-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, and aryl groups such as phenyl, naphthyl and anthracenyl. In the foregoing groups, some hydrogen may be substituted by a moiety containing a heteroatom such as oxygen, sulfur, nitrogen or halogen, or a moiety containing a heteroatom such as oxygen, sulfur or nitrogen may intervene between carbon atoms, so that the group may contain a hydroxyl moiety, cyano moiety, carbonyl moiety, ether bond, ester bond, sulfonate bond, carbonate bond, lactone ring, sultone ring, carboxylic anhydride or haloalkyl moiety. Inter alia, $R^1$ is preferably a monovalent hydrocarbon group containing a lactone ring.

The $C_1$-$C_{20}$ divalent hydrocarbon group which may contain a heteroatom, represented by $R^2$, may be straight, branched or cyclic. Examples include straight or branched alkanediyl groups such as methylene, ethane-1,1-diyl, ethane-1,2-diyl, propane-1,1-diyl, propane-1,2-diyl, propane-1,3-diyl, propane-2,2-diyl, 2-methylpropane-1,1-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated divalent cyclic hydrocarbon groups such as cyclopentanediyl, cyclohexanediyl, norbornanediyl, and adamantanediyl; and arylene groups such as phenylene and naphthylene. In the foregoing groups, some hydrogen may be replaced by an alkyl group such as methyl, ethyl, propyl, n-butyl or t-butyl, or some hydrogen may be substituted by a moiety containing a heteroatom such as oxygen, sulfur, nitrogen or halogen, or a moiety containing a heteroatom such as oxygen, sulfur or nitrogen may intervene between carbon atoms, so that the group may contain a hydroxyl moiety, cyano moiety, carbonyl moiety, ether bond, ester bond, sulfonate bond, carbonate bond, lactone ring, sultone ring, carboxylic anhydride or haloalkyl moiety. Of the heteroatoms, oxygen is preferred.

The $C_1$-$C_{12}$ monovalent hydrocarbon group, represented by $R^3$, may be straight, branched or cyclic. Examples thereof include the monovalent hydrocarbon groups of 1 to 12 carbon atoms exemplified above for $R^1$.

In formula (A), $R^{f1}$, $R^{f2}$, $R^{f3}$ and $R^{f4}$ are each independently hydrogen, fluorine or trifluoromethyl, m is 0 or 1, preferably m=1, and n is 0 or 1, preferably n=1. Preferably at least one of $R^{f1}$, $R^{f2}$, $R^{f3}$ and $R^{f4}$ is fluorine or trifluoromethyl. Particularly when the salt compound having formula (A) is used as a PAG in a chemically amplified resist composition, it is preferred in view of the strength of generated acid that m=n=1, and $R^{f1}$ and $R^{f2}$ be fluorine, more preferably m=n=1, $R^{f1}$ and $R^{f2}$ be fluorine, $R^{f3}$ be trifluoromethyl, and $R^{f4}$ be hydrogen.

In formula (A), $L^1$ is a single bond, —CO—O—, —O—CO—, —O—CO—O— or —O—. It is preferred for the convenience of synthesis that $L^1$ be —CO—O— or —O—CO—.

Examples of the salt compound having formula (A) wherein $L^1$ is —CO—O— are shown below, but not limited thereto.

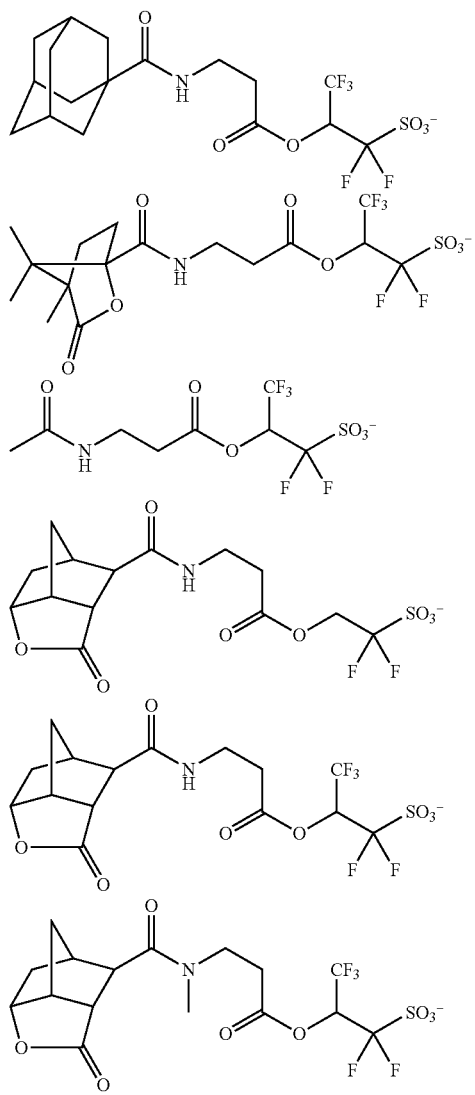

-continued

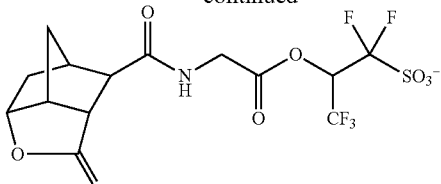

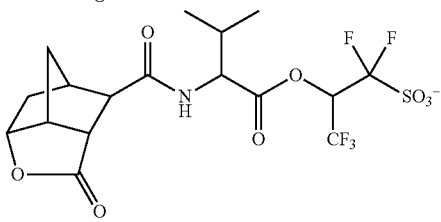

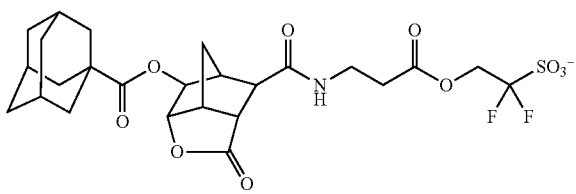

The salt compound has an amide bond in its anion structure. The amide group functions to provide the salt compound with an adequate polarity. It is thus expectable that the diffusion of the generated acid in a resist film is suppressed. Then a pattern of good profile is formed.

In formula (A), $M^+$ is a monovalent organic cation. The organic cation is preferably a sulfonium cation having the formula (A1), an iodonium cation having the formula (A2) or an ammonium cation having the formula (A3).

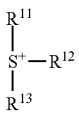 (A1)

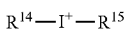 (A2)

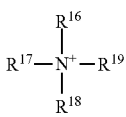 (A3)

Herein $R^{11}$ to $R^{19}$ are each independently a $C_1$-$C_{20}$ monovalent hydrocarbon group which may contain a heteroatom. The $C_1$-$C_{20}$ monovalent hydrocarbon group may be straight, branched or cyclic. Examples include alkyl groups such as methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, adamantyl; alkenyl groups such as vinyl, allyl, propenyl, butenyl, hexenyl, cyclohexenyl; aryl groups such as phenyl, naphthyl, thienyl; and aralkyl groups such as benzyl, 1-phenylethyl, 2-phenylethyl. In the foregoing groups, some hydrogen may be substituted by a heteroatom such as oxygen, sulfur, nitrogen or halogen, or a heteroatom such as oxygen, sulfur or nitrogen may intervene between carbon atoms, so that the group may contain a hydroxyl moiety, cyano moiety, carbonyl moiety, ether bond, ester bond, sulfonate bond, carbonate bond, lactone ring, sultone ring, carboxylic anhydride or haloalkyl moiety.

Any two of $R^{11}$ to $R^{13}$ may bond together to form a ring with the sulfur atom to which they are attached. Examples of the sulfonium cation having formula (A1) involving cyclization are shown below.

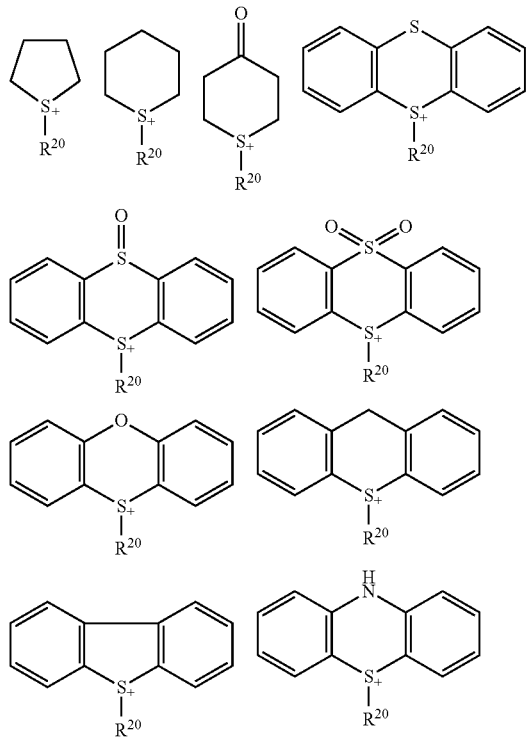

Herein $R^{20}$ is a $C_1$-$C_{20}$ monovalent hydrocarbon group which may contain a heteroatom. Examples of the monovalent hydrocarbon group are as exemplified above for $R^{11}$ to $R^{19}$.

Examples of the sulfonium cation having formula (A1) are shown below, but not limited thereto.

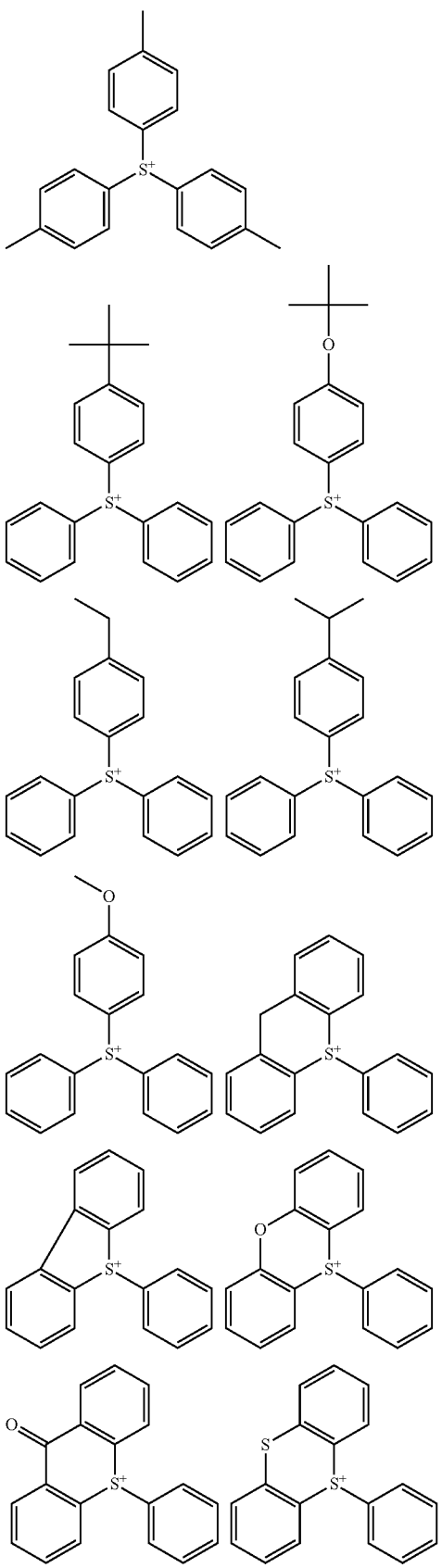

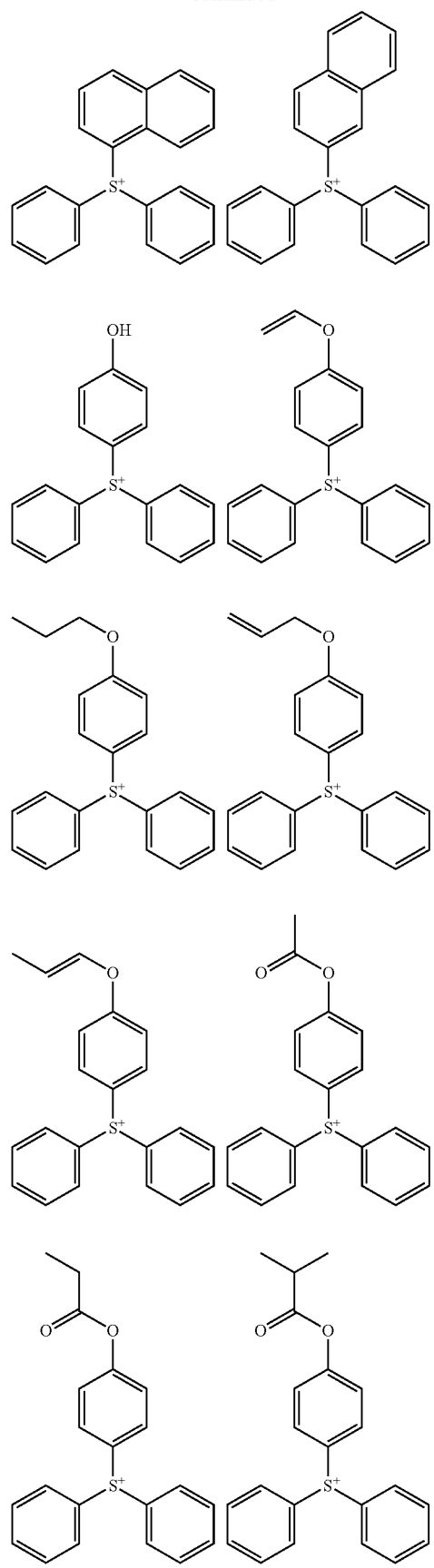
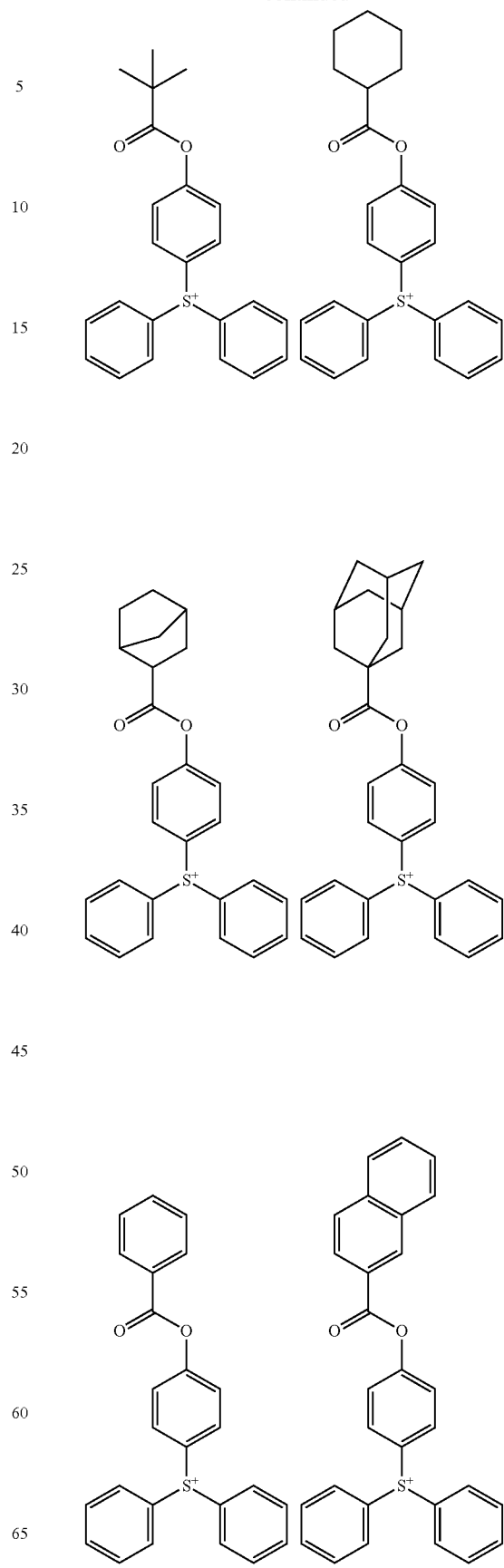

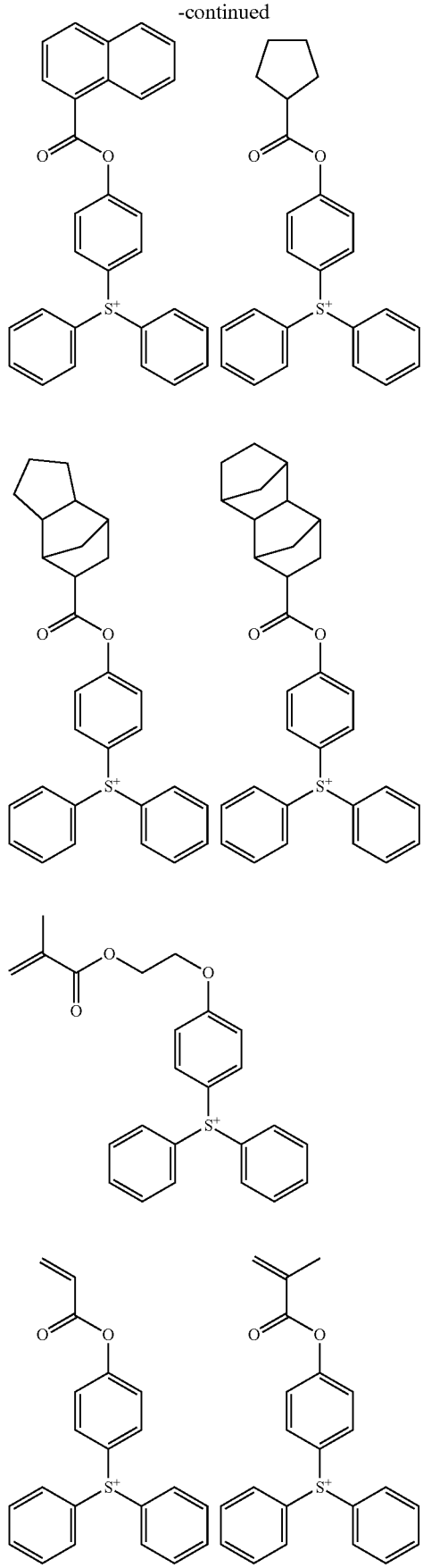
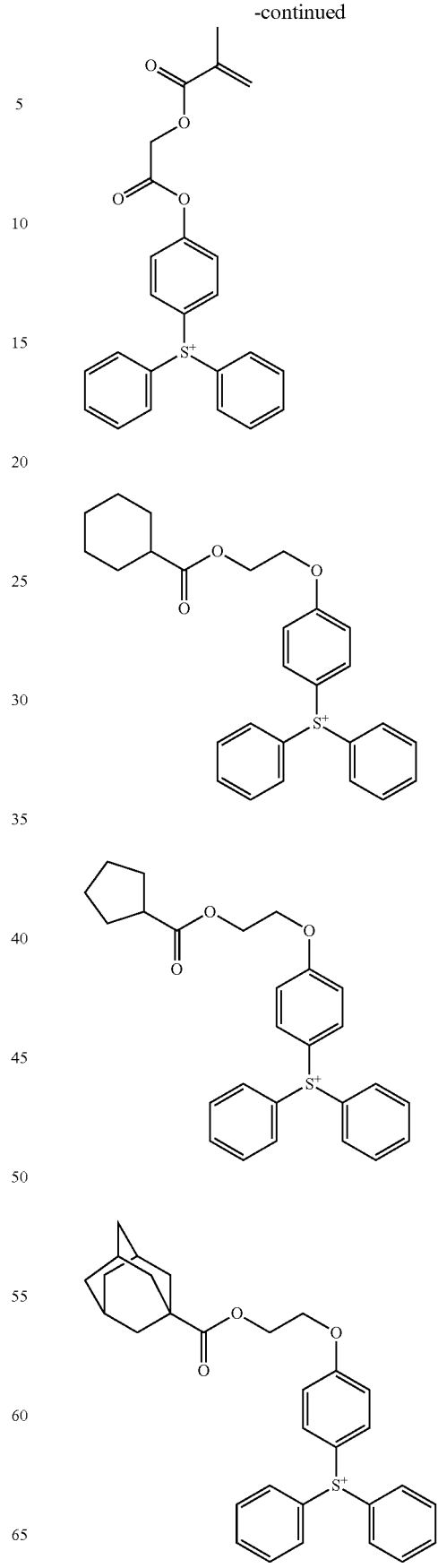

17
-continued
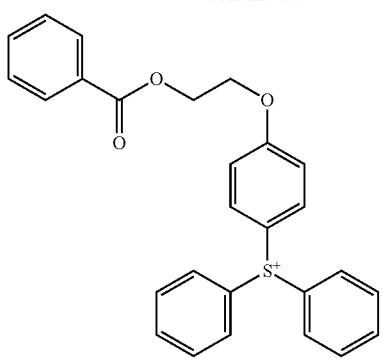
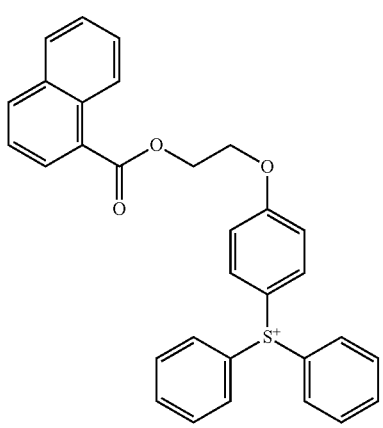
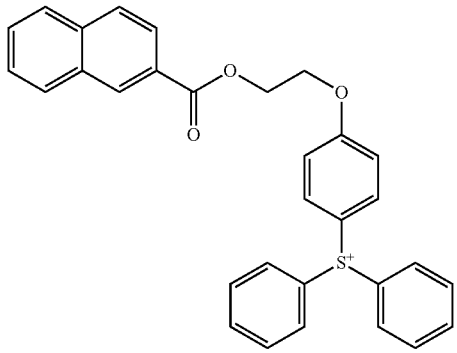
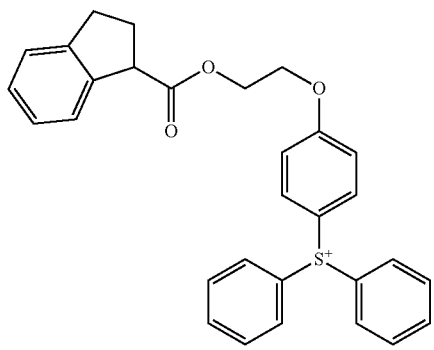
18
-continued
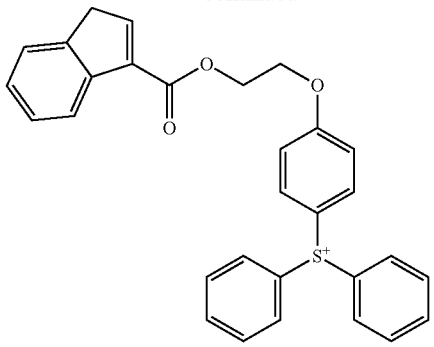
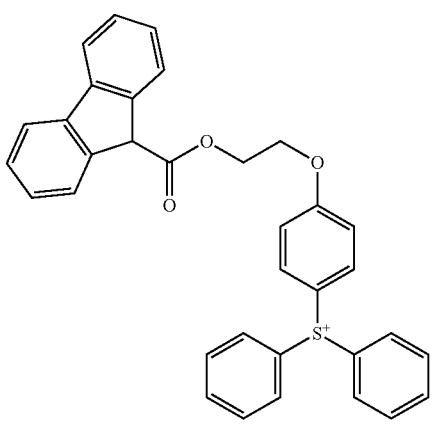
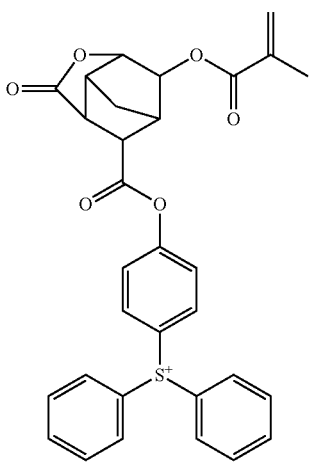
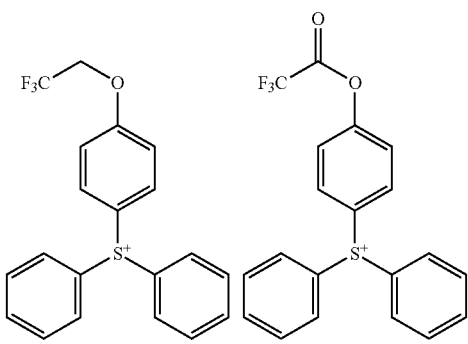

-continued
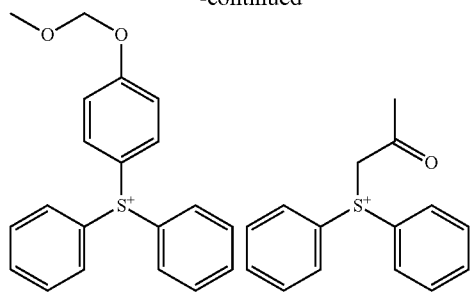
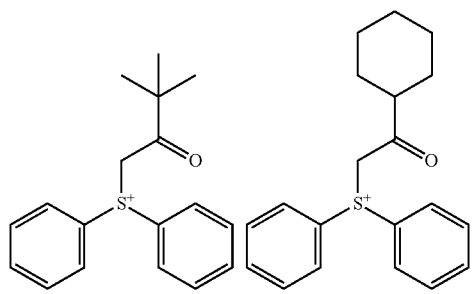
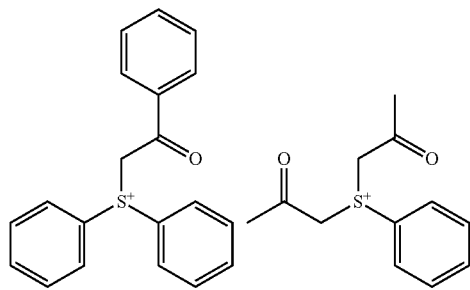
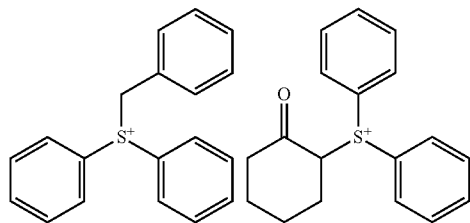
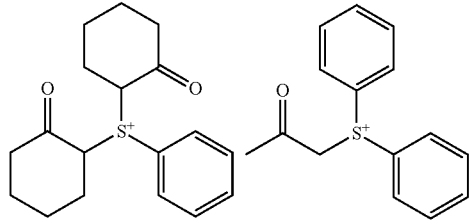
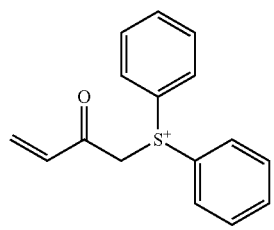
-continued
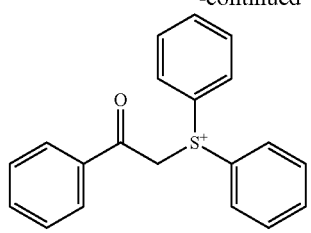
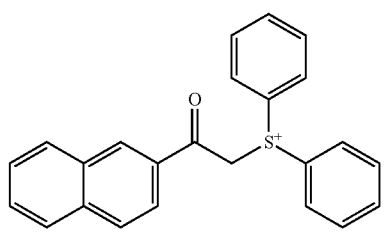
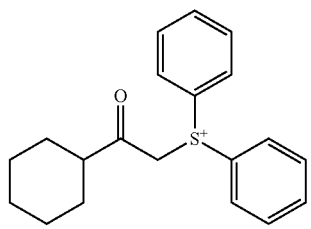
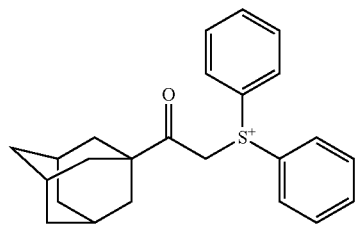
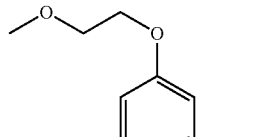
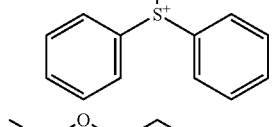
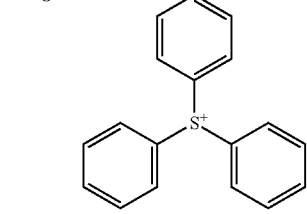

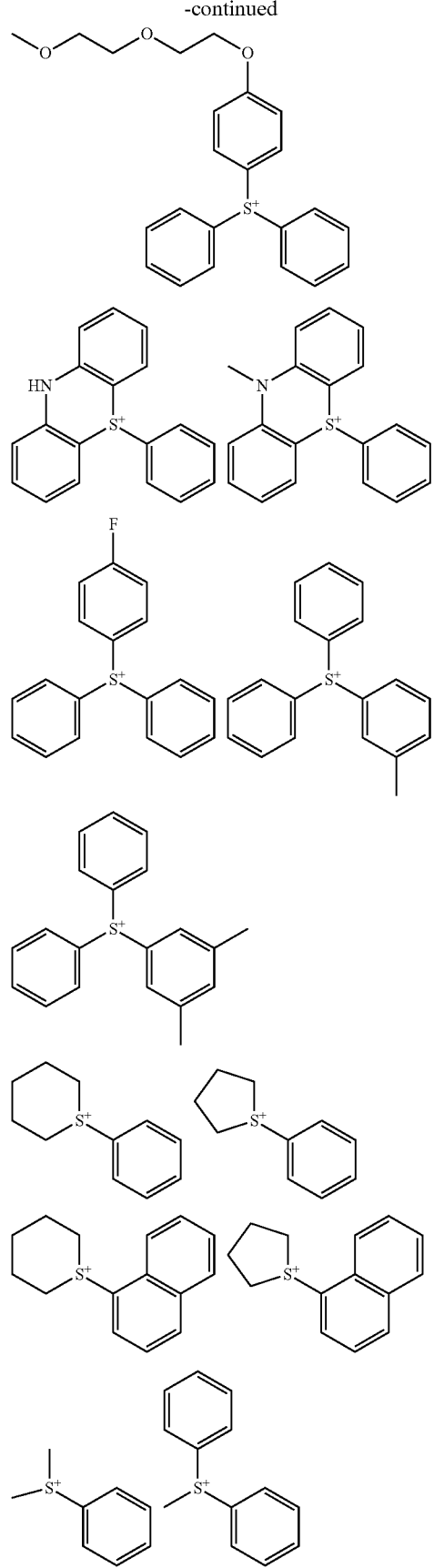
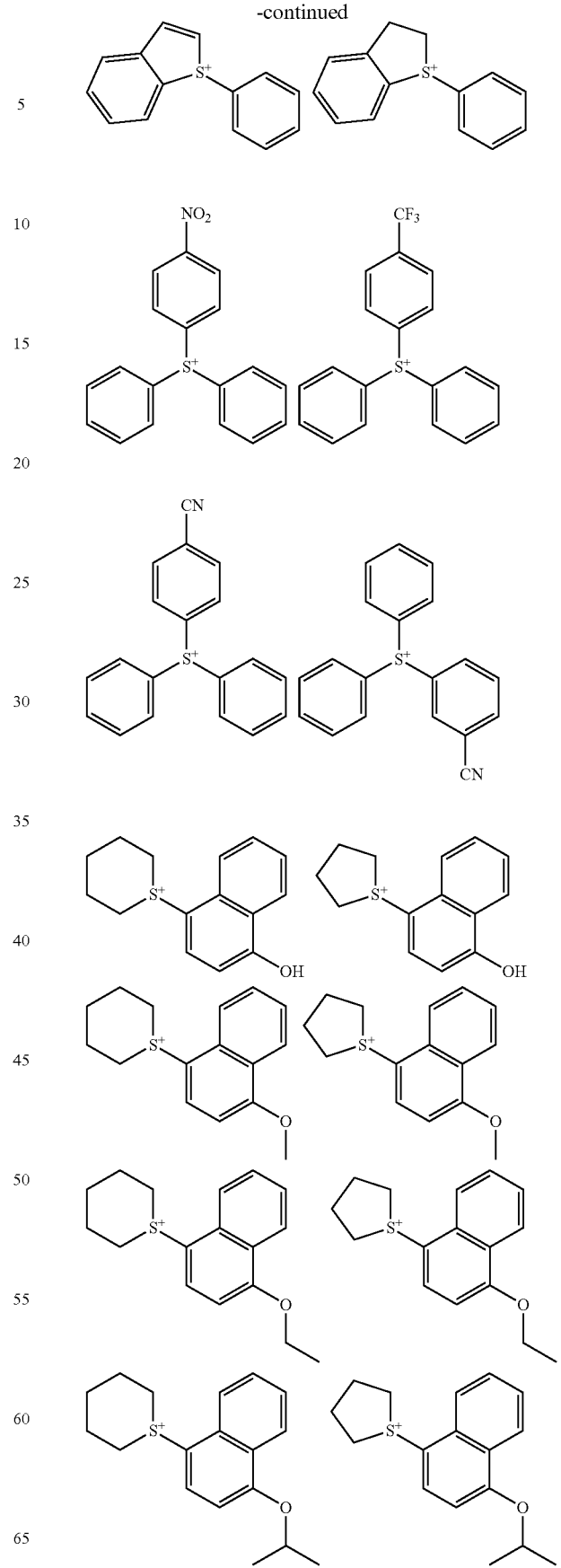

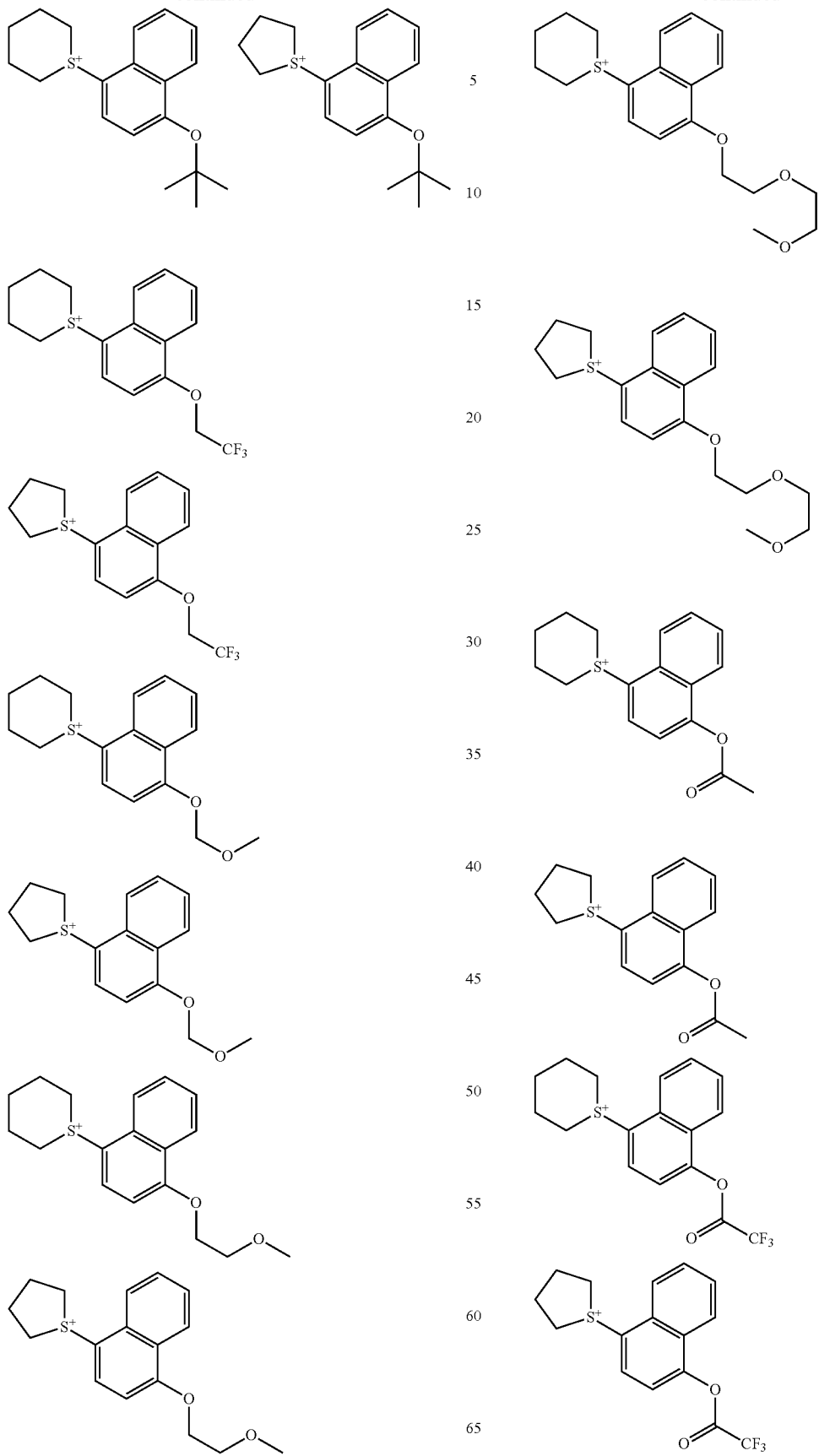

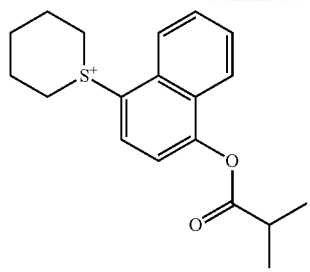
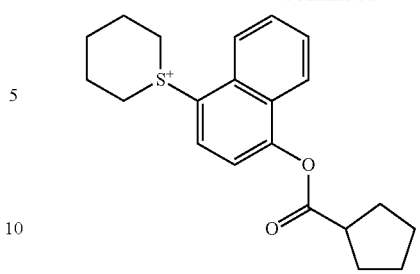
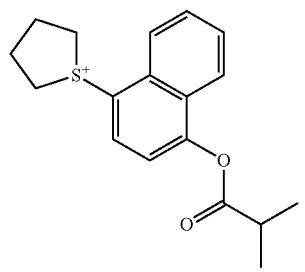
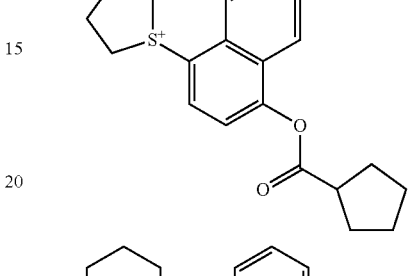
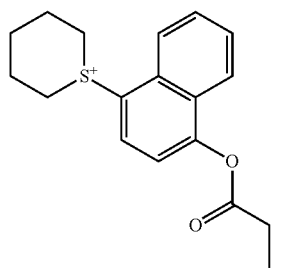
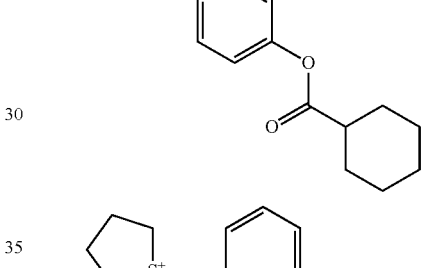
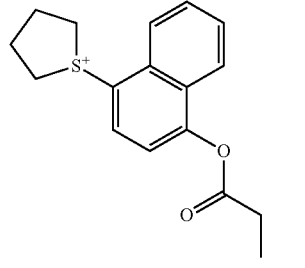
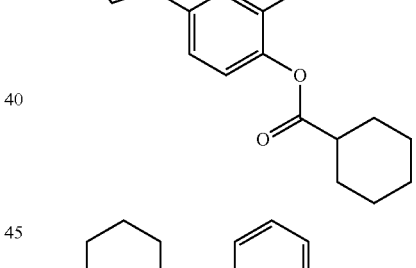
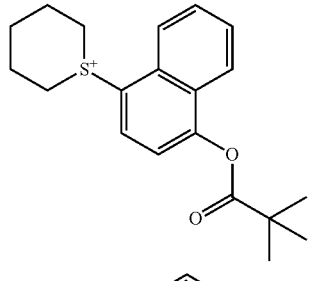
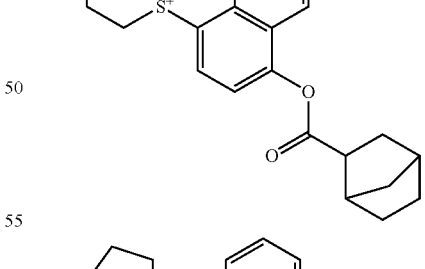
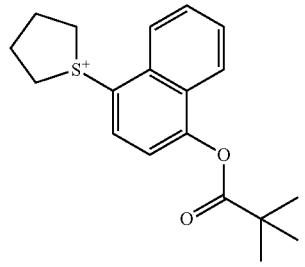
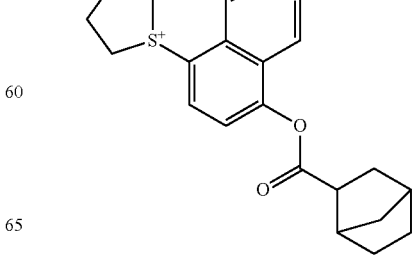

-continued
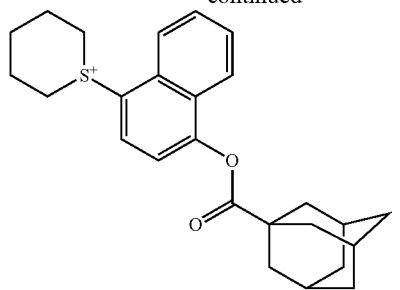
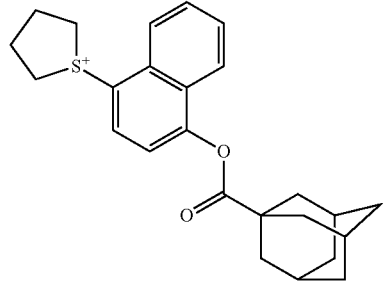
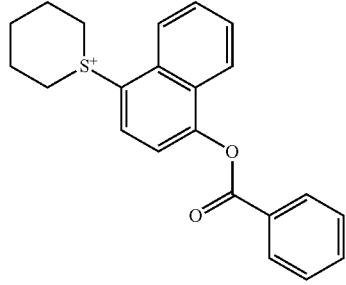
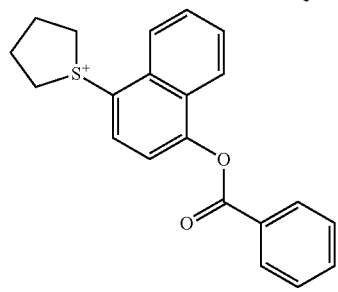
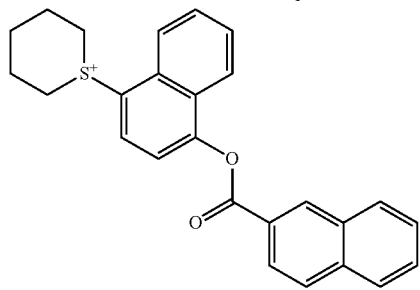
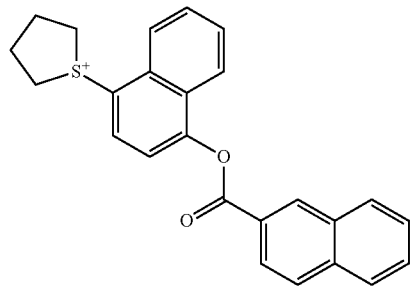
-continued
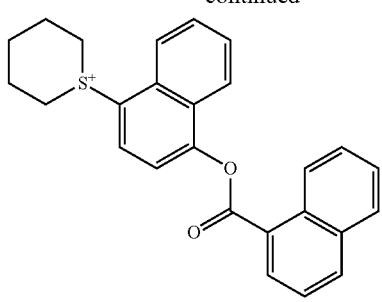
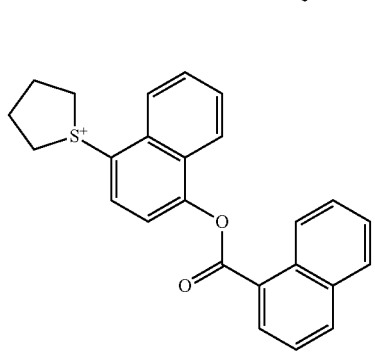
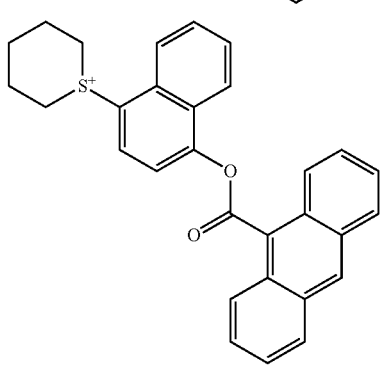
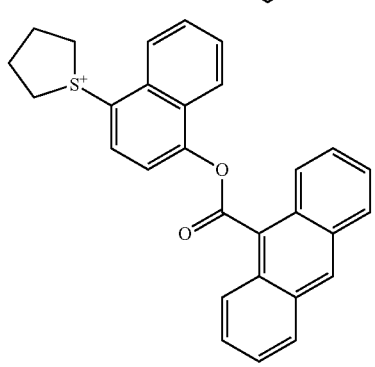
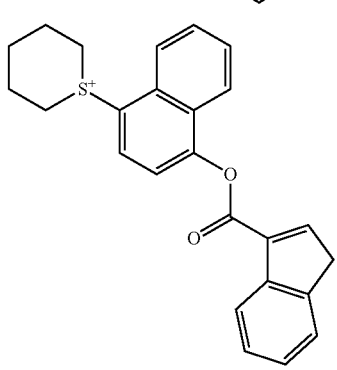

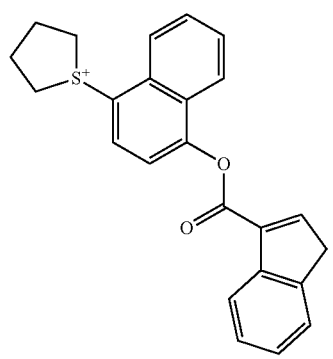
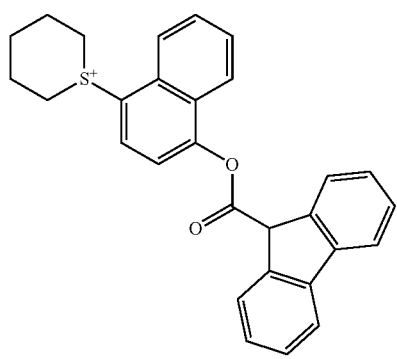
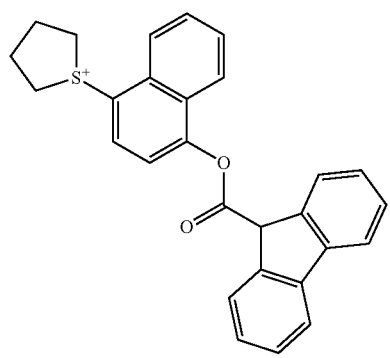
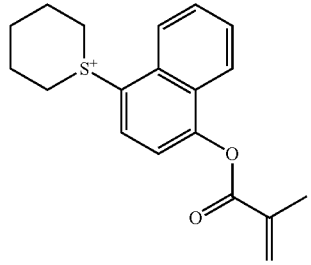
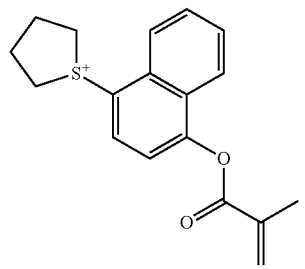
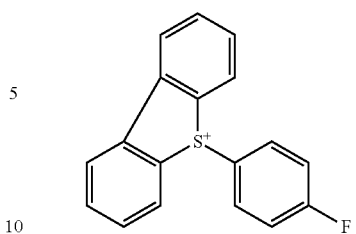
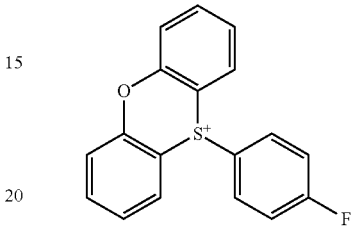
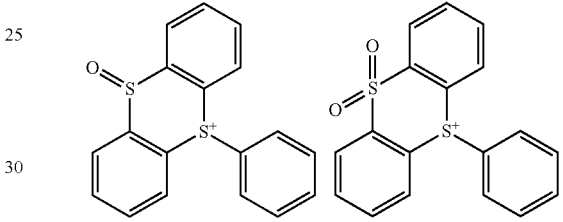
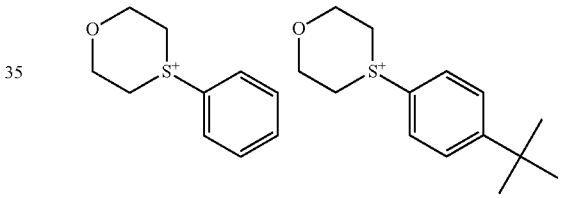
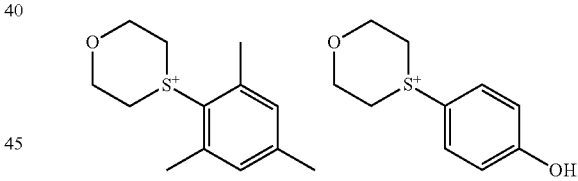
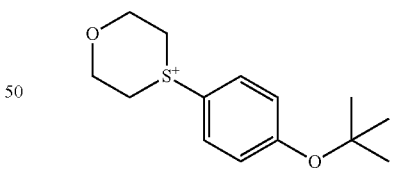
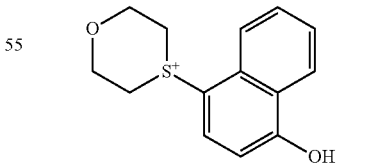
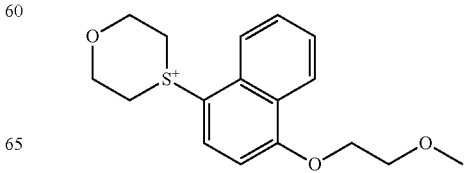

31
-continued
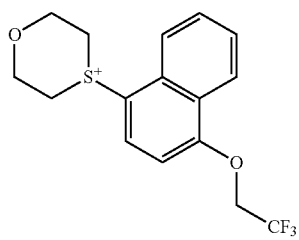
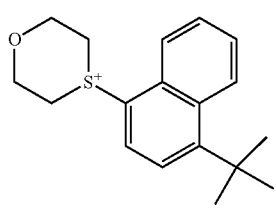
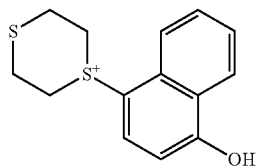
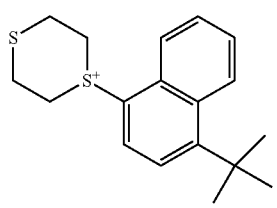
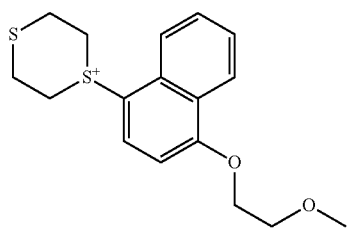
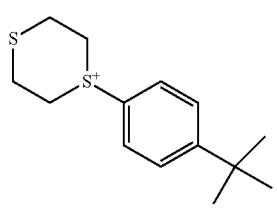
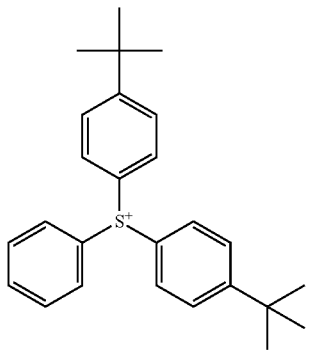
32
-continued
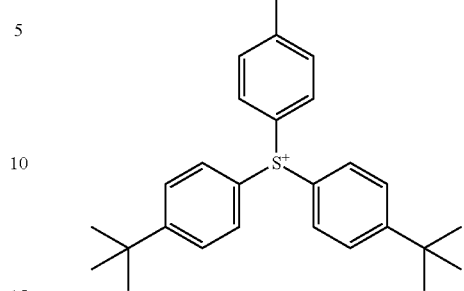
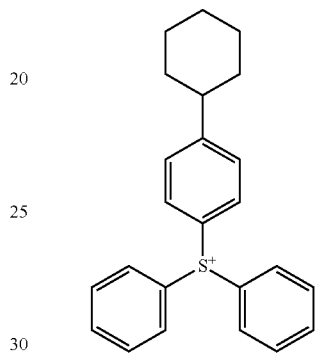
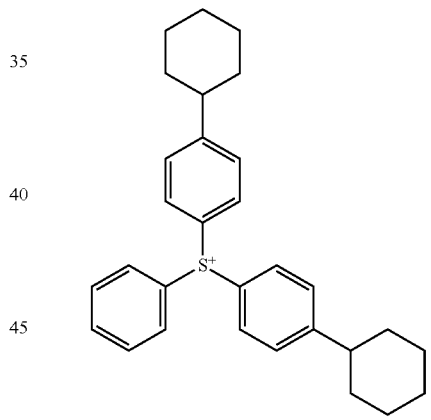
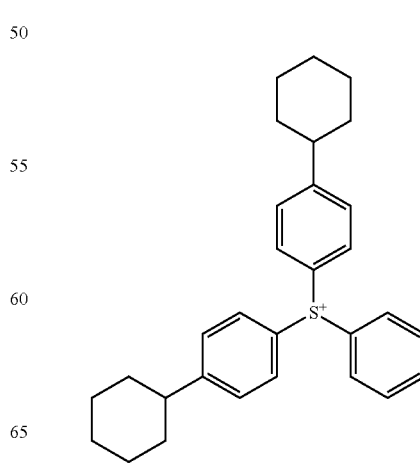

33
-continued
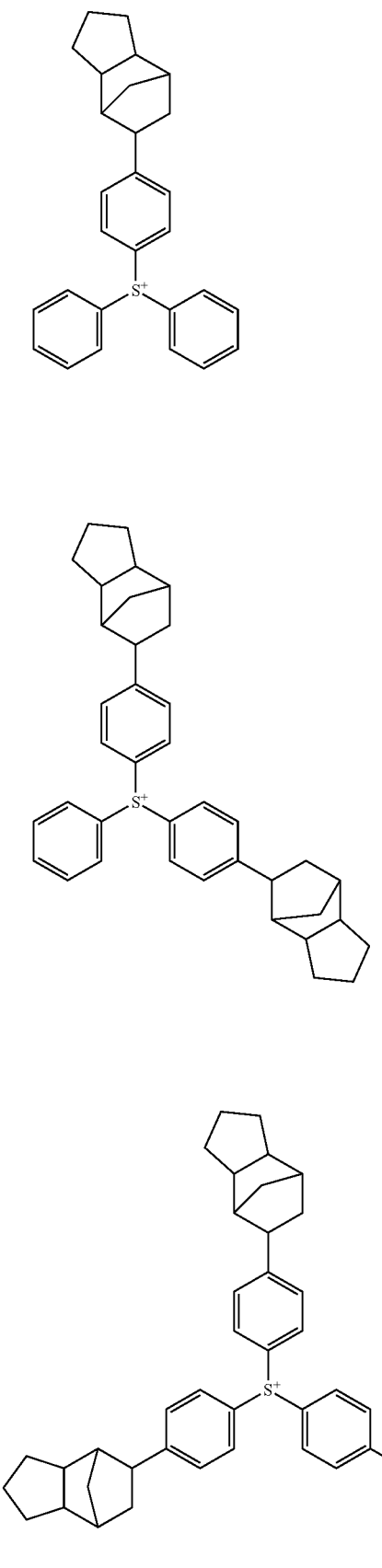
34
-continued
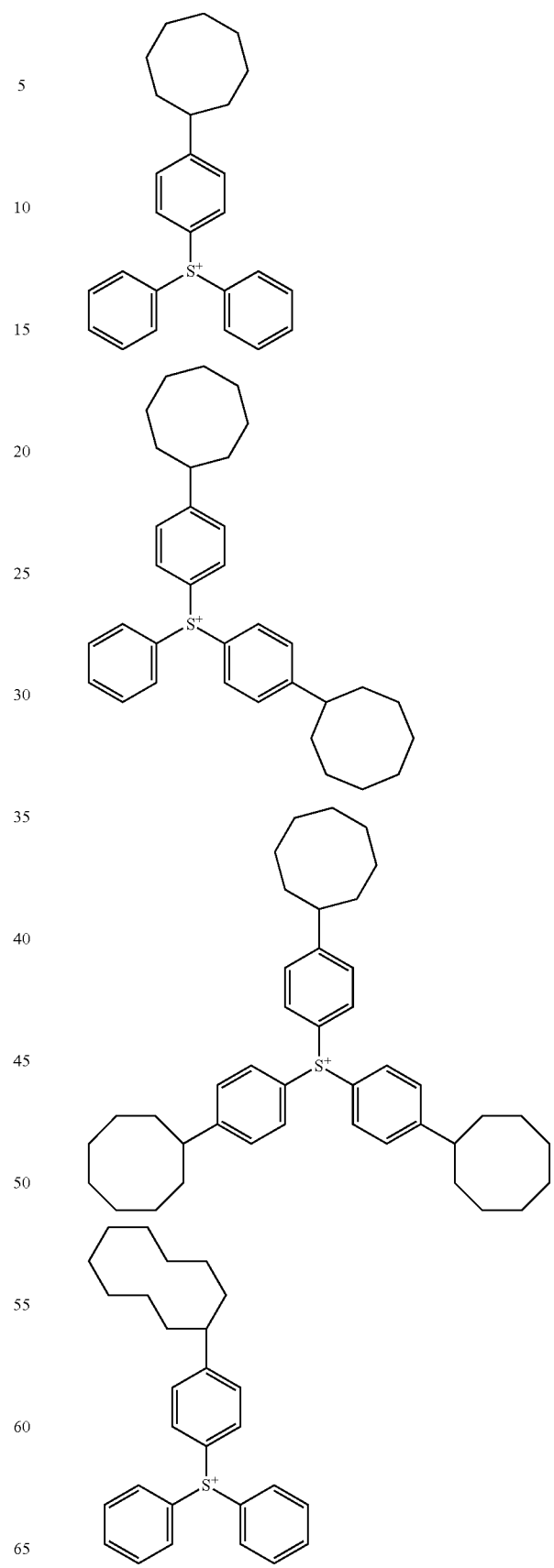

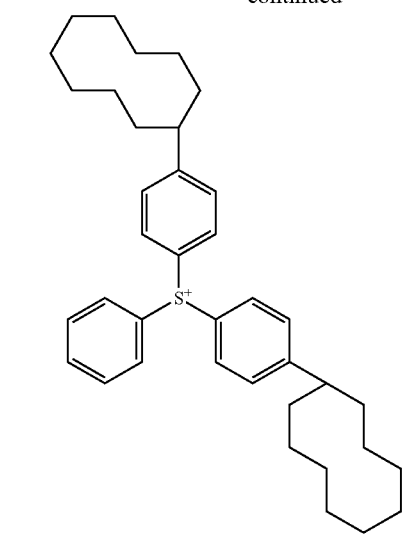
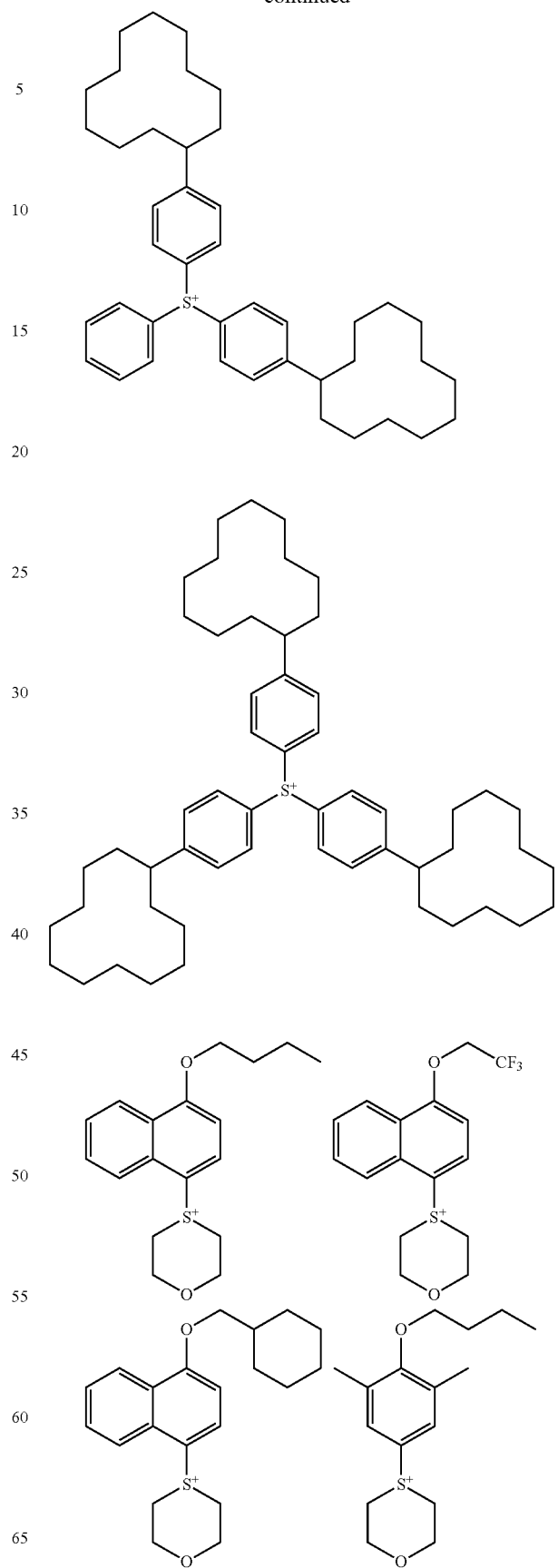

37
-continued
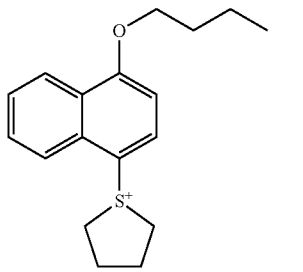
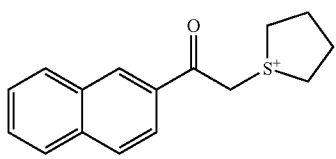
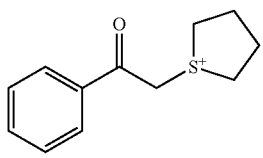
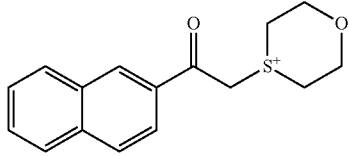
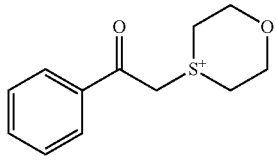
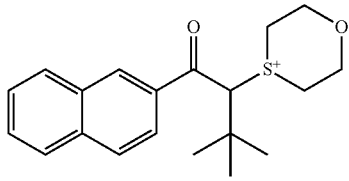
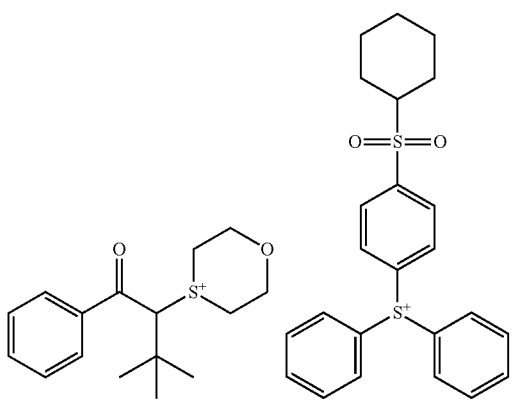
38
-continued
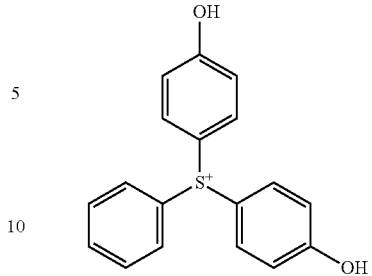
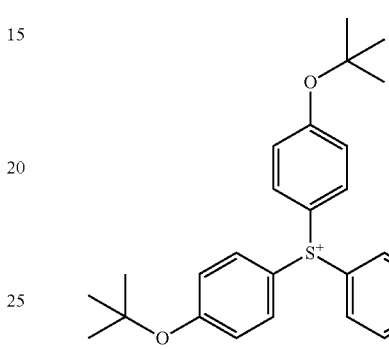
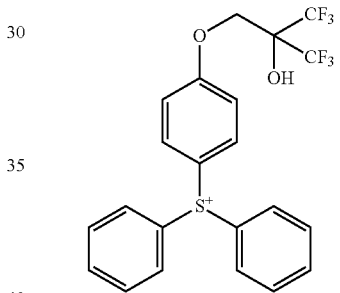
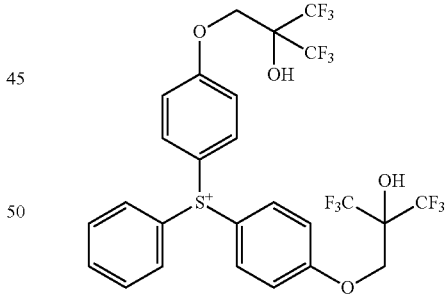
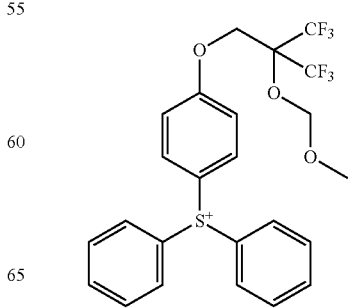

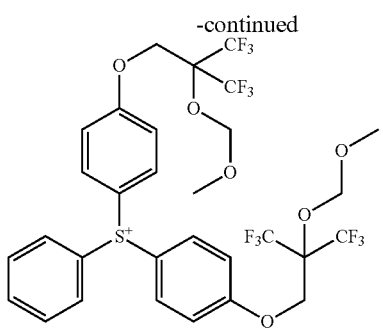
Examples of the iodonium cation having formula (A2) are shown below, but not limited thereto.
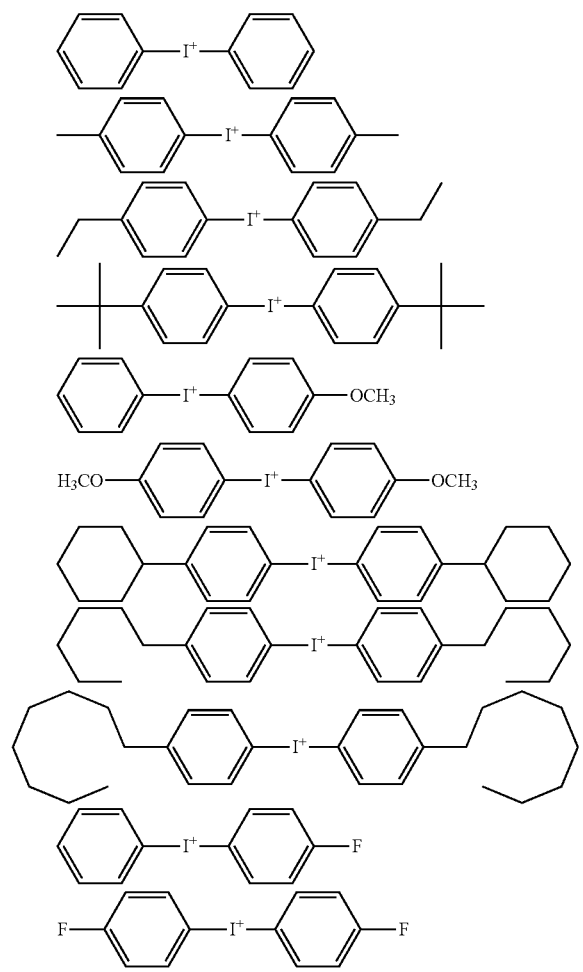
Examples of the ammonium cation having formula (A3) are shown below, but not limited thereto.
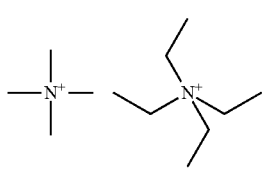
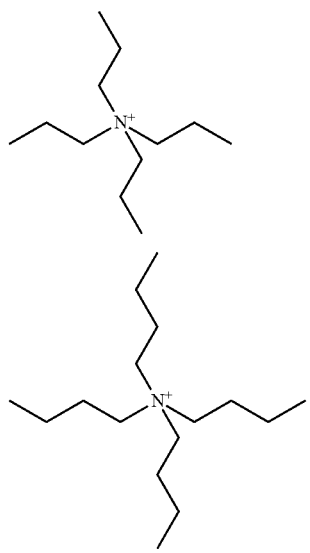
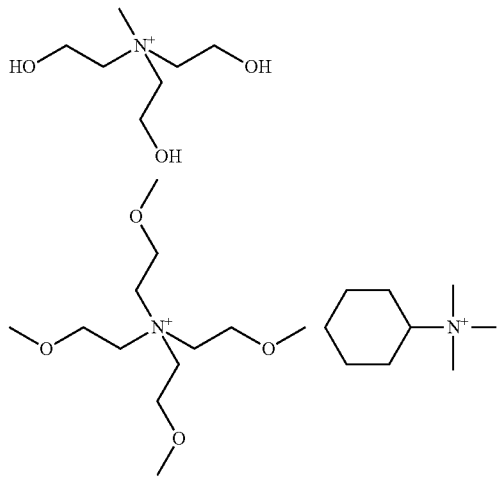
The synthesis of the inventive salt compound is described below, for example, by Scheme A with reference to the embodiment of m=1.
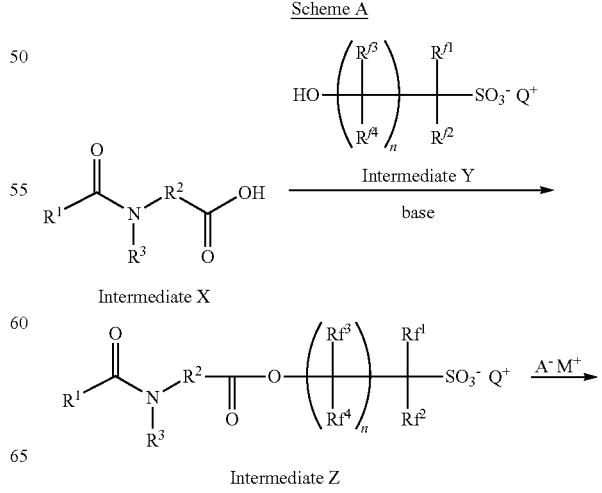

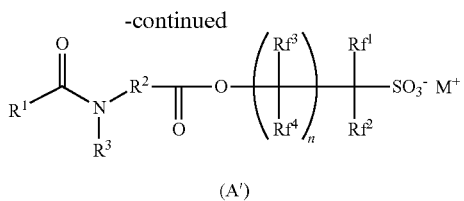

(A')

Herein $R^1$ to $R^3$, $R^{11}$ to $R^{14}$, $M^+$ and n are as defined above, $Q^+$ is a counter cation, and $A^-$ is a counter anion.

The method according to Scheme A intends to synthesize salt compound (A') by condensing Intermediate X with Intermediate Y as starting reactants to form Intermediate Z, and effecting a salt exchange between Intermediate Z and an onium salt: $A^-M^+$.

The first step is to produce Intermediate Z by condensation reaction of Intermediate X with Intermediate Y or alcohol compound. Intermediate X may be a commercial product or synthesized by a well-known method.

In the first step, the carboxyl group on Intermediate X reacts with the hydroxyl group on Intermediate Y to form an ester bond. This reaction may be performed by any well-known organic synthesis method. Specifically, condensation reaction is performed using various condensation agents. Suitable condensation agents include N,N'-dicyclohexylcarbodiimide, N,N'-diisopropylcarbodiimide, 1-[3-(dimethylamino)propyl]-3-ethylcarbodiimide, and 1-ethyl-3-(3-dimethylaminopropyl)carbodiimide hydrochloride. Of these, 1-ethyl-3-(3-dimethylaminopropyl)carbodiimide hydrochloride is preferred because a urea compound formed as by-product is readily removed after the reaction. The reaction is performed by dissolving Intermediate X and Intermediate Y in a halide solvent such as methylene chloride and adding a condensation agent. A reaction catalyst such as 4-dimethylaminopyridine may be added to accelerate the reaction rate. It is desired for higher yields that the reaction time be determined by monitoring the progress of reaction by silica gel thin-layer chromatography (TLC) or the like. The reaction time is usually about 12 hours to about 24 hours. After the reaction is terminated, Intermediate Z may be recovered from the reaction solution by ordinary aqueous work-up. If necessary, it can be purified by any standard technique such as chromatography or recrystallization.

In the second step, a salt exchange is performed between Intermediate Z and an onium salt: $A^-M^+$ to synthesize an onium salt (A'). Preferably $A^-$ is a chloride, bromide or methylsulfate anion, which ensures quantitative progress of the exchange reaction. It is desired for higher yields to monitor the progress of reaction by TLC or the like. Onium salt (A') may be recovered from the reaction mixture by ordinary aqueous work-up. If necessary, it can be purified by any standard technique such as chromatography or recrystallization.

In Scheme A, the ion exchange in the second step may be readily performed by a well-known method, for example, according to the teaching of JP-A 2007-145797.

It is noted that the aforementioned synthesis method is merely exemplary. The synthesis method of the inventive salt compound is not limited thereto.

Chemically Amplified Resist Composition

A further embodiment of the invention is a chemically amplified resist composition comprising (A) a photoacid generator in the form of the salt compound having formula (A) as an essential component, (B) a base resin, and (C) an organic solvent. If necessary, the composition may further comprise:

(D) a quencher,
(E) a photoacid generator other than the salt compound having formula (A), and
(F) a surfactant which is insoluble or substantially insoluble in water and soluble in alkaline developer, and/or a surfactant which is insoluble or substantially insoluble in water and alkaline developer.

In the resist composition, an appropriate amount of the PAG as component (A) is 0.1 to 40 parts by weight, more preferably 1 to 20 parts by weight per 100 parts by weight of the base resin (B). As long as the amount of component (A) is within the range, it exerts a full function of photoacid generator, eliminating any performance degradations including a drop of sensitivity, solubility shortage, and foreign particles. The PAG may be used alone or in admixture of two or more.

(B) Base Resin

The base resin used herein as component (B) preferably contains a polymer comprising recurring units having the formula (a) and recurring units having the formula (b).

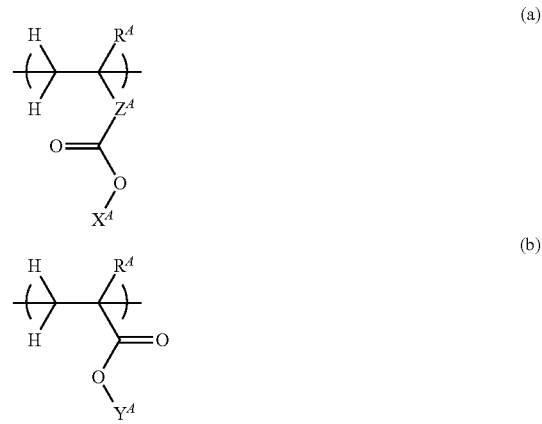

In formulae (a) and (b), $R^A$ is each independently hydrogen, fluorine, methyl or trifluoromethyl. $Z^A$ is a single bond, phenylene group, naphthylene group or (backbone)-C(=O)—O—Z'—, wherein Z' is a $C_1$-$C_{10}$ alkanediyl group which may contain a hydroxyl moiety, ether bond, ester bond or lactone ring, or phenylene group or naphthylene group. $X^A$ is an acid labile group. $Y^A$ is hydrogen or a polar group having at least one structure selected from among hydroxyl, cyano, carbonyl, carboxyl, ether bond, ester bond, sulfonate bond, carbonate bond, lactone ring, sultone ring and carboxylic anhydride.

Examples of the structure having formula (a) wherein $Z^A$ is a variant are shown below. Notably, $R^A$ and $X^A$ are as defined above.

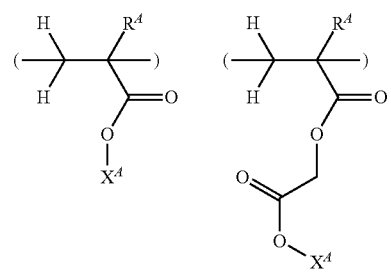

-continued
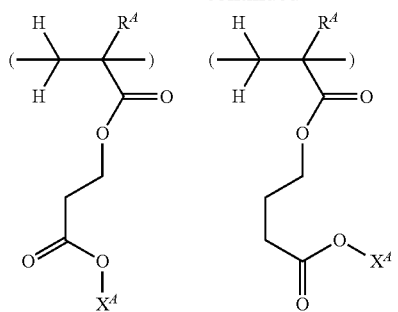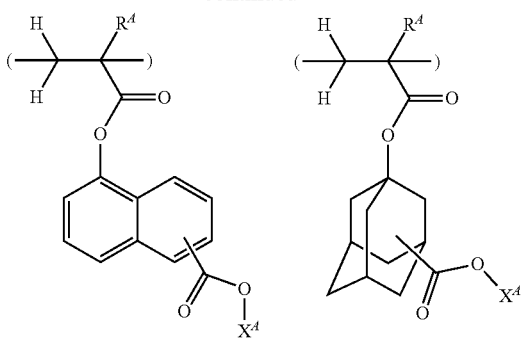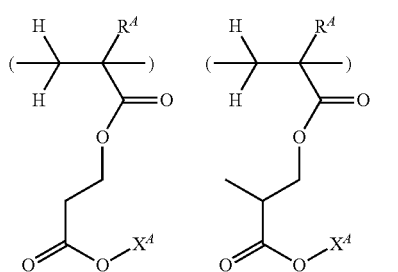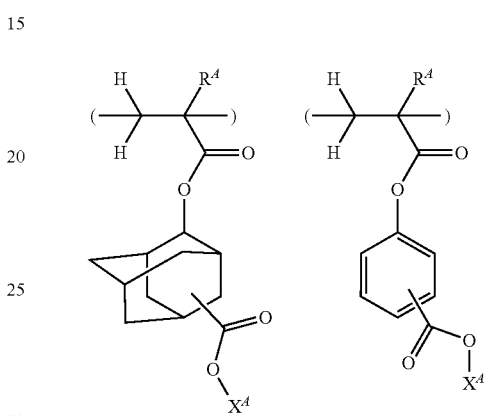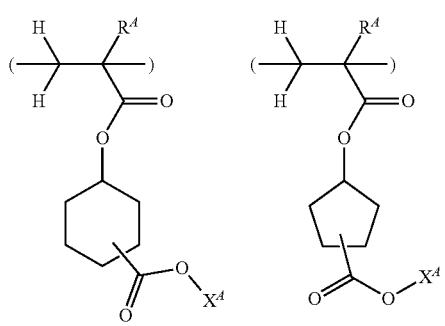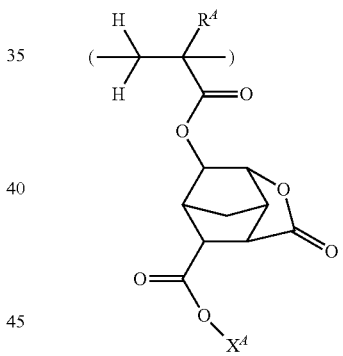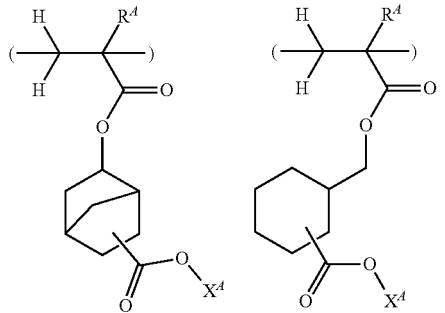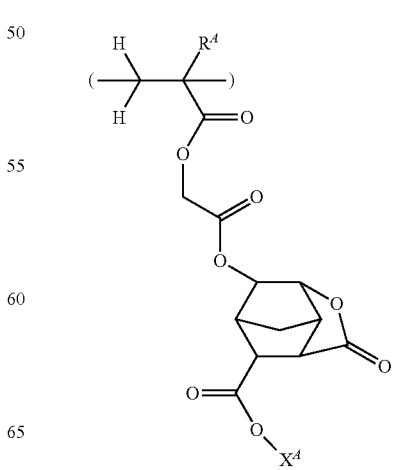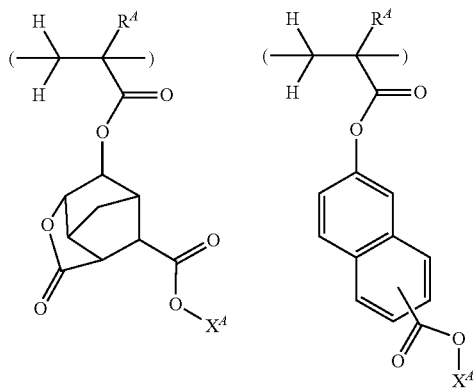

-continued

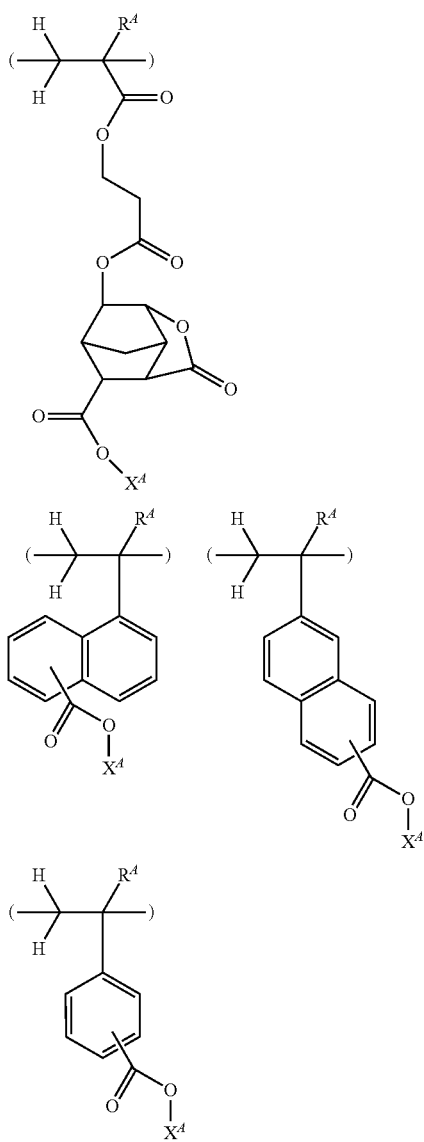

Under the action of acid, a polymer comprising recurring units of formula (a) is decomposed to generate carboxylic acid, turning to be an alkali soluble polymer.

The acid labile group $X^A$ may be selected from a variety of such groups. Examples of the acid labile group include groups of the following formulae (L1) to (L4), $C_4$-$C_{20}$, preferably $C_4$-$C_{15}$ tertiary alkyl groups, trialkylsilyl groups in which each alkyl moiety has 1 to 6 carbon atoms, and $C_4$-$C_{20}$ oxoalkyl groups.

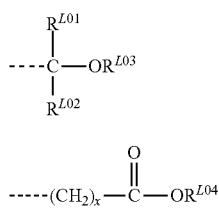

-continued

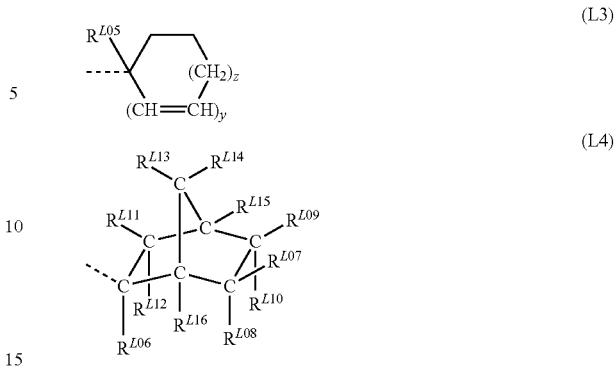

In formula (L1), $R^{L01}$ and $R^{L02}$ each are hydrogen or a $C_1$-$C_{15}$, preferably $C_1$-$C_{10}$ alkyl group. The alkyl group may be straight, branched or cyclic, and examples thereof include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

$R^{L03}$ is a $C_1$-$C_{18}$, preferably $C_1$-$C_{10}$ monovalent hydrocarbon group which may contain a heteroatom such as oxygen. Examples of the monovalent hydrocarbon group include straight, branched or cyclic alkyl groups and substituted forms of such alkyl groups in which some hydrogen is substituted by hydroxyl, alkoxy, oxo, amino, alkylamino or the like, or in which some carbon is replaced by a moiety containing a heteroatom such as oxygen. Suitable alkyl groups are as exemplified above for $R^{L01}$ and $R^{L02}$. Examples of the substituted alkyl groups are shown below.

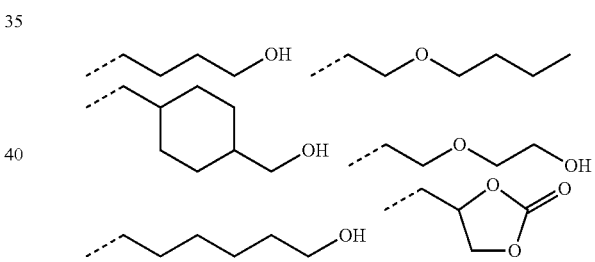

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Ring-forming participants of $R^{L01}$, $R^{L02}$ and $R^{L03}$ represent a $C_1$-$C_{18}$, preferably $C_1$-$C_{10}$ straight or branched alkylene group.

In formula (L2), $R^{L04}$ is a $C_4$-$C_{20}$, preferably $C_4$-$C_{15}$ tertiary alkyl group, a trialkylsilyl group in which each alkyl moiety has 1 to 6 carbon atoms, a $C_4$-$C_{20}$ oxoalkyl group, or a group of formula (L1). Exemplary tertiary alkyl groups include tert-butyl, tert-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups include trimethylsilyl, triethylsilyl, and dimethyl-tert-butylsilyl. Exemplary oxoalkyl groups include 3-oxocyclohexyl, 4-methyl-2-oxooxan-4-yl, and 5-methyl-2-oxooxolan-5-yl. Letter x is an integer of 0 to 6.

In formula (L3), $R^{L05}$ is a substituted or unsubstituted $C_1$-$C_8$ alkyl group or a substituted or unsubstituted $C_6$-$C_{20}$ aryl group. The optionally substituted alkyl group may be straight, branched or cyclic and examples thereof include straight, branched or cyclic alkyl groups such as methyl, ethyl, propyl, isopropyl, n-butyl, sec-butyl, tert-butyl, tert-pentyl, n-pentyl, n-hexyl, cyclopentyl, and cyclohexyl, and substituted forms of such groups in which some hydrogen is substituted by hydroxyl, alkoxy, carboxyl, alkoxycarbonyl, oxo, amino, alkylamino, cyano, mercapto, alkylthio, sulfo or the like.

Examples of the optionally substituted aryl groups include phenyl, methylphenyl, naphthyl, anthryl, phenanthryl, and pyrenyl, and substituted forms of such groups in which some hydrogen is substituted by hydroxyl, alkoxy, carboxyl, alkoxycarbonyl, oxo, amino, alkylamino, cyano, mercapto, alkylthio, sulfo or the like. Letter y is equal to 0 or 1, z is an integer of 0 to 3, and 2y+z is equal to 2 or 3.

In formula (L4), $R^{L06}$ is a substituted or unsubstituted $C_1$-$C_8$ alkyl group or a substituted or unsubstituted $C_6$-$C_{20}$ aryl group. Examples of these groups are the same as exemplified for $R^{L05}$.

$R^{L07}$ to $R^{L16}$ independently represent hydrogen or $C_1$-$C_{15}$ monovalent hydrocarbon groups. Exemplary hydrocarbon groups include straight, branched or cyclic alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen is substituted by hydroxyl, alkoxy, carboxyl, alkoxycarbonyl, oxo, amino, alkylamino, cyano, mercapto, alkylthio, sulfo or the like. Alternatively, two of $R^{L07}$ to $R^{L16}$, taken together, form a ring with the carbon atom to which they are attached (for example, a pair of $R^{L07}$ and $R^{L08}$, $R^{L07}$ and $R^{L09}$ $R^{L07}$ and $R^{L10}$, $R^{L08}$ and $R^{L10}$, $R^{L09}$ and $R^{L10}$, $R^{L11}$ and $R^{L12}$, or $R^{L13}$ and $R^{L14}$ form a ring). Ring-forming participants of $R^{L07}$ to $R^{L16}$ represent a $C_1$-$C_{15}$ divalent hydrocarbon group, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or $R^{L14}$ and $R^{L15}$).

Of the acid labile groups of formula (L1), the straight and branched ones are exemplified by the following groups.

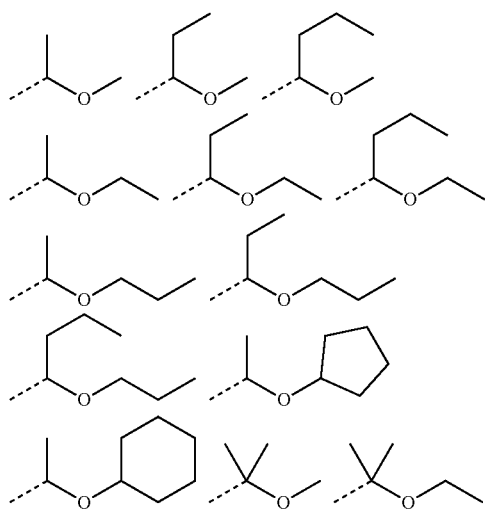

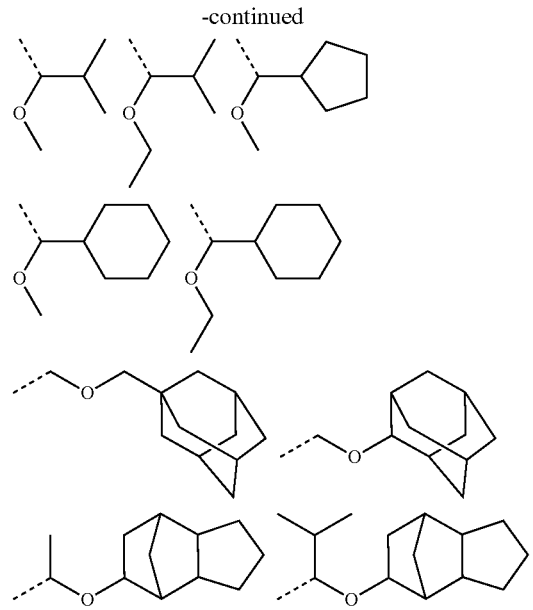

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups having formula (L4), groups having the following formulas (L4-1) to (L4-4) are preferred.

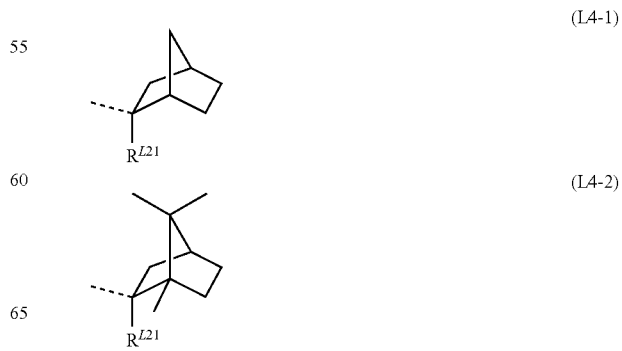

(L4-3)

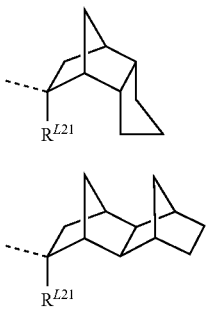

(L4-4)

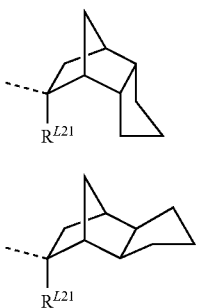

In formulas (L4-1) to (L4-4), the broken line denotes a bonding site and direction. $R^{L21}$ is each independently a monovalent hydrocarbon group. The monovalent hydrocarbon group may be straight, branched or cyclic, and examples thereof include $C_1$-$C_{10}$ alkyl groups such as methyl, ethyl, propyl, isopropyl, n-butyl, sec-butyl, tert-butyl, tert-pentyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. When $X^A$ is an acid labile group of formula (L4), a plurality of stereoisomers may be contained.

For example, the formula (L4-3) represents one or a mixture of two selected from groups having the following formulas (L4-3-1) and (L4-3-2).

(L4-3-1)

(L4-3-2)

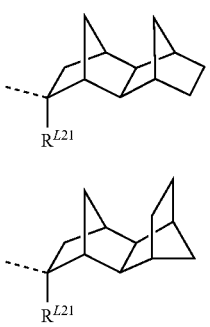

Herein $R^{L21}$ is as defined above.

Similarly, the formula (L4-4) represents one or a mixture of two or more selected from groups having the following formulas (L4-4-1) to (L4-4-4).

(L4-4-1)

(L4-4-2)

(L4-4-3)

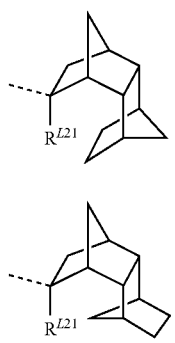

(L4-4-4)

Herein $R^{L21}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)

(L4-2-endo)

(L4-3-endo)

(L4-4-endo)

Herein $R^{L21}$ is as defined above.

Illustrative examples of the acid labile group of formula (L4) are given below, but not limited thereto.

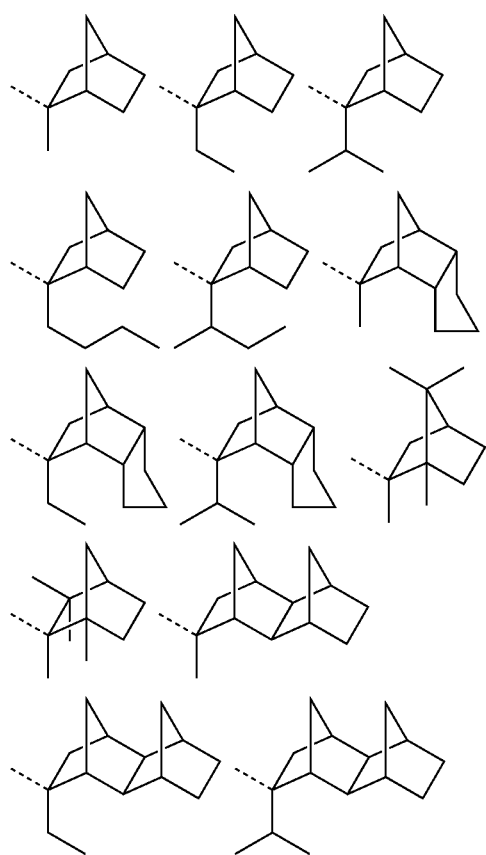
Examples of the $C_4$-$C_{20}$ tertiary alkyl group, trialkylsilyl group in which each alkyl moiety has 1 to 6 carbon atoms, and $C_4$-$C_{20}$ oxoalkyl group, represented by $X^A$, are as exemplified above for $R^{L04}$.
Illustrative examples of the recurring units of formula (a) are given below, but not limited thereto. Herein $R^A$ is as defined above.
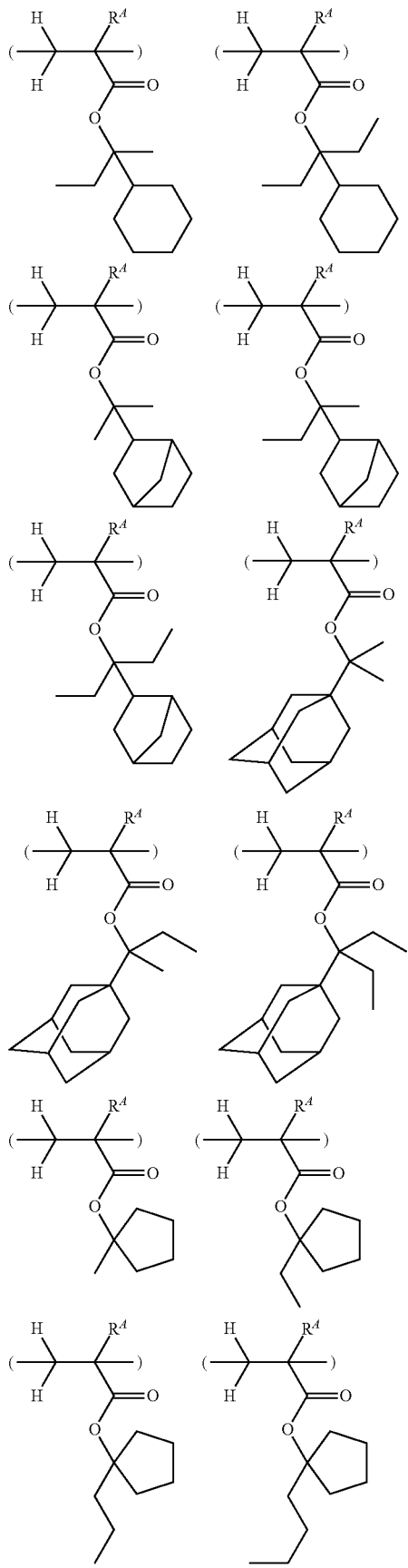

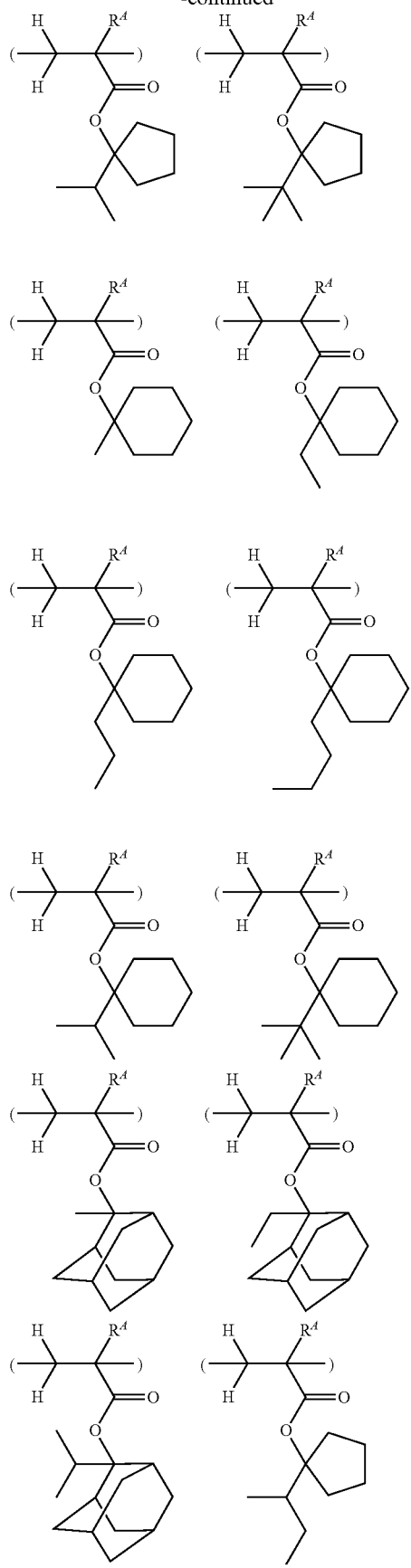

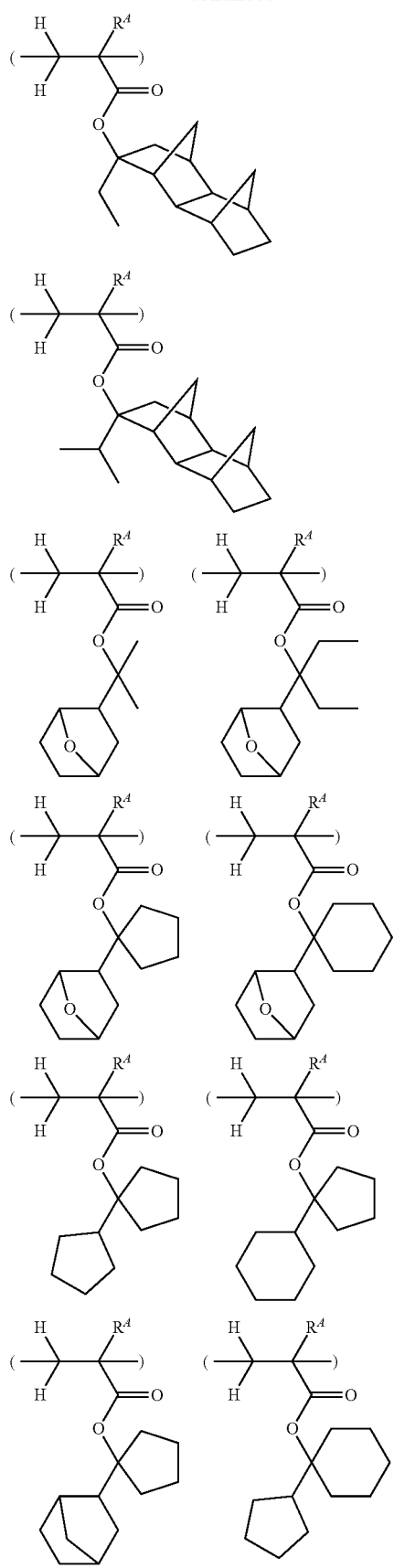
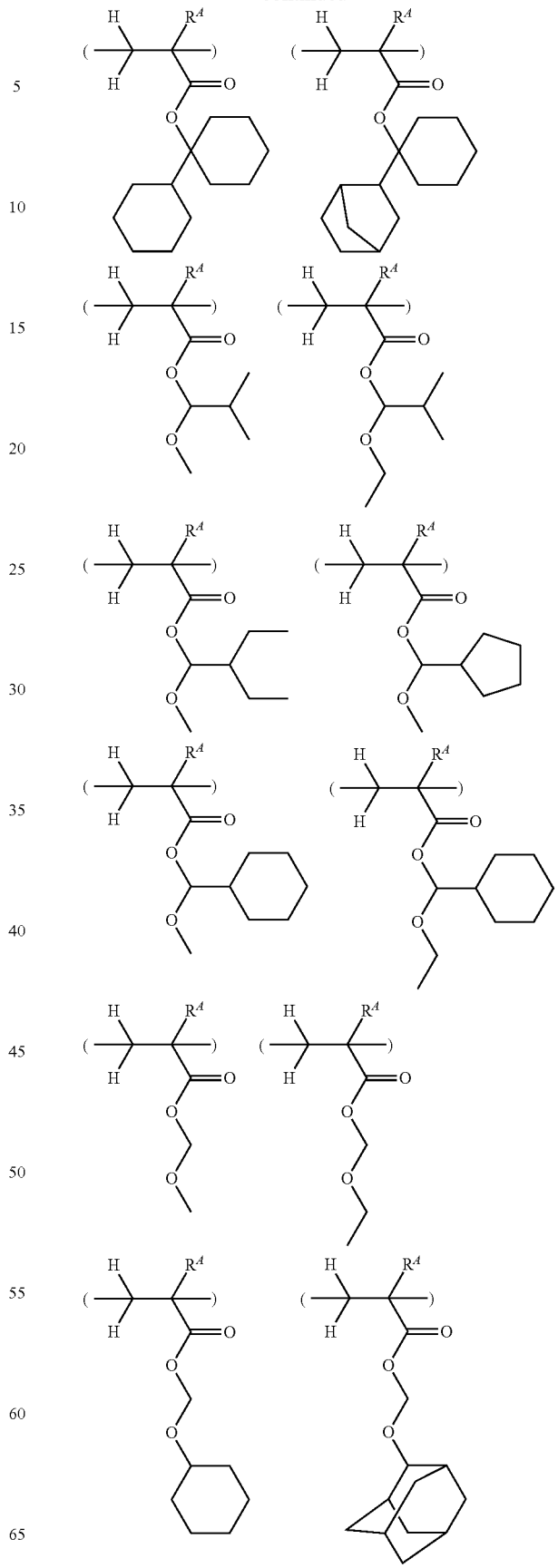

-continued

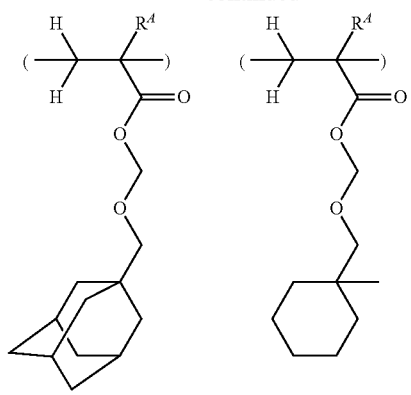

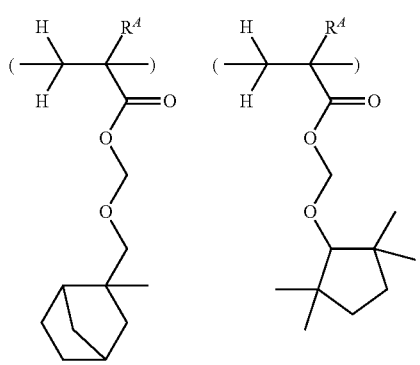

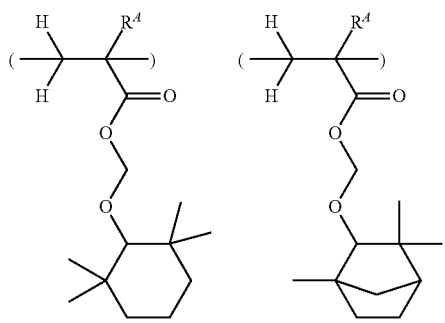

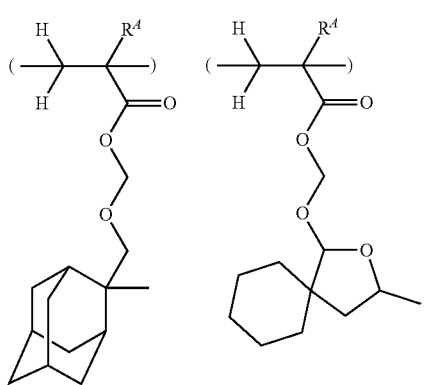

-continued

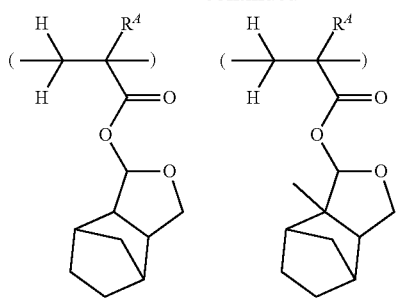

While the foregoing examples correspond to those units wherein $Z^A$ is a single bond, $Z^A$ which is other than a single bond may be combined with similar acid labile groups. Examples of units wherein $Z^A$ is other than a single bond are substantially the same as illustrated above.

Illustrative, non-limiting examples of the recurring units having formula (b) are shown below. Herein $R^A$ is as defined above.

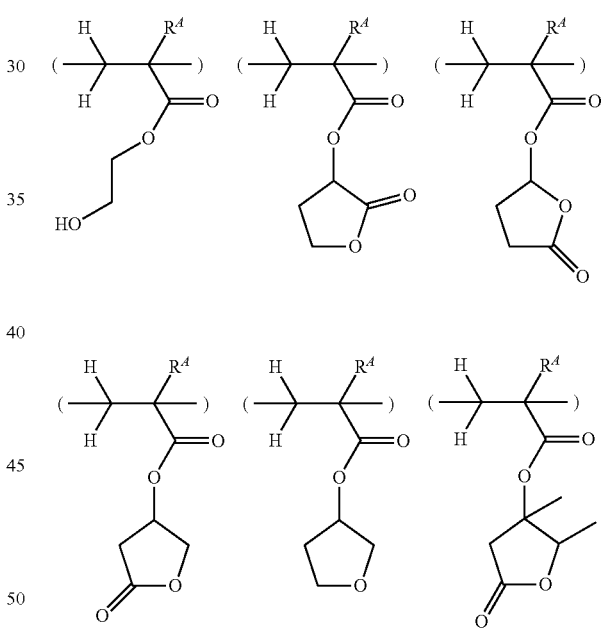

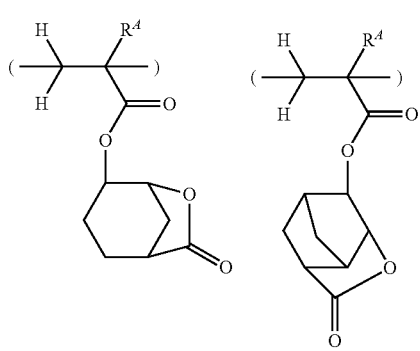

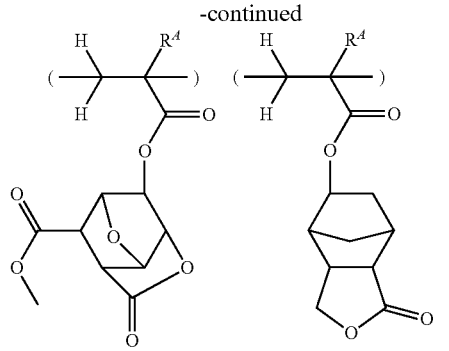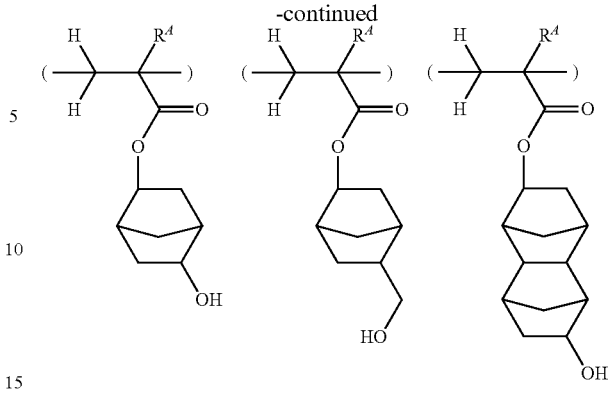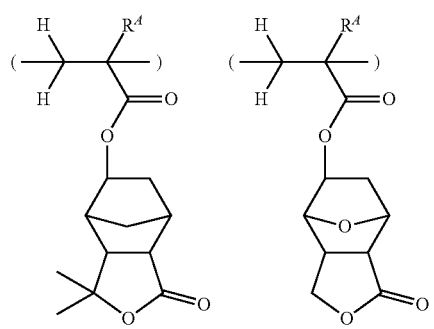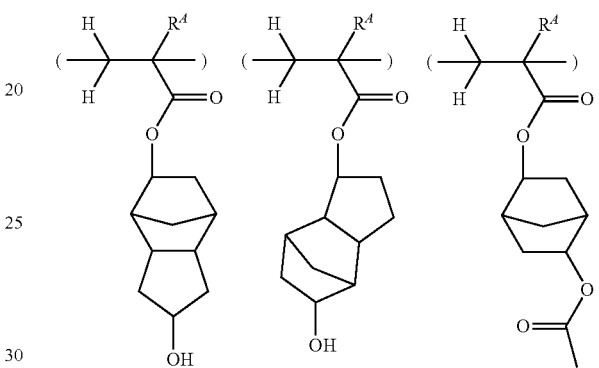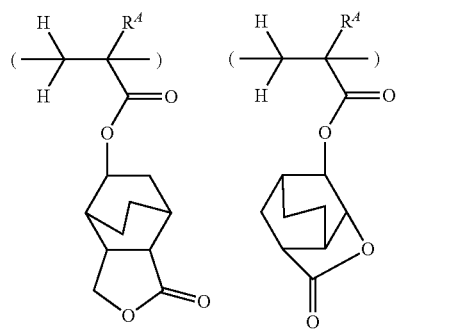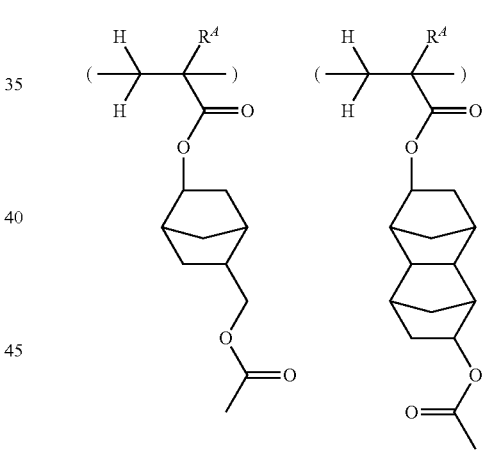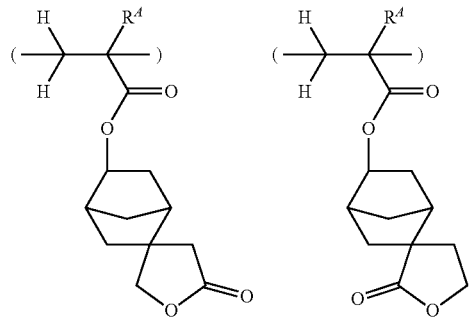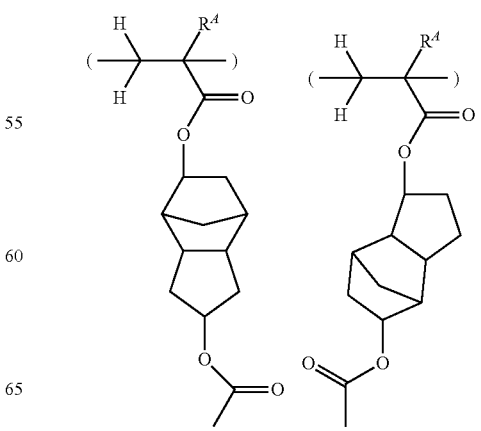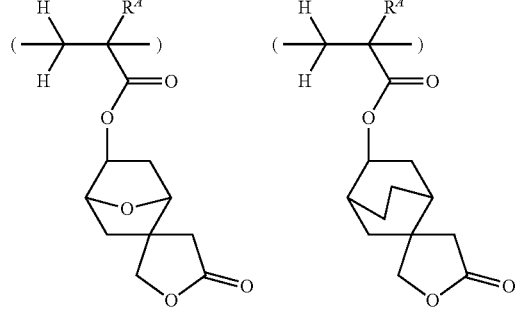

61
-continued
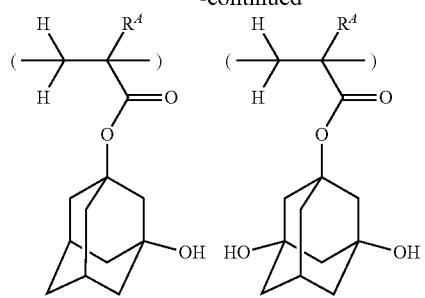
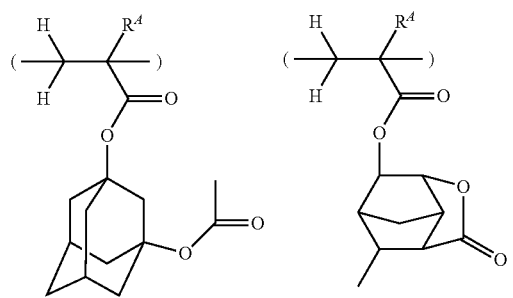
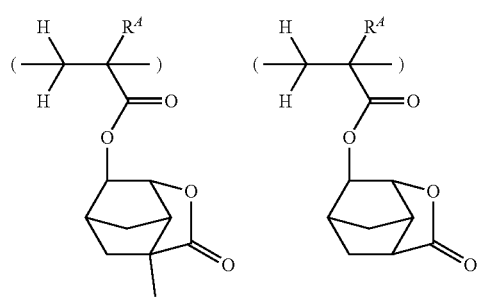
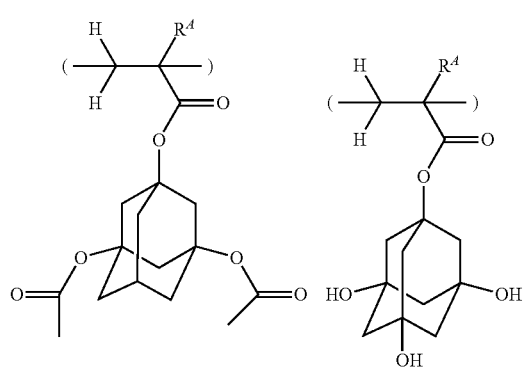
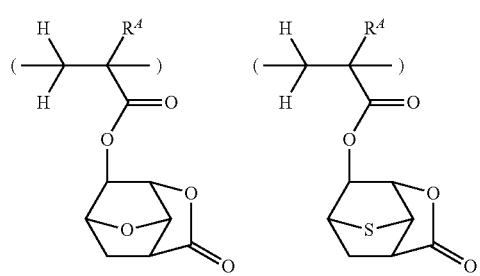
62
-continued
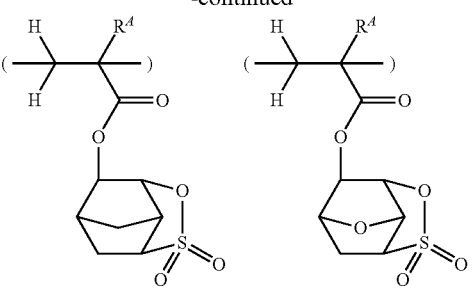
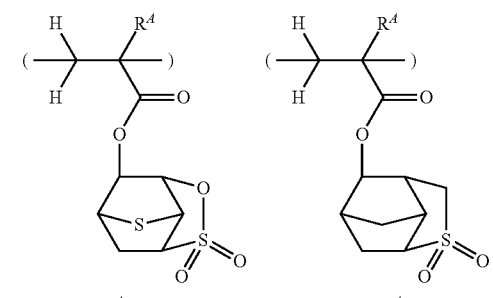
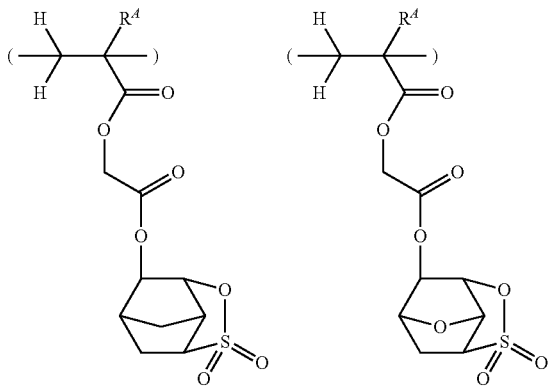
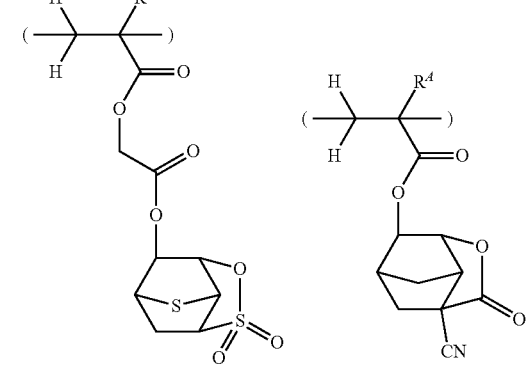
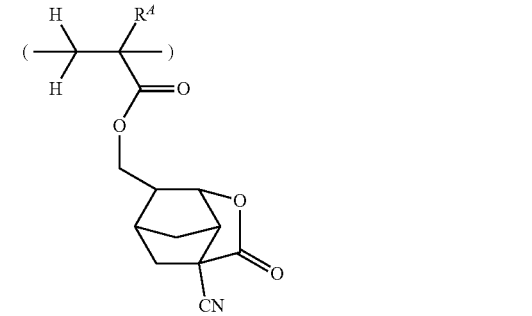

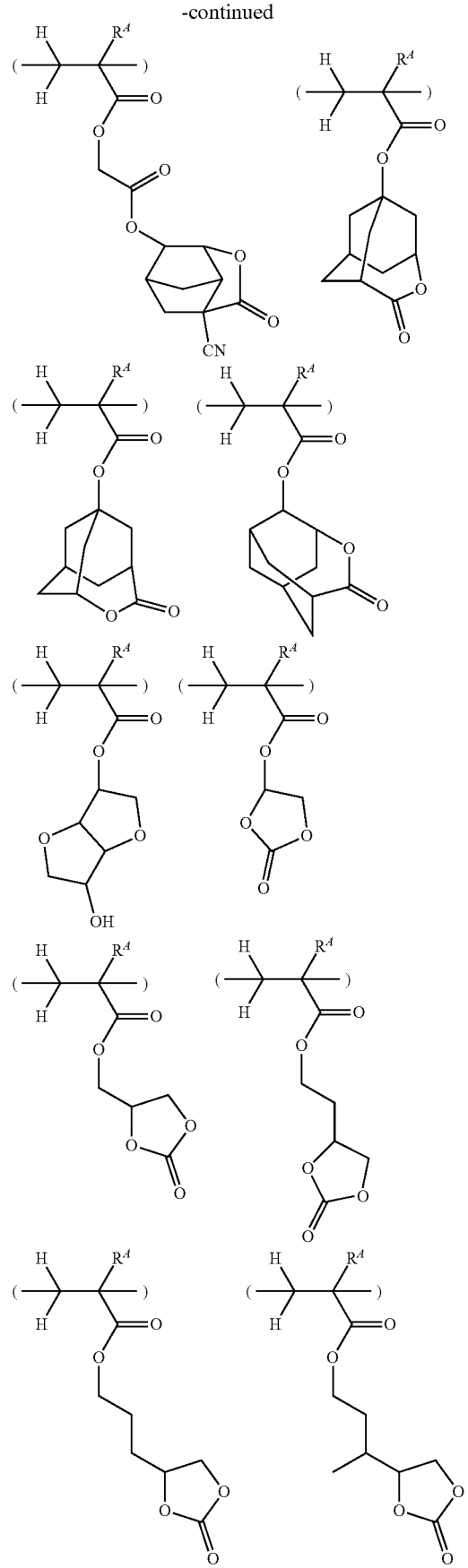
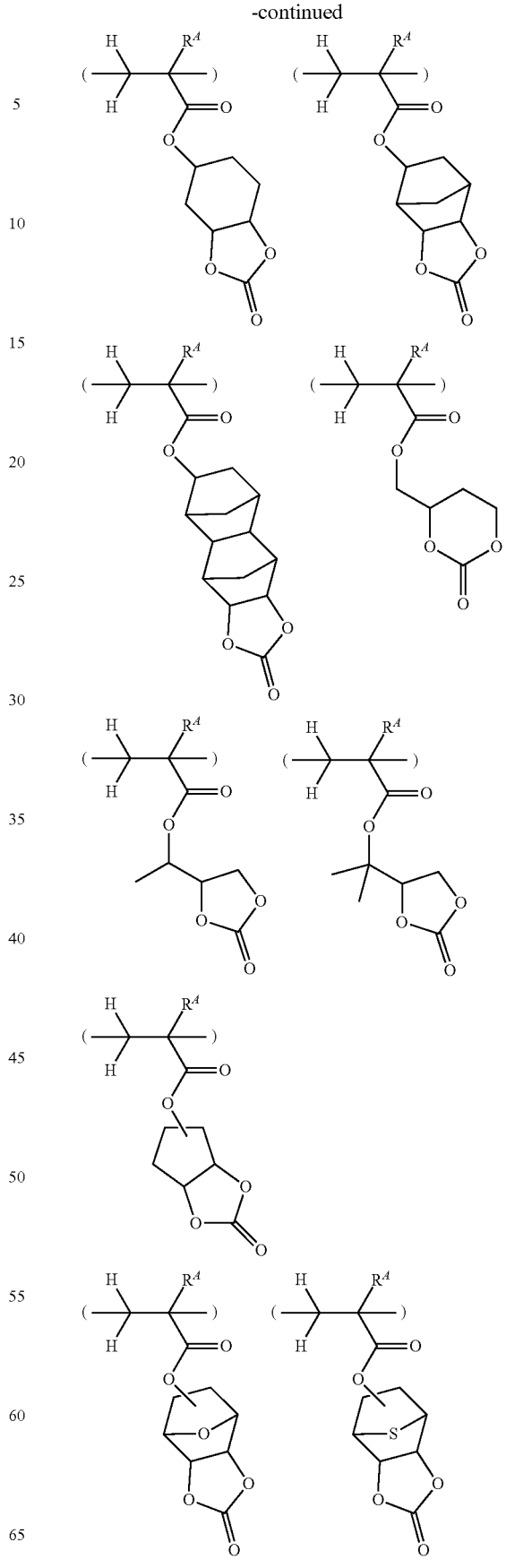

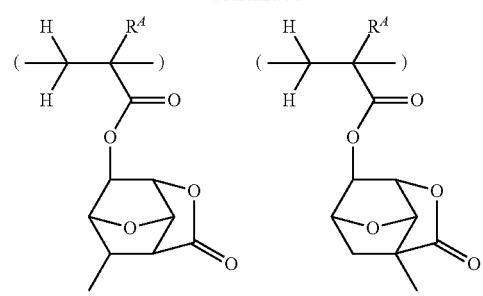
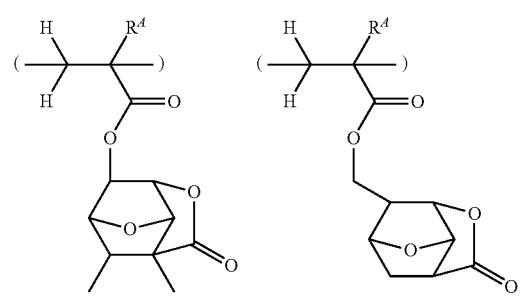
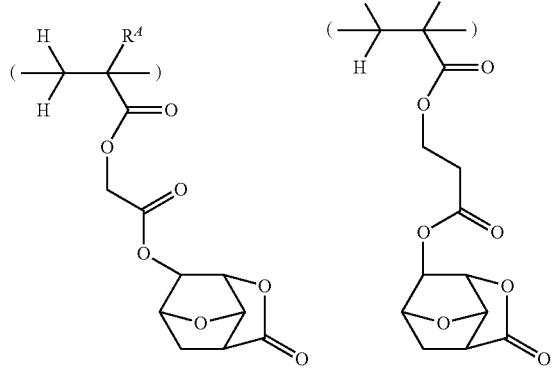
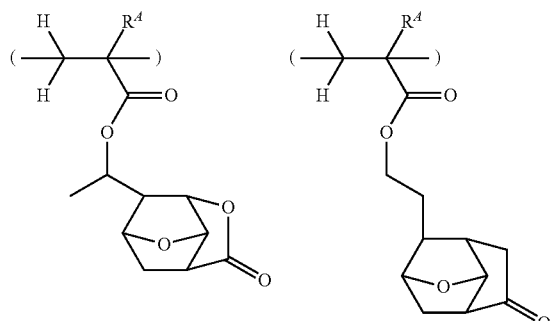
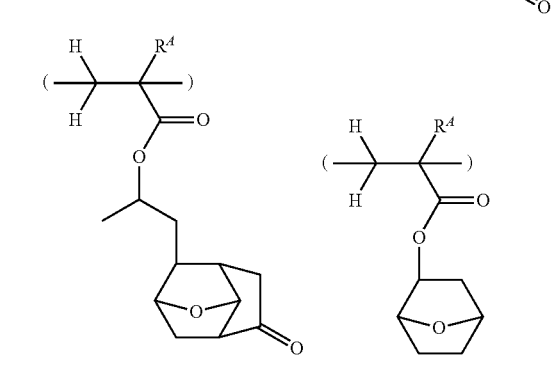
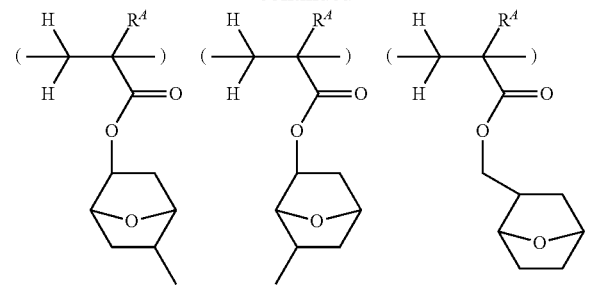
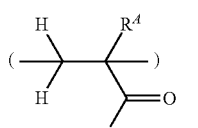
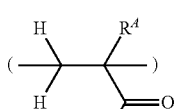
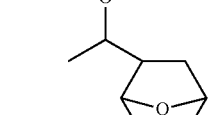
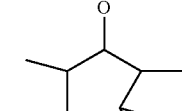
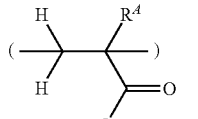
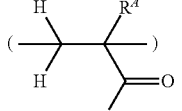
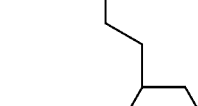
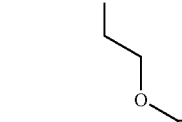
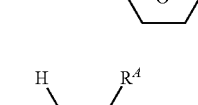
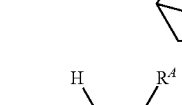
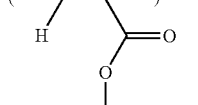
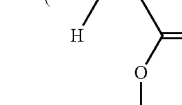
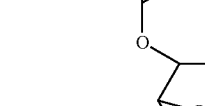
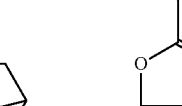
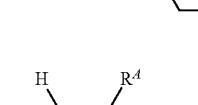
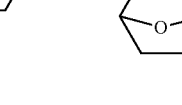
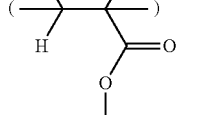
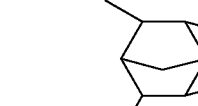
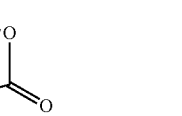
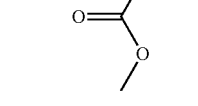

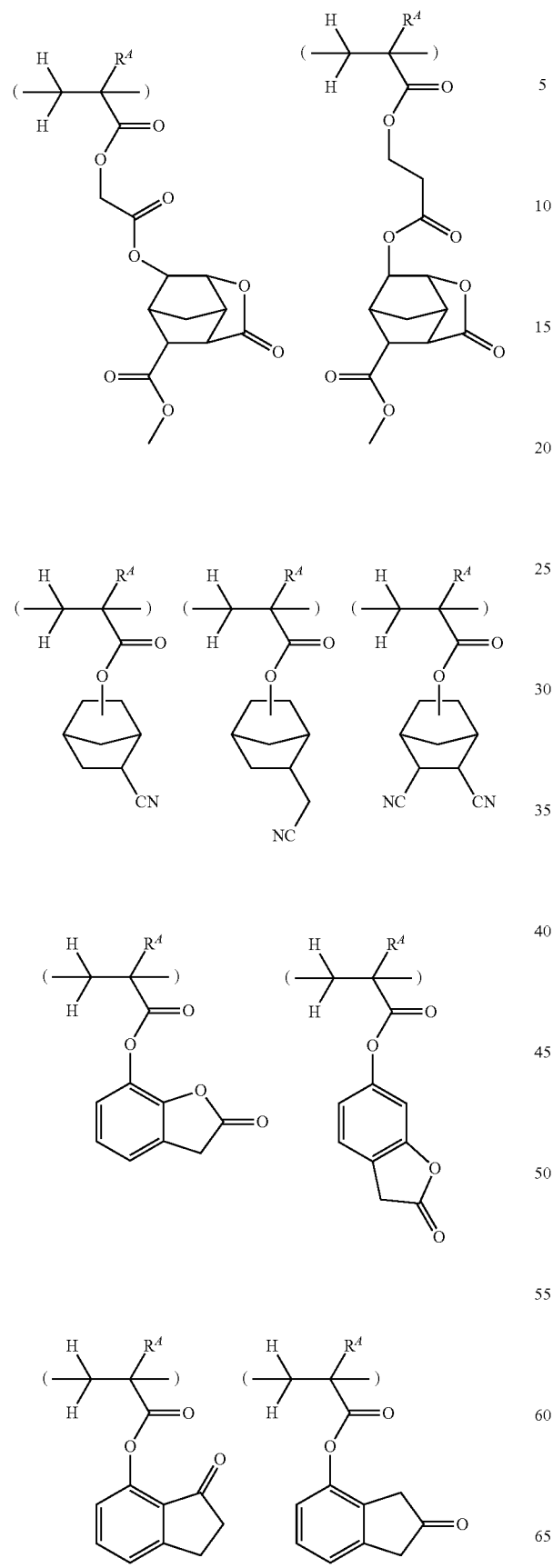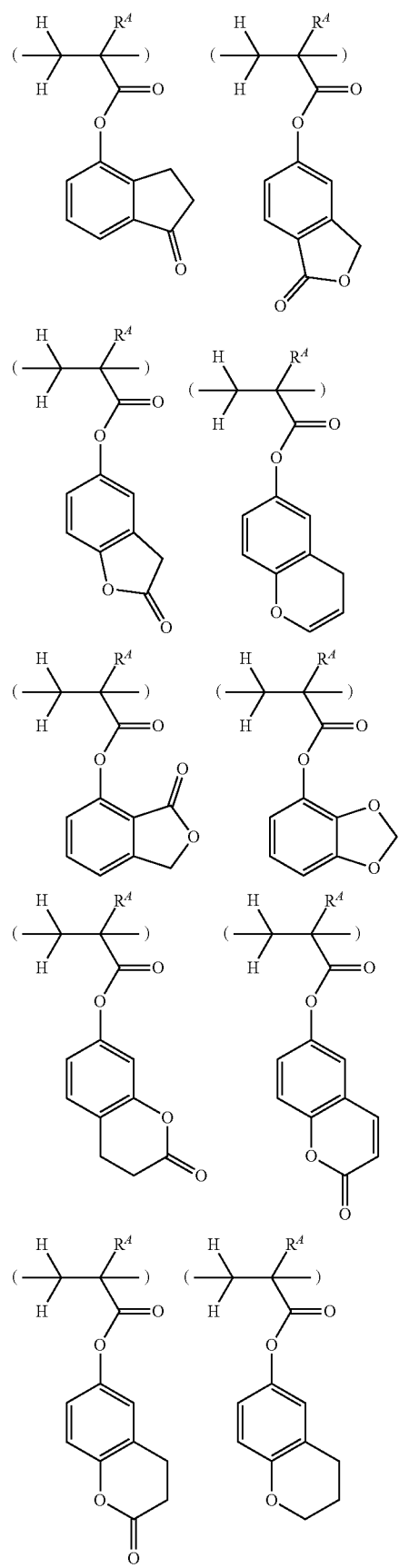

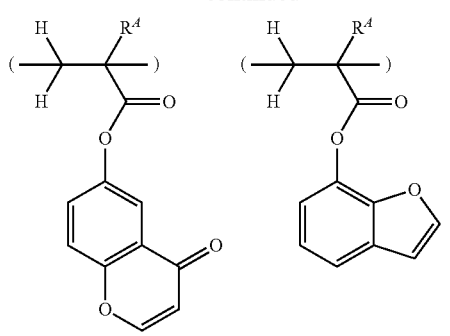
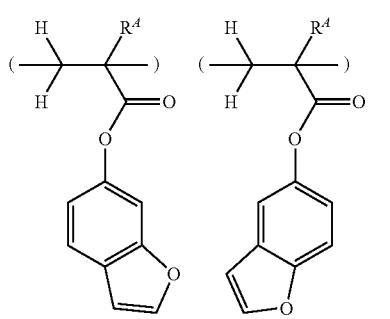
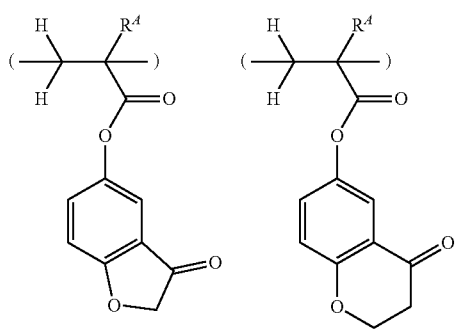
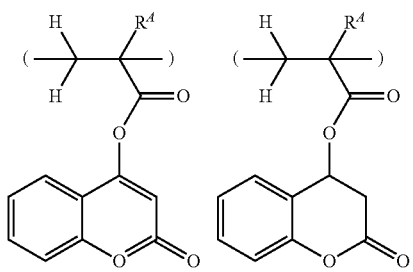
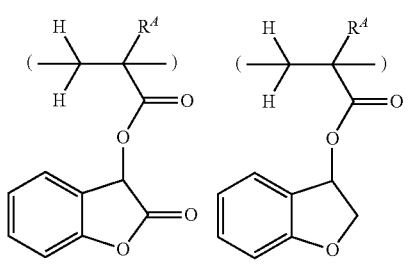
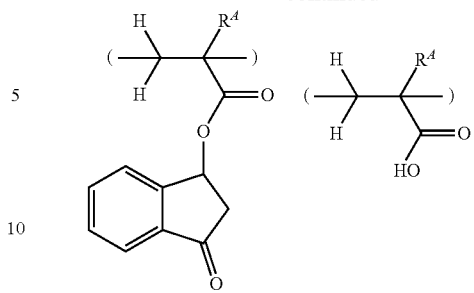
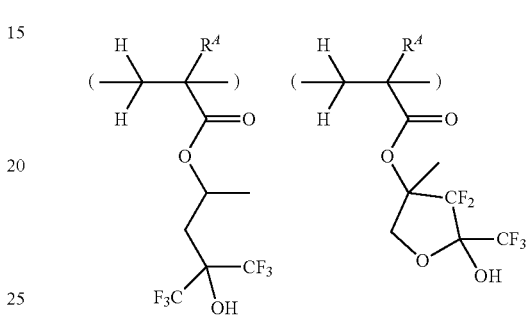
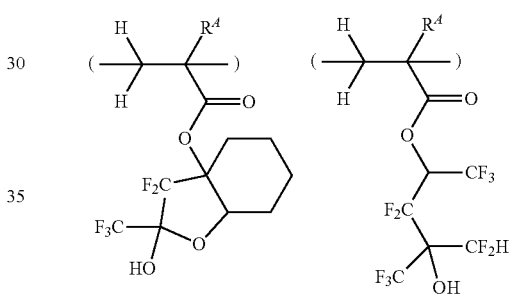
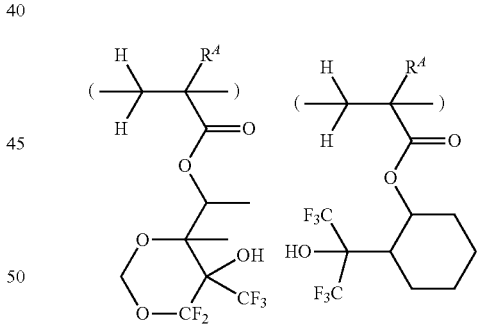
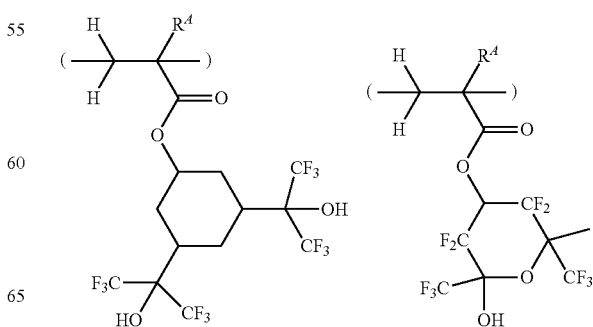

-continued
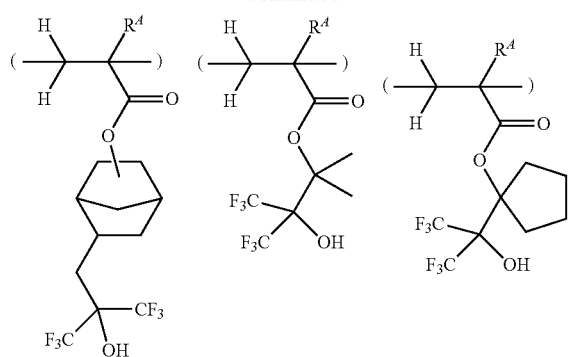
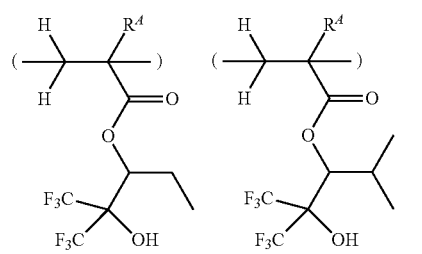
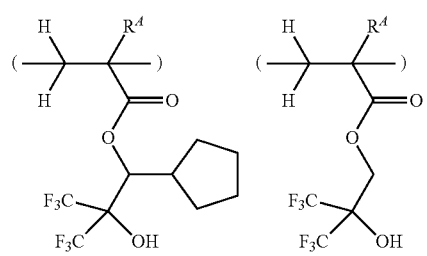
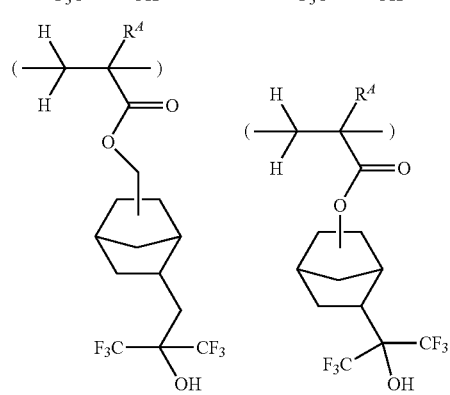
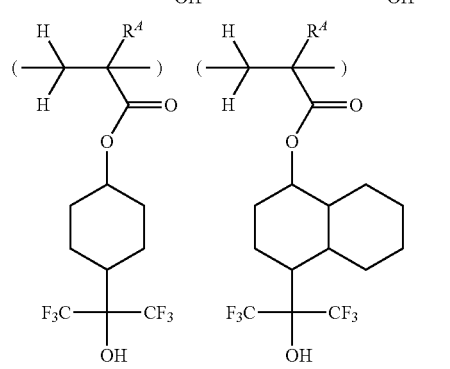
-continued
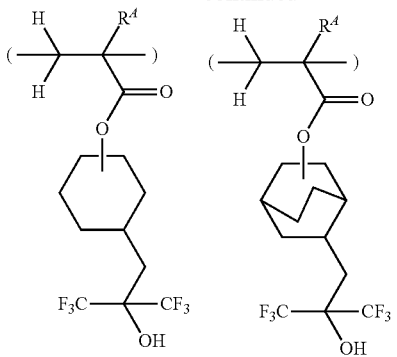
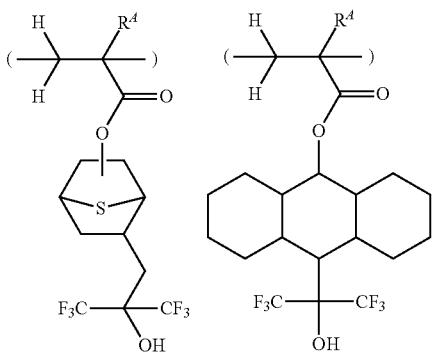
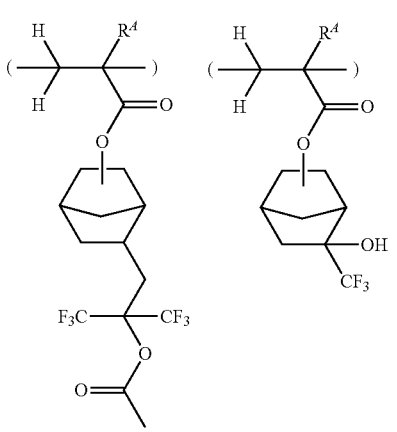
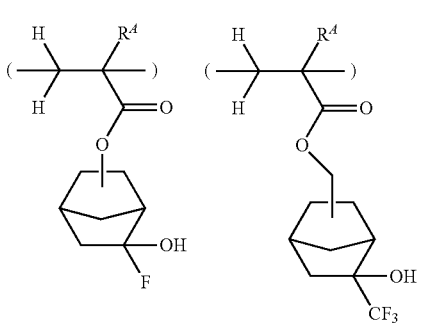

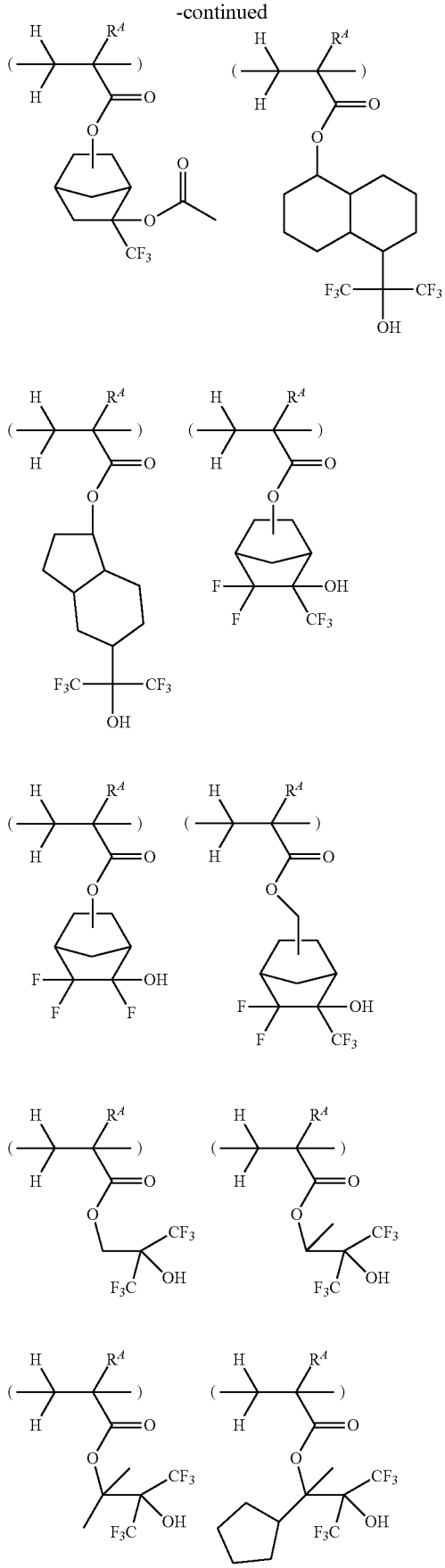
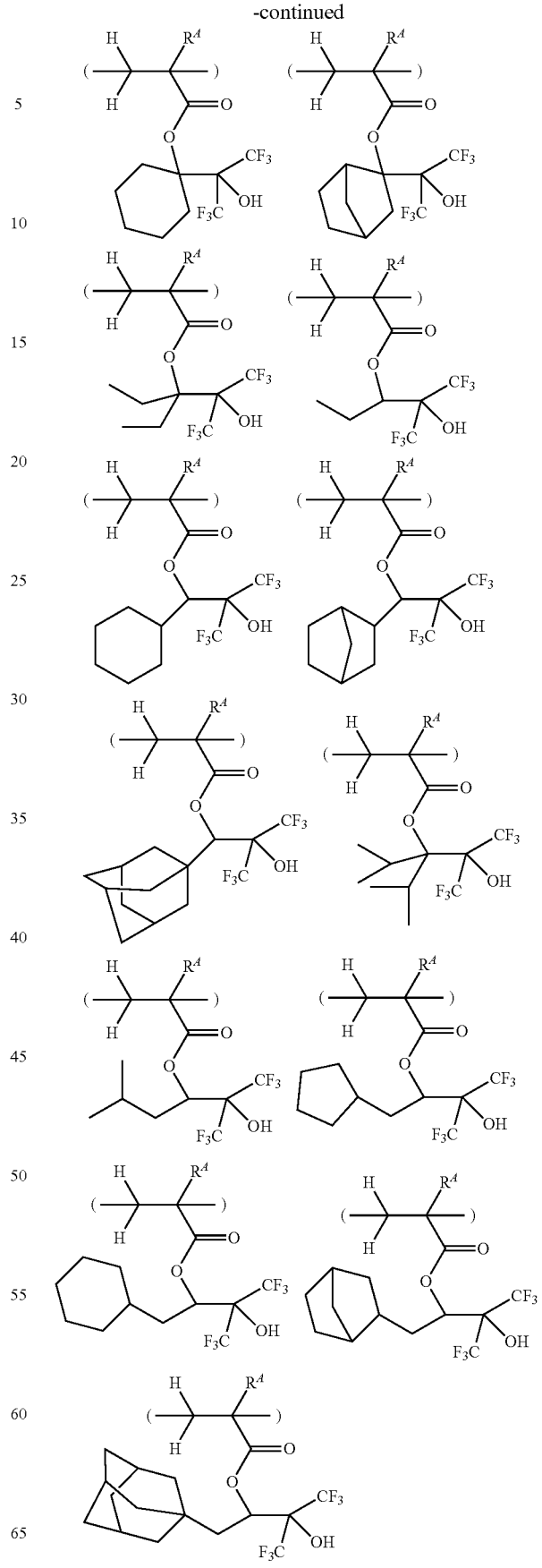

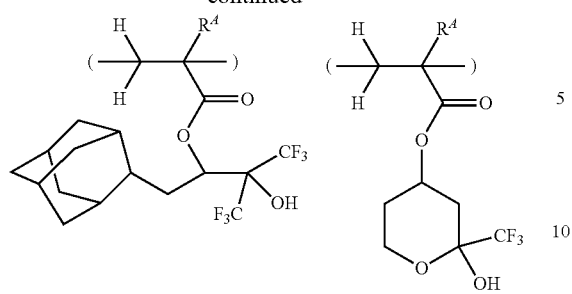
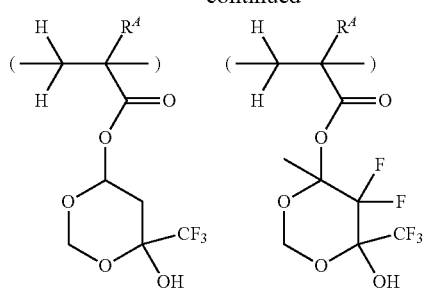
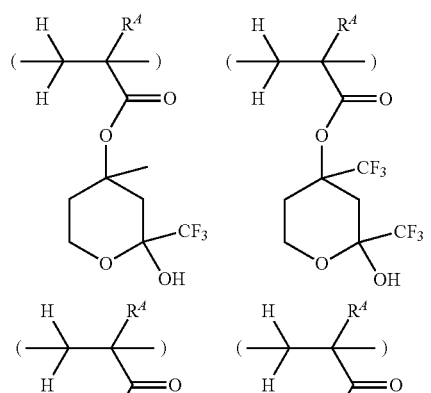
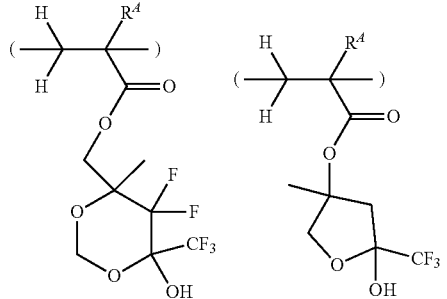
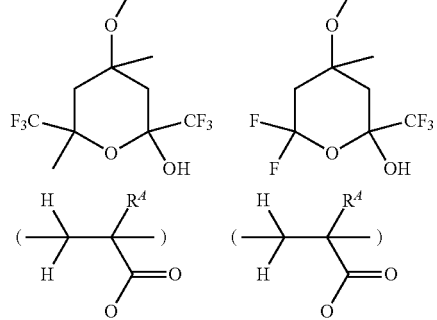
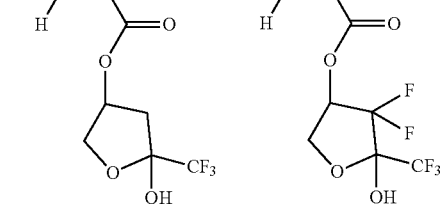
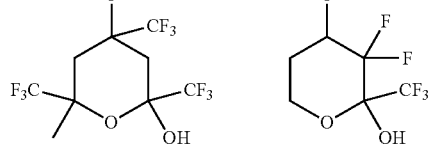
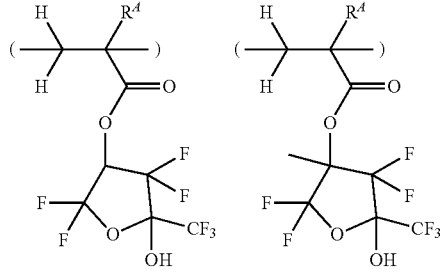
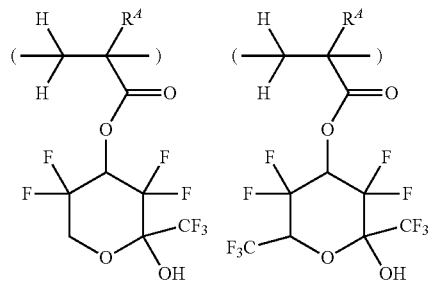
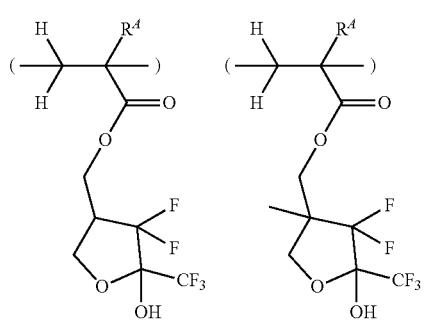
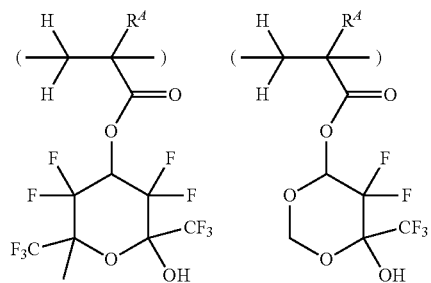

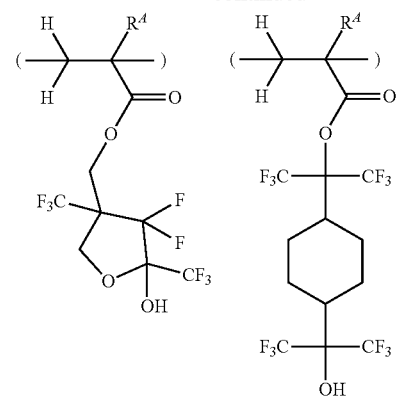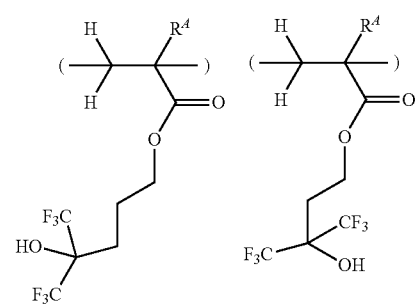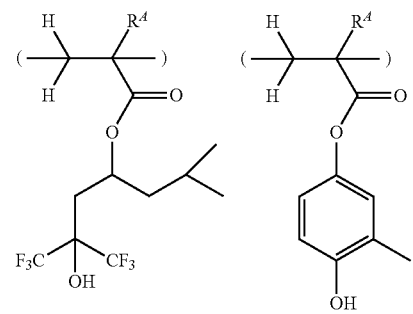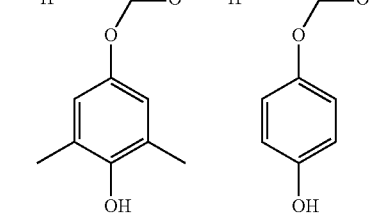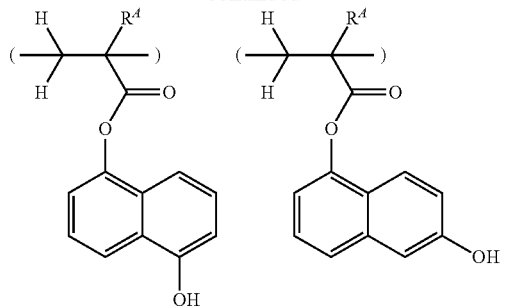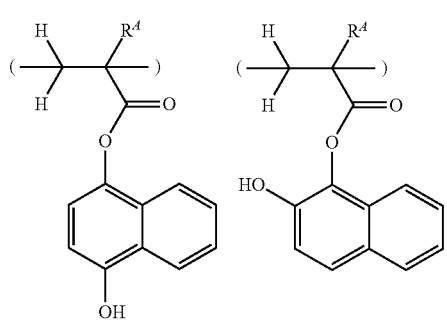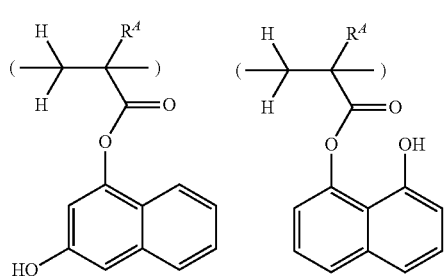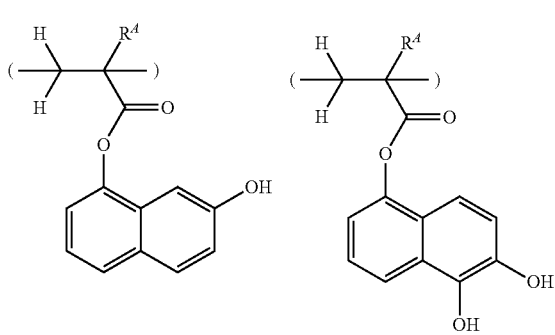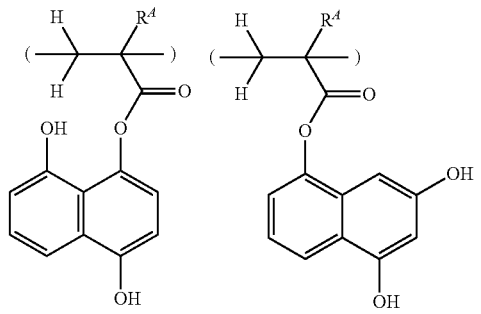

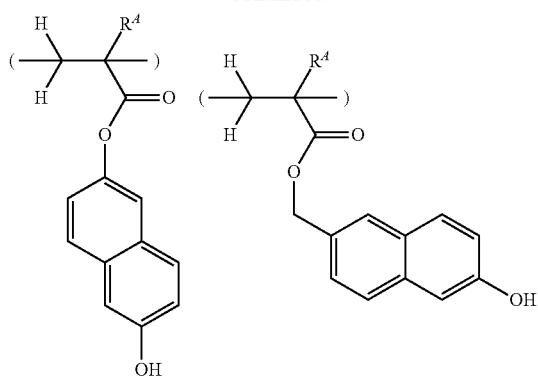
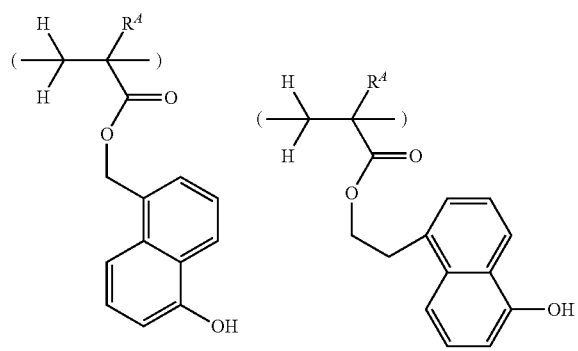
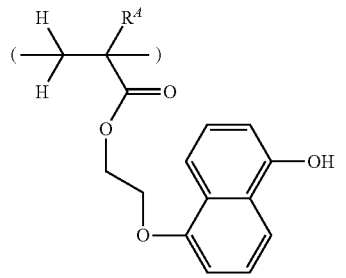
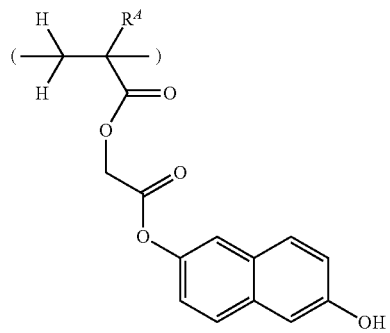
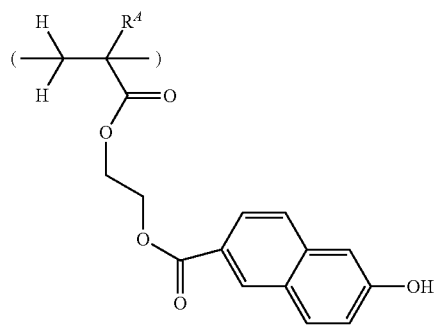

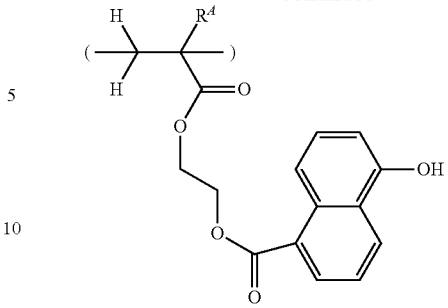

Of the recurring units having formula (b), those units having a lactone ring as the polar group are most preferred.

The polymer may further comprise recurring units of the structure having a hydroxyl group protected with an acid labile group. The recurring unit of the structure having a hydroxyl group protected with an acid labile group is not particularly limited as long as it has one or more protected hydroxyl-bearing structure such that the protective group may be decomposed to generate a hydroxyl group under the action of acid. Inter alia, recurring units having the formula (c1) are preferred.

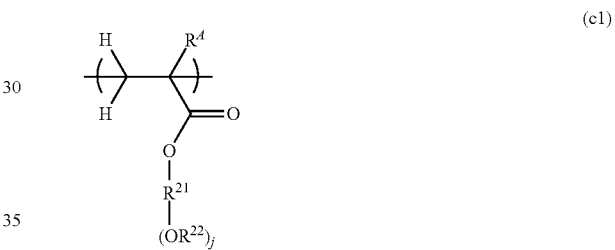

(c1)

In formula (c1), $R^A$ is as defined above, $R^{21}$ is a $C_1$-$C_{30}$ (j+1)-valent hydrocarbon group which may contain a heteroatom. The hydrocarbon group may be straight, branched or cyclic. $R^{22}$ is an acid labile group, and j is an integer of 1 to 4.

Examples of the recurring unit of formula (c1) are shown below, but not limited thereto. Herein $R^A$ and $R^{22}$ are as defined above.

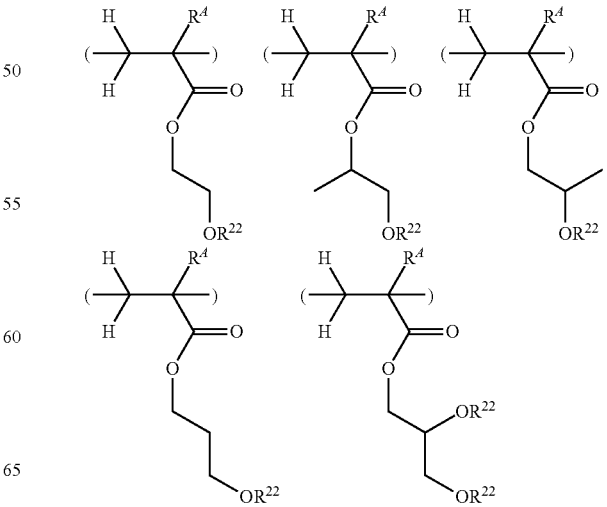

-continued
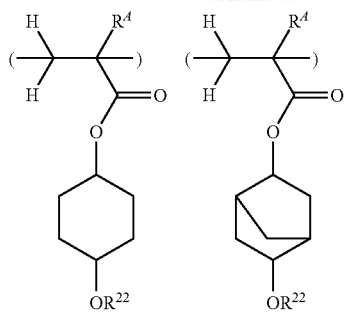
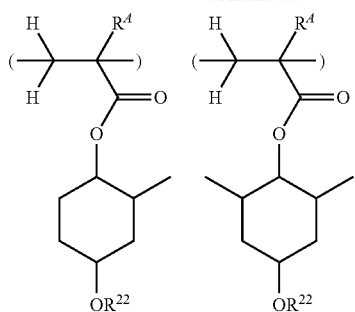
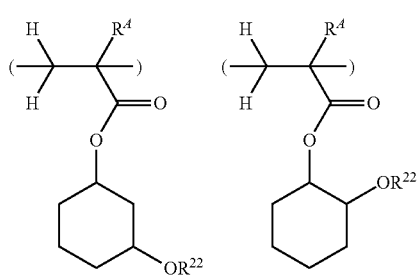
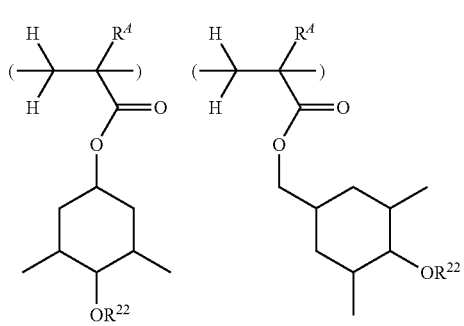
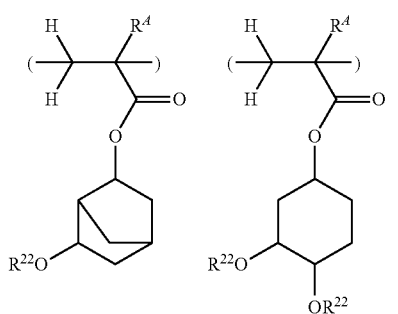
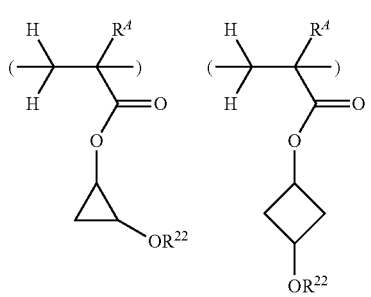
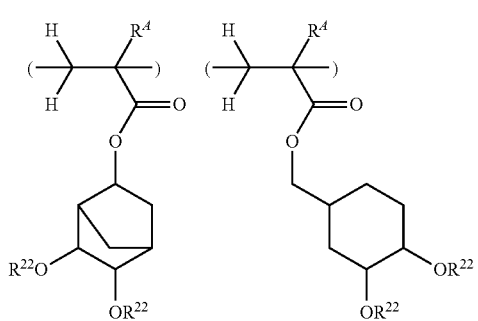
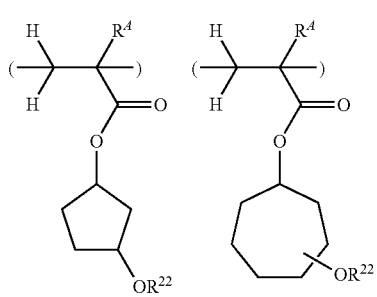
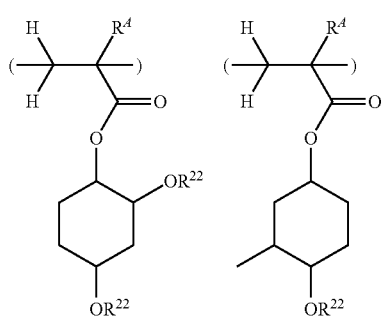
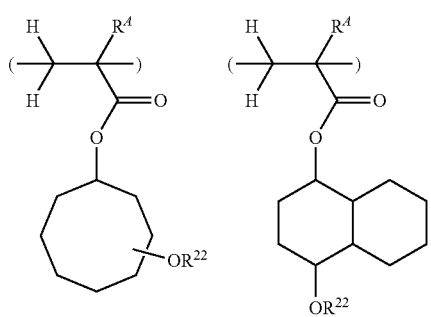

-continued
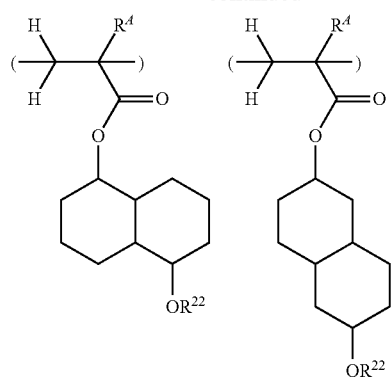
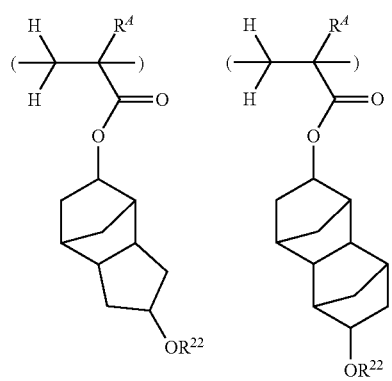
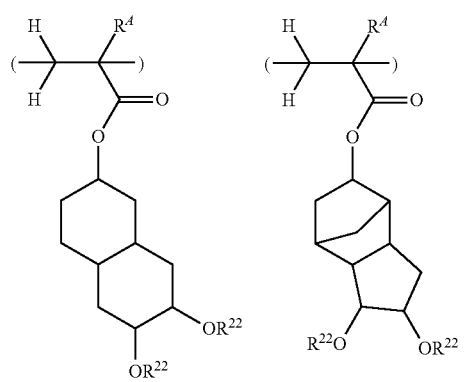
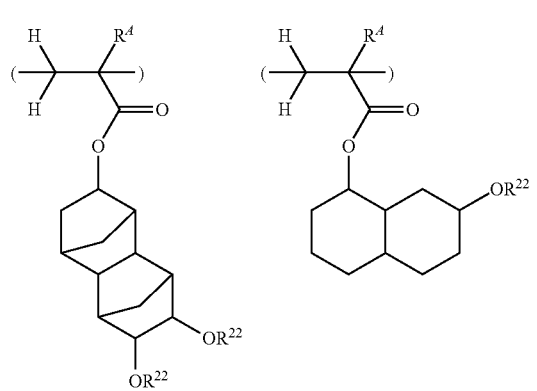
-continued
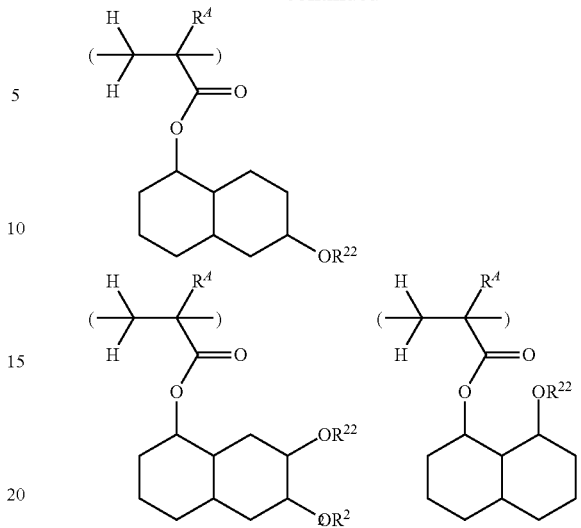
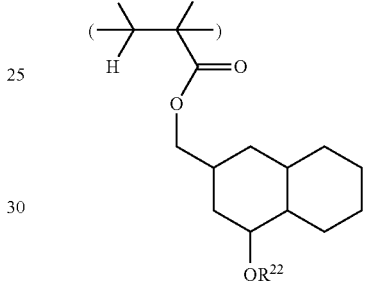
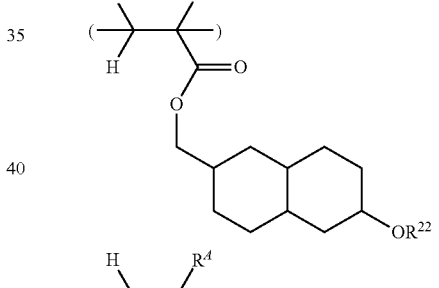
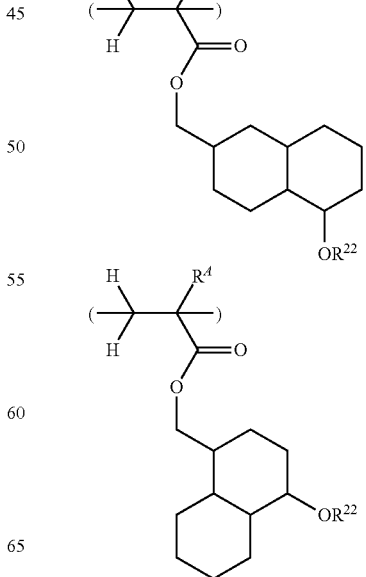

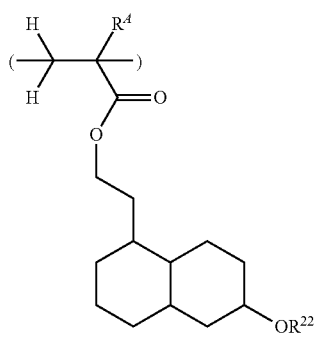
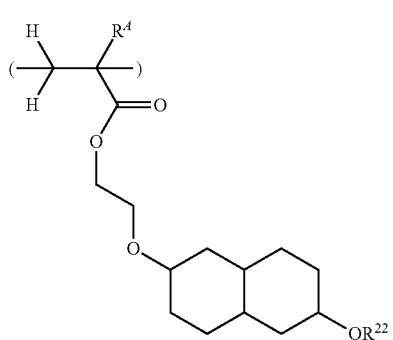
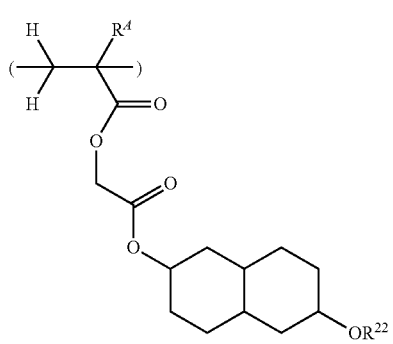
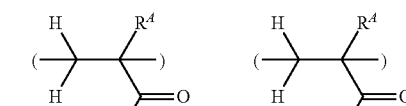
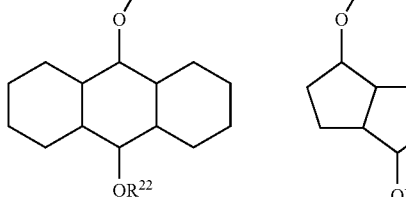
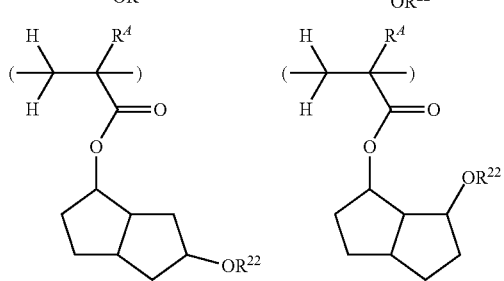
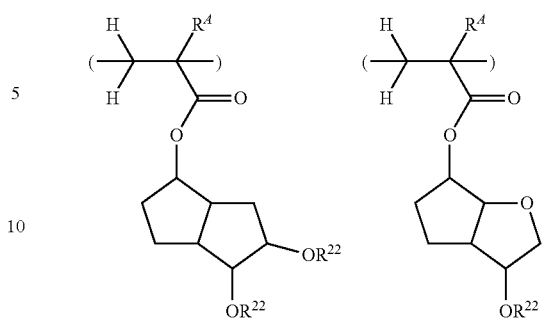
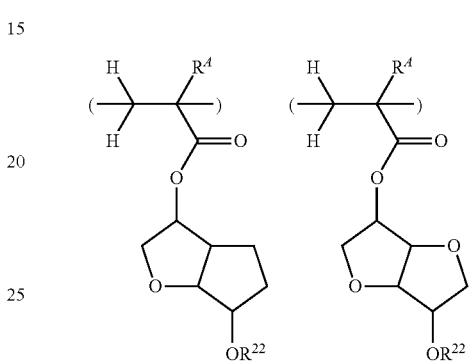
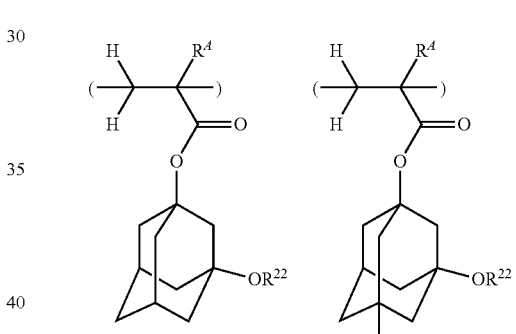
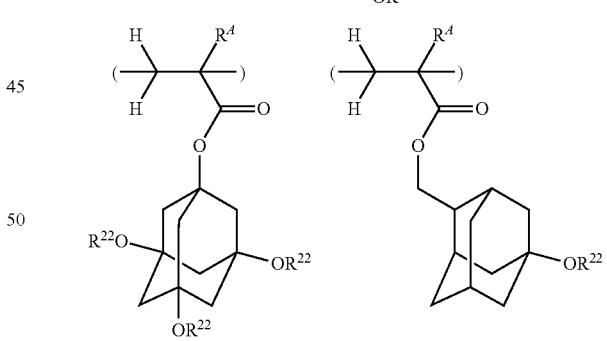
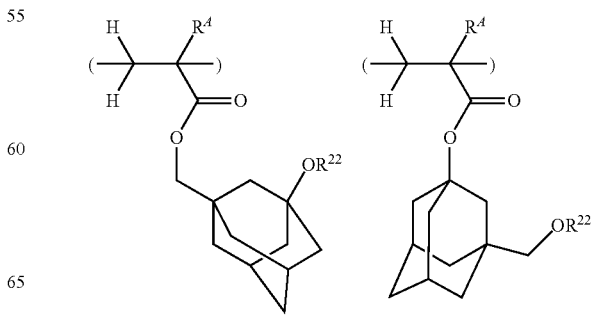

-continued

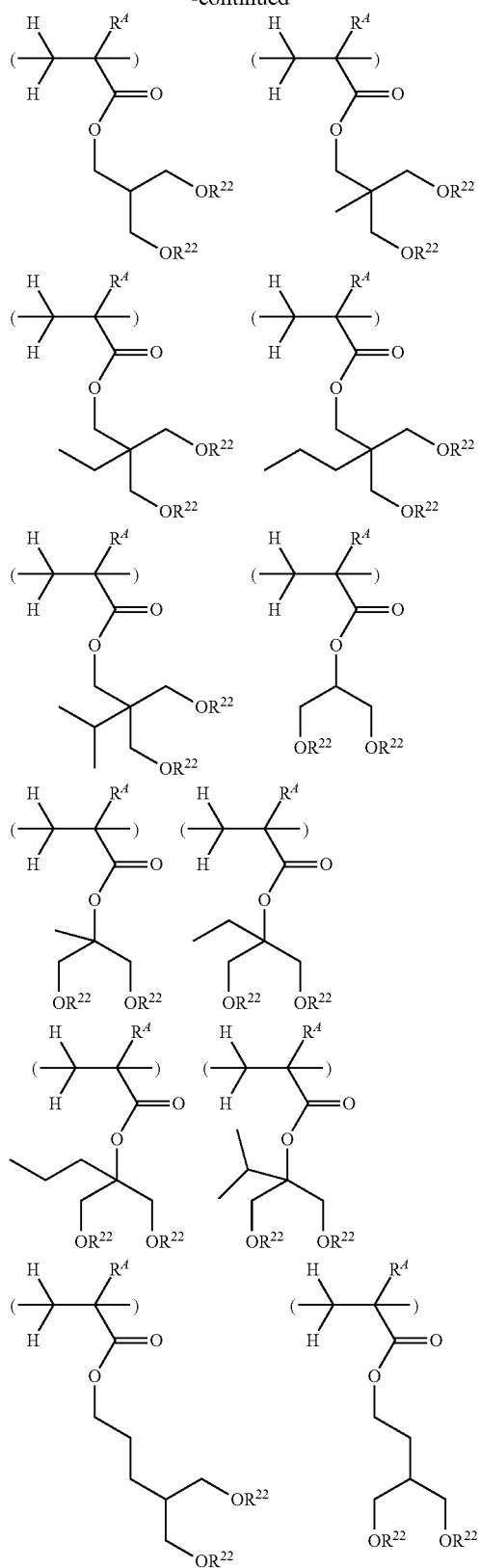

The structure of the acid labile group $R^{22}$ in formula (c1) is not particularly limited as long as it is deprotected to generate a hydroxyl group under the action of acid. Typical acid labile groups are groups of acetal or ketal structure and alkoxycarbonyl groups, with their examples being shown below.

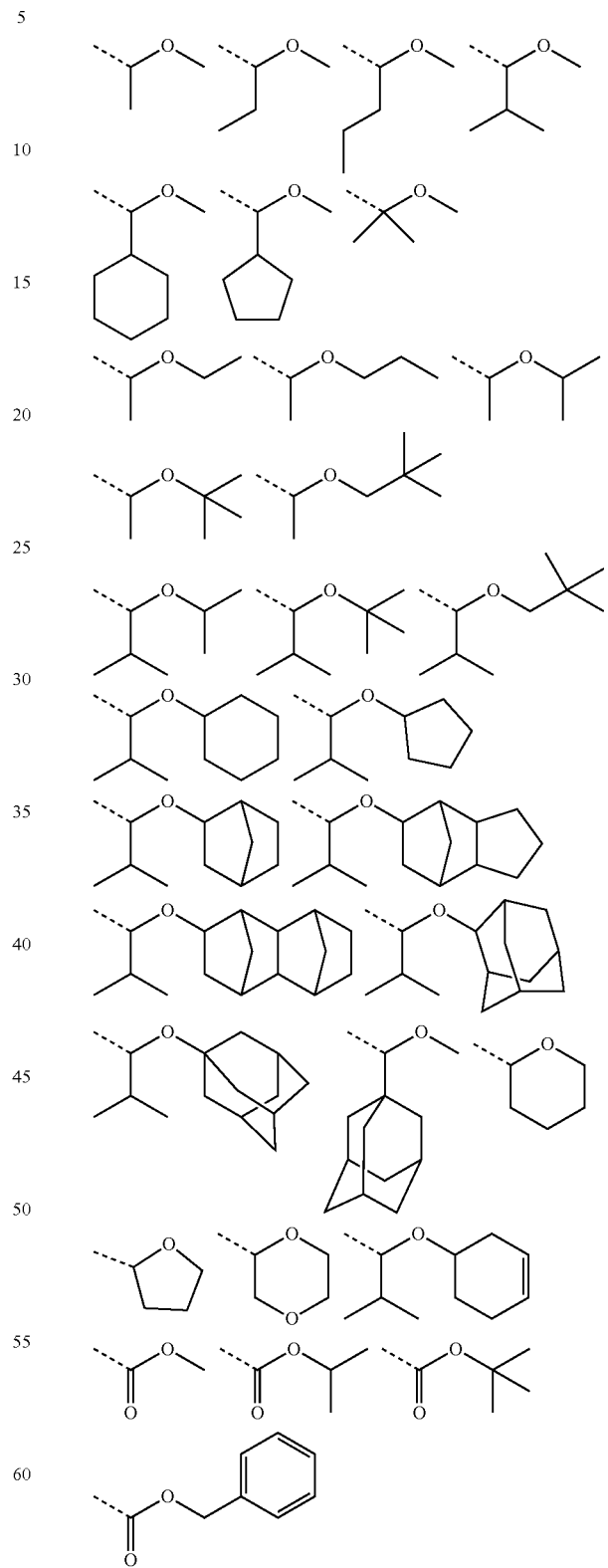

Of the acid labile group $R^{22}$, alkoxymethyl groups having the formula (c2) are preferred.

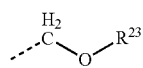 (c2)
In formula (c2), $R^{23}$ is a $C_1$-$C_{15}$ monovalent hydrocarbon group, which may be straight, branched or cyclic.
Examples of the acid labile group of formula (c2) are shown below, but not limited thereto.
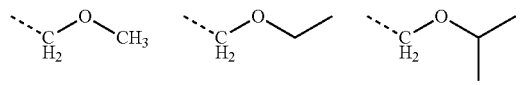
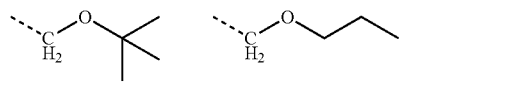
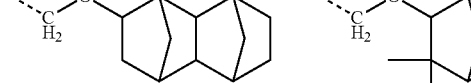
-continued
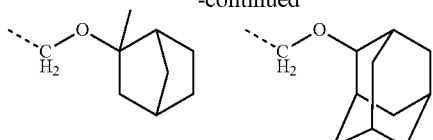
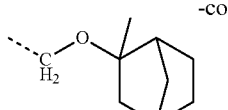
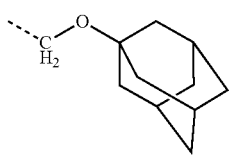
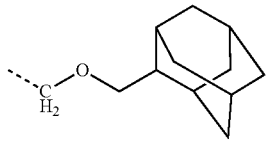
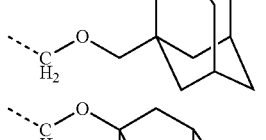
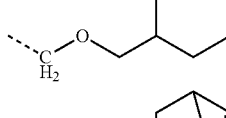
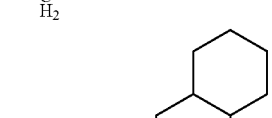
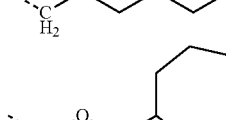
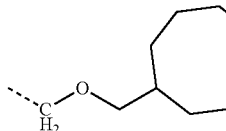
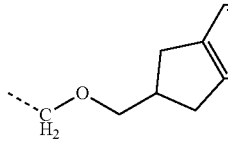
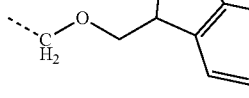

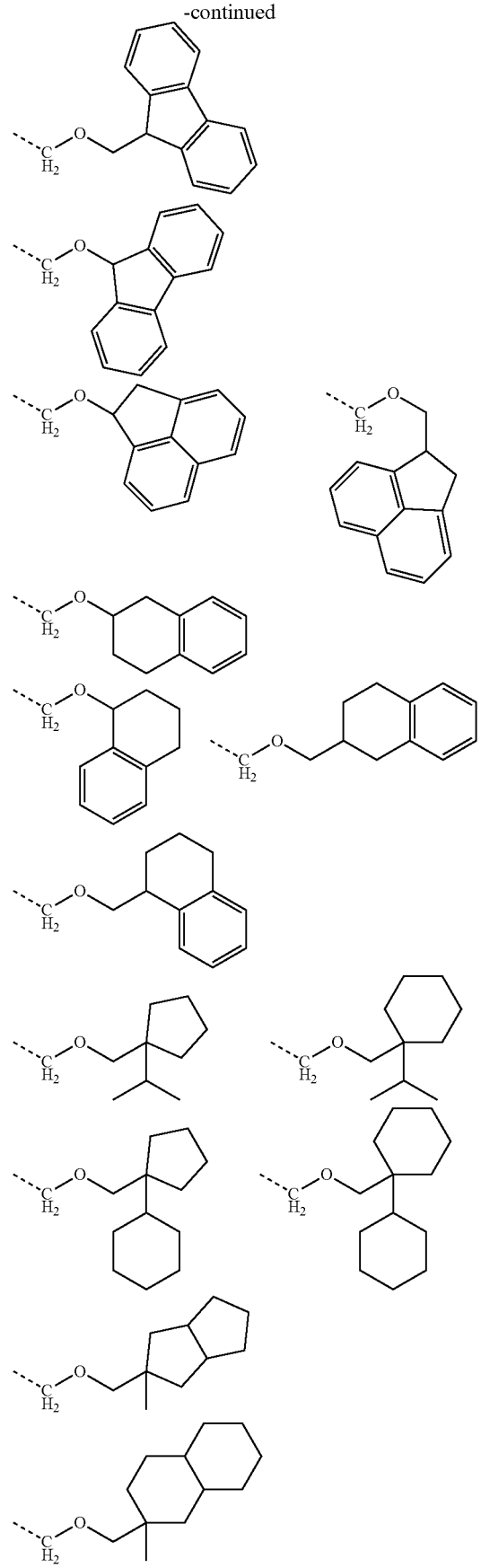
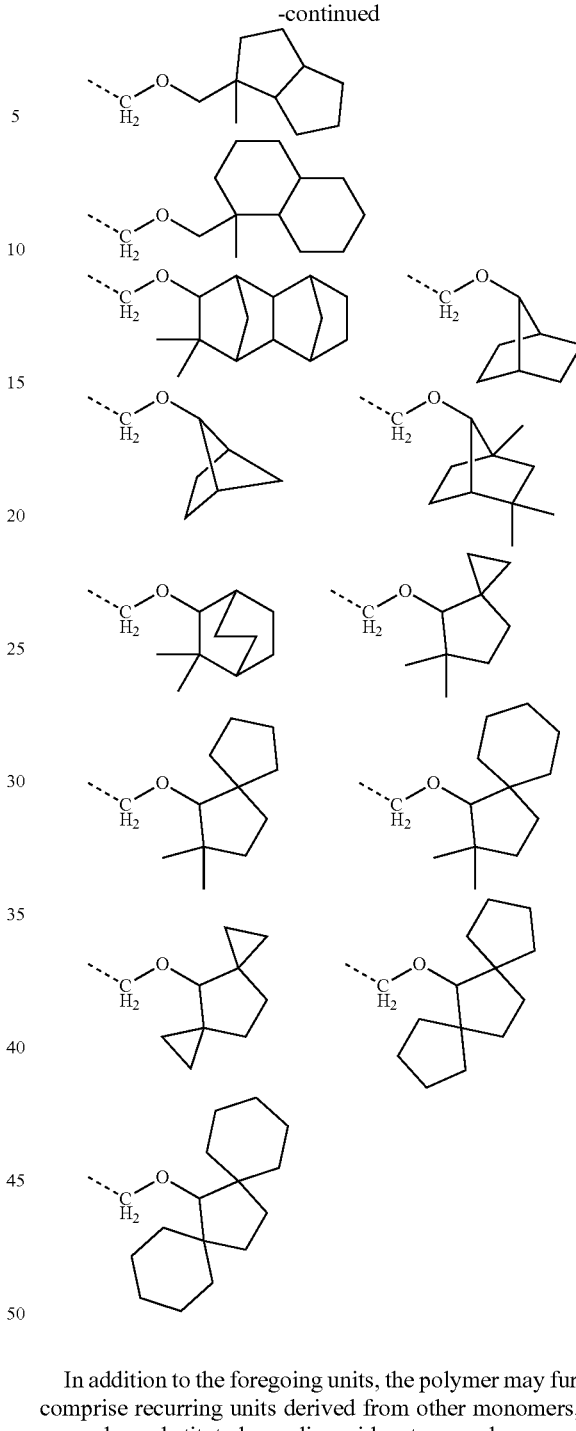

In addition to the foregoing units, the polymer may further comprise recurring units derived from other monomers, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[6.2.1. $1^{3,6}.0^{2,7}$]dodecene derivatives, unsaturated acid anhydrides such as itaconic anhydride, and other monomers.

The polymer has a weight average molecular weight (Mw) of preferably 1,000 to 500,000, more preferably 3,000 to 100,000, as measured by gel permeation chromatography (GPC) versus polystyrene standards using tetrahydrofuran (THF) solvent. As long as Mw is within the range, satisfactory etching resistance is ensured, and the risk of resolution lowering as a result of failure to establish a difference in dissolution rate before and after exposure is eliminated.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the polymer should preferably have a narrow dispersity (Mw/Mn) of 1.0 to 2.0 in order to formulate a resist composition suited for fine size pattern formation.

The method of synthesizing the polymer is, for example, by dissolving one or more unsaturated bond-bearing monomers in an organic solvent, adding a radical initiator, and heating the solution for polymerization. Examples of the organic solvent which can be used for polymerization include toluene, benzene, THF, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is in a range of 50 to 80° C. and the reaction time is 2 to 100 hours, more preferably 5 to 20 hours. The acid labile group that has been incorporated in the monomer may be kept as such, or polymerization may be followed by protection or partial protection.

While the polymer comprises recurring units derived from monomers, the molar fractions of respective units preferably fall in the following range (mol %), but are not limited thereto:

(I) 1 to 60 mol %, more preferably 5 to 50 mol %, even more preferably 10 to 50 mol % of constituent units of at least one type having formula (a), (II) 40 to 99 mol %, more preferably 50 to 95 mol %, even more preferably 50 to 90 mol % of constituent units of at least one type having formula (b), and (III) 0 to 80 mol %, more preferably 0 to 70 mol %, and even more preferably 0 to 50 mol % of constituent units of at least one type derived from another monomer(s).

The base resin (B) may be the polymer (defined above) alone or a mixture of two or more polymers which are different in compositional ratio, Mw and/or Mw/Mn.

(C) Organic Solvent

The resist composition may comprise (C) an organic solvent. The organic solvent used herein is not particularly limited as long as the foregoing components and other components are soluble therein. Examples of the organic solvent are described in JP-A 2008-111103, paragraphs [0144]-[0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone (GBL), and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, cyclohexanone, GBL, and mixtures thereof because the PAG (A) is most soluble therein.

An appropriate amount of the organic solvent (C) used is 200 to 5,000 parts, more preferably 400 to 3,000 parts by weight per 100 parts by weight of the base resin (B).

(D) Quencher

If necessary, the resist composition may further comprise (D) a quencher. As used herein, the "quencher" refers to a compound capable of trapping the acid generated by the PAG, for thereby suppressing the rate of diffusion when the generated acid diffuses within the resist film.

As the quencher, onium salts having the formulae (1a) and (1b) are preferred.

Herein $R^{q1}$ is hydrogen or a $C_1$-$C_{40}$ monovalent hydrocarbon group which may contain a heteroatom, excluding the hydrocarbon group in which the hydrogen atom bonded to the carbon atom at α-position relative to the sulfo group is substituted by fluorine or fluoroalkyl. $R^{q2}$ is hydrogen or a $C_1$-$C_{40}$ monovalent hydrocarbon group which may contain a heteroatom.

$R^{q1}$ is hydrogen or a monovalent hydrocarbon group, examples of which include methyl, ethyl, propyl, isopropyl, n-butyl, sec-butyl, tert-butyl, n-pentyl, tert-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbomyl, tricyclo[5.2.1.0$^{2,6}$]decanyl, adamantyl, phenyl, naphthyl, and anthracenyl. In the foregoing groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl moiety, cyano moiety, carbonyl moiety, ether bond, ester bond, sulfonate bond, carbonate bond, lactone ring, sultone ring, carboxylic anhydride or haloalkyl moiety.

Examples of the monovalent hydrocarbon group represented by $R^{q2}$ include those exemplified above for $R^{q1}$, and fluorinated alkyl groups such as trifluoromethyl and trifluoroethyl and fluorinated aryl groups such as pentafluorophenyl and 4-trifluoromethylphenyl.

Examples of the anion in the onium salt having formula (1a) are shown below, but not limited thereto.

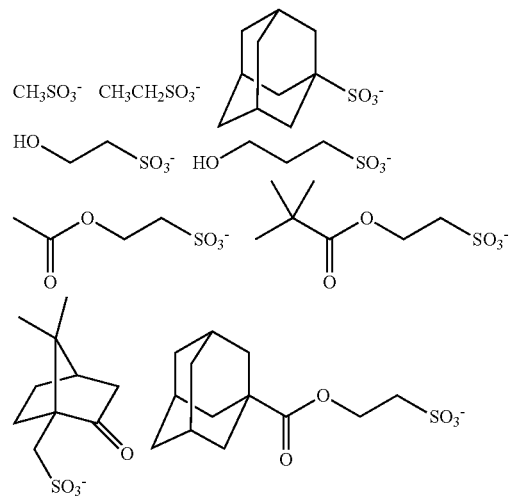

95
-continued
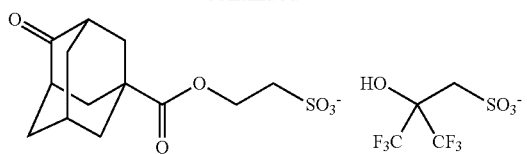
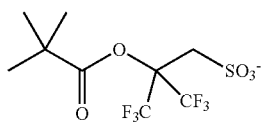
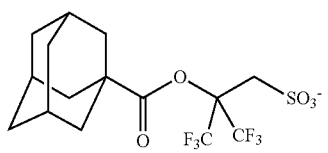
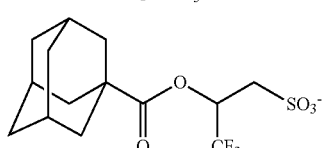
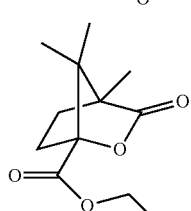
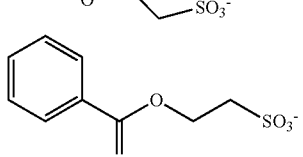
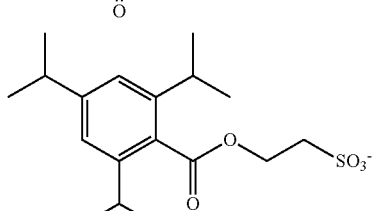
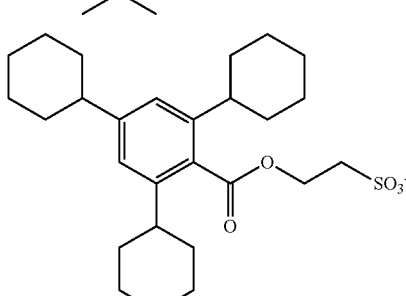
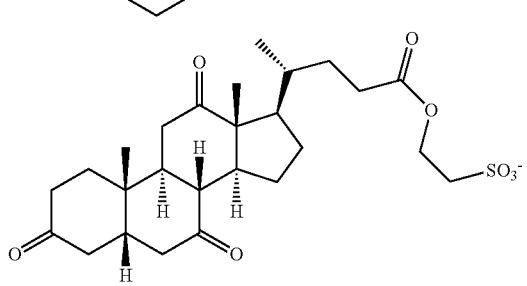
96
-continued
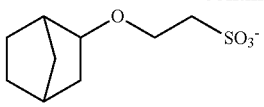
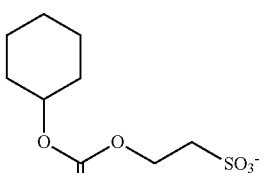
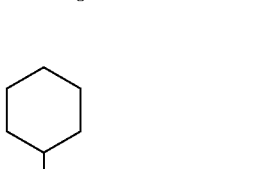
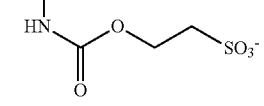
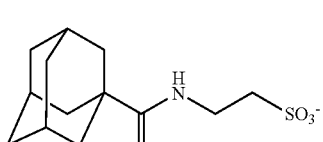
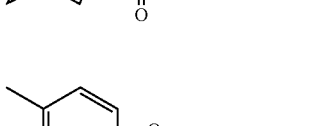
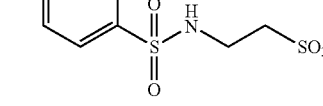
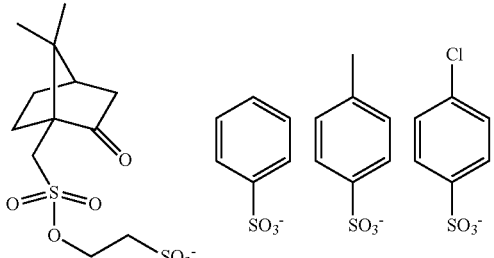
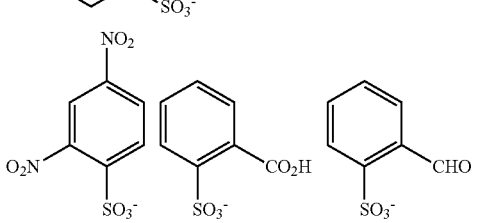
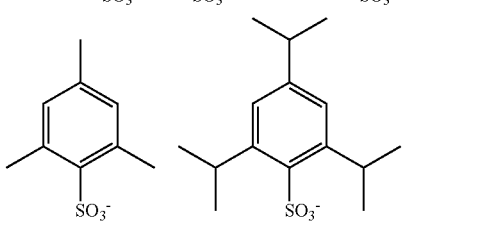

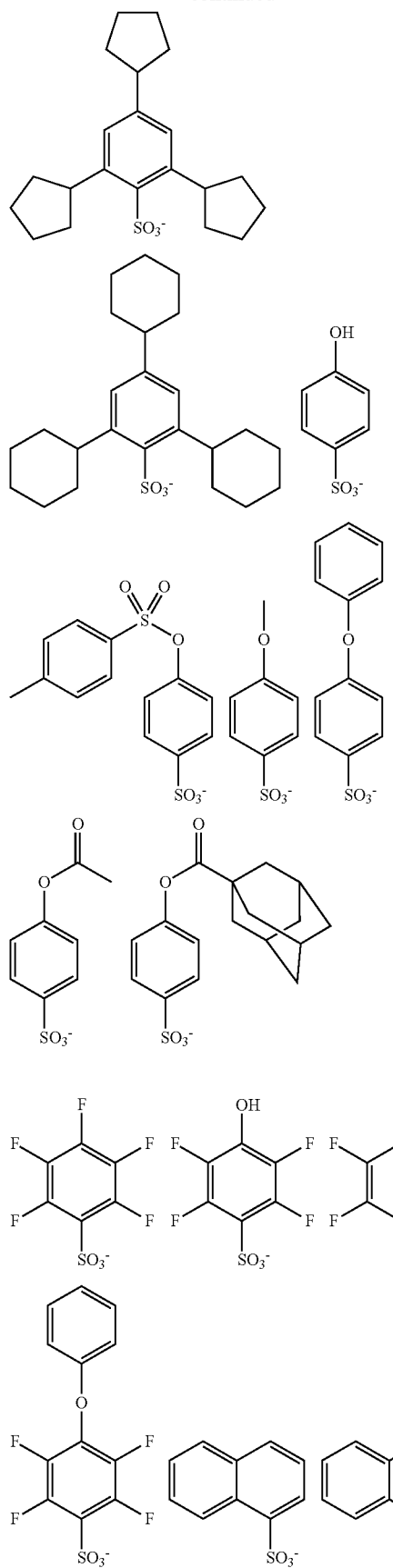
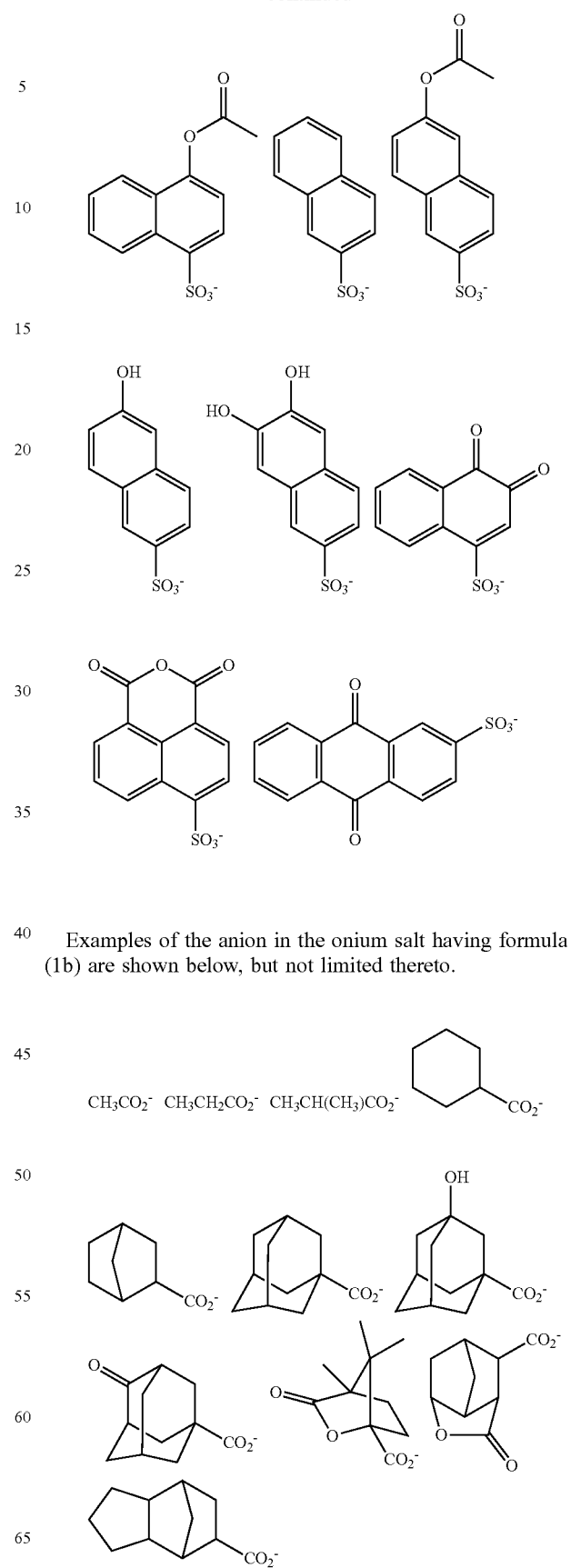
Examples of the anion in the onium salt having formula (1b) are shown below, but not limited thereto.

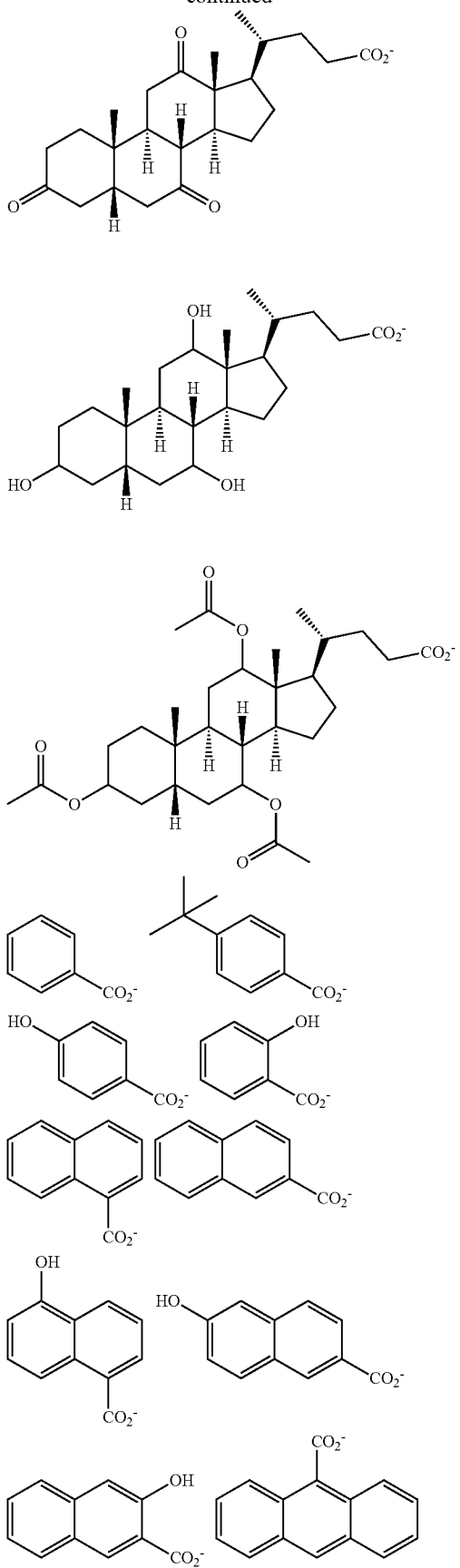

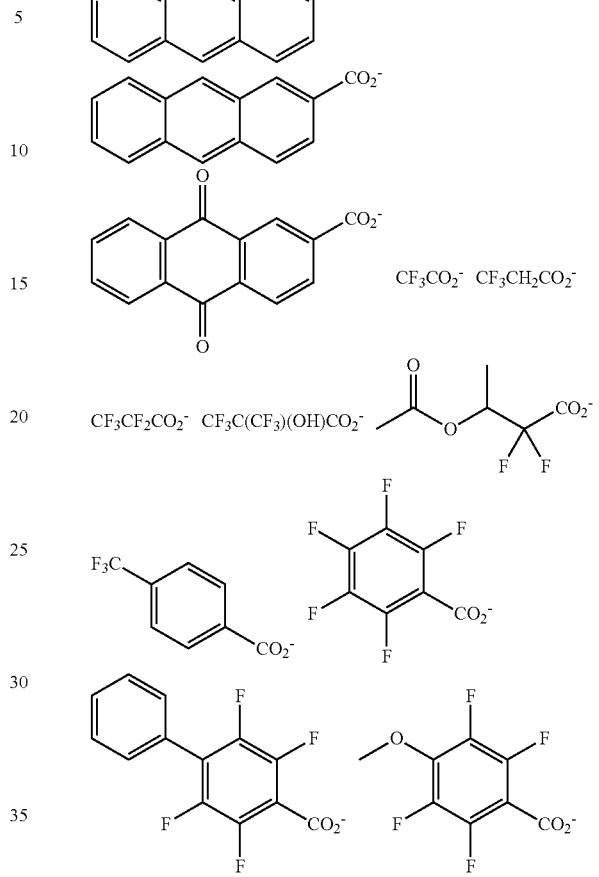

In formulae (1a) and (1b), $Mq^+$ is an onium cation. Onium cations having the formulae (2a), (2b) and (2c) are preferred.

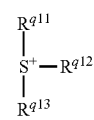 (2a)

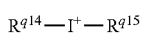 (2b)

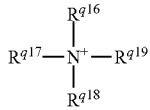 (2c)

Herein $R^{q11}$ to $R^{q19}$ are each independently a $C_1$-$C_{20}$ monovalent hydrocarbon group which may contain a heteroatom. Any two of $R^{q11}$ to $R^{q13}$ may bond together to form a ring with the sulfur atom to which they are attached. $R^{q14}$ and $R^{q15}$ may bond together to form a ring with the iodine atom to which they are attached. Any two of $R^{q16}$ to $R^{q19}$ may bond together to form a ring with the nitrogen atom to which they are attached. The monovalent hydrocarbon group may be straight, branched or cyclic. Examples thereof include alkyl groups such as methyl, ethyl, propyl, isopropyl, n-butyl, sec-butyl, tert-butyl, n-pentyl, tert-pentyl, n-hexyl, n-octyl, cyclopentyl, cyclohexyl, 2-ethylhexyl, cyclopentylmethyl, cyclopentylethyl, cyclohexylmethyl, cyclohexylethyl, norbornyl, oxanorbornyl, tricyclo[5.2.1.0$^{2,6}$]decanyl, adamantyl, and aryl groups such as phenyl and naphthyl. In the foregoing groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl moiety, cyano moiety, carbonyl moiety, ether bond, ester bond, sulfonate bond, carbonate bond, lactone ring, sultone ring, carboxylic anhydride or haloalkyl moiety.

Examples of the onium cation are shown below, but not limited thereto.

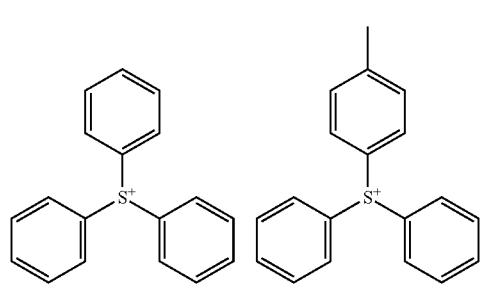

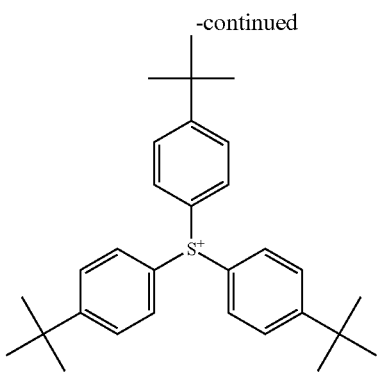

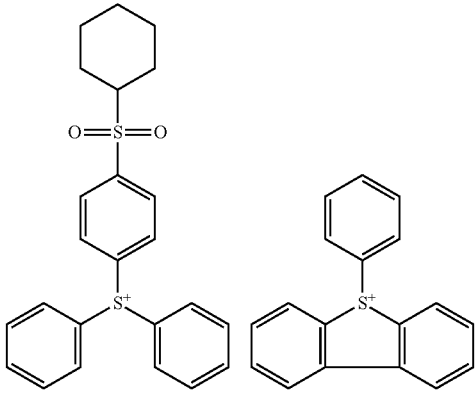

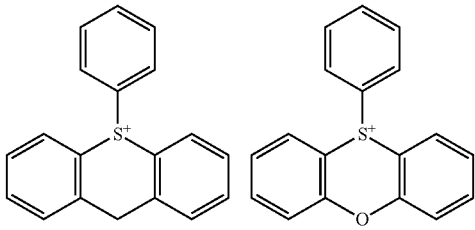

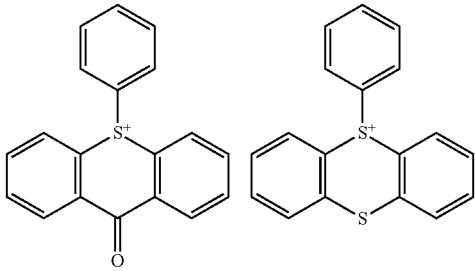

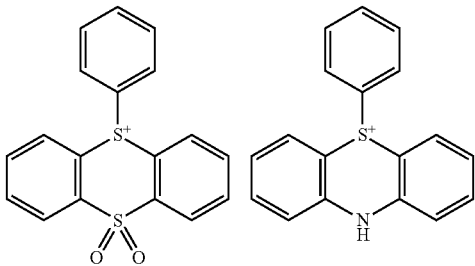

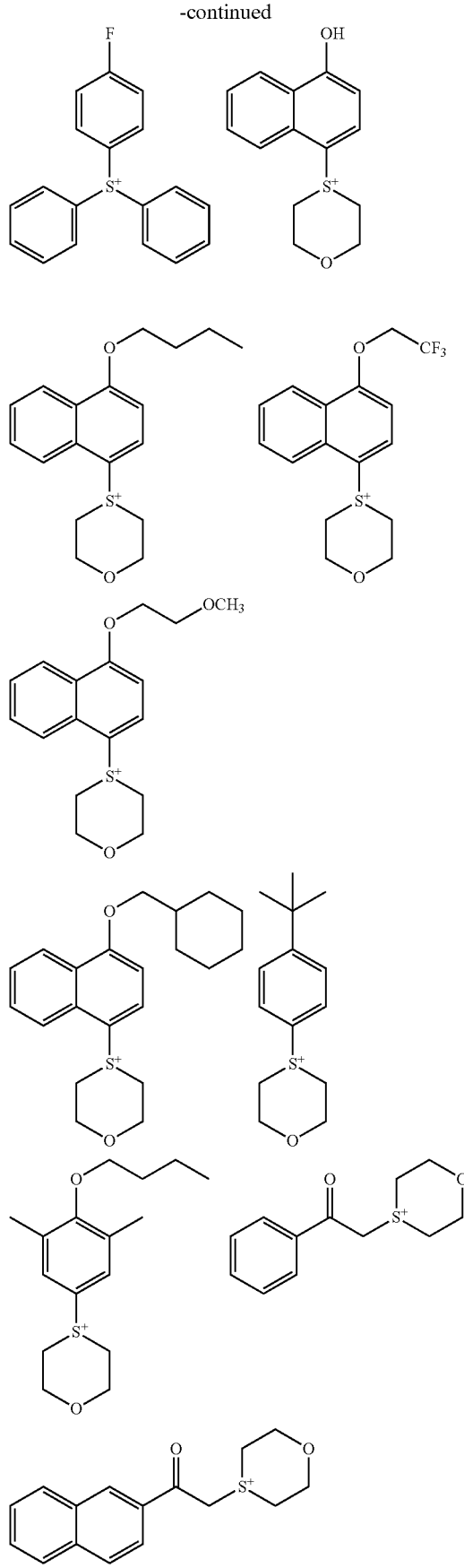
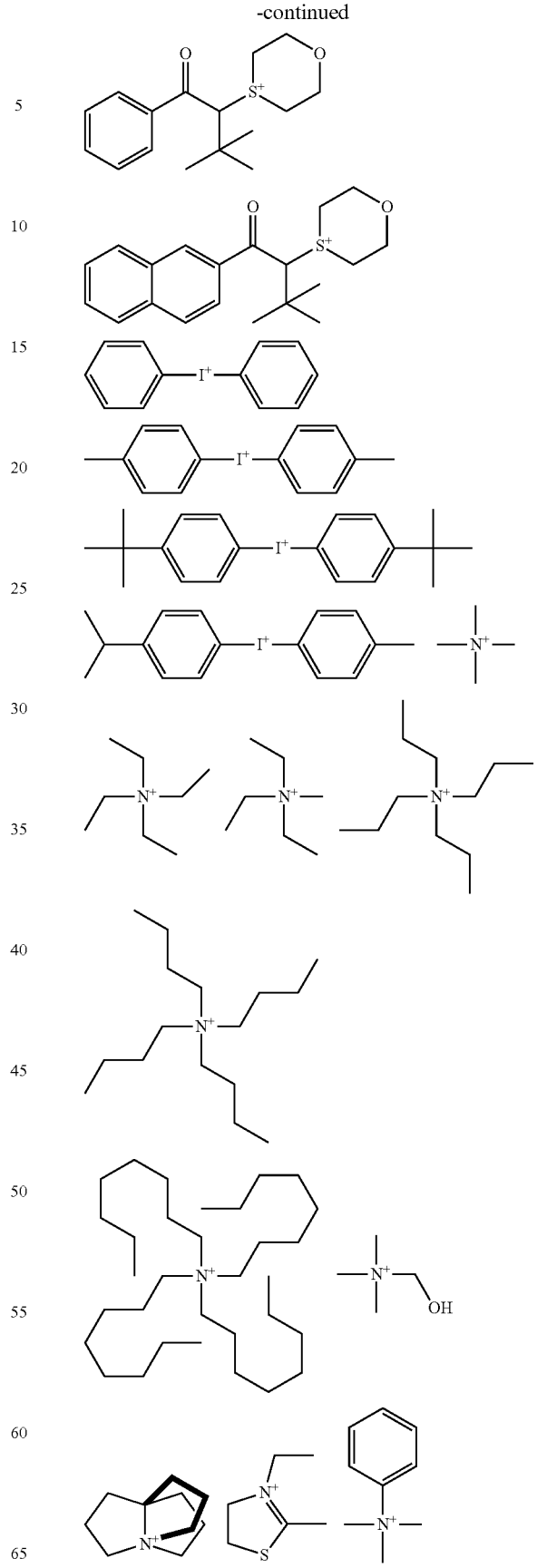

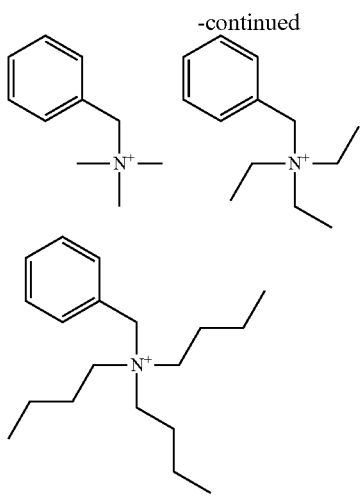

Examples of the onium salt having formula (1a) or (1b) include arbitrary combinations of anions with cations, both as exemplified above. Such onium salts may be readily prepared by ion exchange reaction. The ion exchange reaction may be readily carried out by any well-known techniques, with reference to JP-A 2007-145797, for example.

The onium salt having formula (1a) or (1b) functions as a quencher because the counter anion of the onium salt is a conjugated base of weak acid. As used herein, the "weak acid" indicates an acidity insufficient to deprotect an acid labile group from an acid labile group-containing unit in the base resin. The onium salt having formula (1a) or (1b) functions as a quencher when used in combination with an onium salt type PAG having a conjugated base of a strong acid, typically a sulfonic acid which is fluorinated at α-position as the counter anion. In a system using a mixture of an onium salt capable of generating a strong acid (e.g., α-position fluorinated sulfonic acid) and an onium salt capable of generating a weak acid (e.g., α-position non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion. In this way, the onium salt having formula (1a) or (1b) functions as the quencher.

If a PAG capable of generating a strong acid is an onium salt, an exchange from the strong acid generated upon exposure to high-energy radiation to a weak acid as above can take place, but it rarely happens that the weak acid generated upon exposure to high-energy radiation collides with the unreacted onium salt capable of generating a strong acid to induce a salt exchange. This is because of a likelihood of an onium cation forming an ion pair with a stronger acid anion.

An appropriate amount of the onium salt having formula (1a) or (1b) added is 0 to 40 parts, and if used, preferably 0.1 to 40 parts, and more preferably 0.1 to 20 parts by weight per 100 parts by weight of the base resin (B). An excess of the onium salt may cause a degradation of resolution or leave foreign particles after resist development or stripping. The onium salt having formula (1a) or (1b) may be used alone or in admixture.

Besides the onium salt having formula (1a) or (1b), a photo-decomposable onium salt having a nitrogen-containing substituent group may also be used as the quencher (D). This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595, 2012-046501 and JP-A 2013-209360, for example.

An appropriate amount of the photo-degradable base added is 0 to 40 parts, and if used, preferably 0.1 to 40 parts, and more preferably 0.1 to 20 parts by weight per 100 parts by weight of the base resin (B). An excess of the base may cause a degradation of resolution or leave foreign particles after resist development or stripping. The photo-degradable base may be used alone or in admixture.

Amine compounds may also be used as the quencher. Suitable amine compounds include primary, secondary and tertiary amine compounds, specifically amine compounds having a hydroxyl, ether bond, ester bond, lactone ring, cyano or sulfonate group, as described in JP-A 2008-111103, paragraphs [0146]-[0164] (U.S. Pat. No. 7,537,880), and compounds having primary or secondary amine protected with a carbamate group, as described in JP 3790649.

An appropriate amount of the amine compound is 0 to 12 parts by weight, and if used, preferably 0.001 to 12 parts, more preferably 0.01 to 8 parts by weight, per 100 parts by weight of the base resin (B). The inclusion of the amine compound facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The amine compound is also effective for improving adhesion to the substrate. The amine compound may be used alone or in admixture.

(E) Other PAG

The resist composition may further comprise (E) a photoacid generator other than the salt compound having formula (A). The other PAG may be any compound capable of generating an acid upon exposure to high-energy radiation such as UV, deep UV, EB, EUV, x-ray, excimer laser, gamma-ray or synchrotron radiation. Suitable PAGs include sulfonium salts, iodonium salts, sulfonyldiazomethane, N-sulfonyloxydicarboxyimide, O-arylsulfonyloxime and O-alkylsulfonyloxime photoacid generators. These PAGs may be used alone or in admixture of two or more. Suitable PAGs are described, for example, in U.S. Pat. No. 7,511,169 (JP-A 2007-145797, paragraphs [0102]-[0113]). It is noted that diphenyliodonium and di-tert-butylphenyliodonium are preferred as the cation of the iodonium salt.

The preferred PAG has the formula (3).

(3)

In formula (3), $R^{101}$, $R^{102}$ and $R^{103}$ are each independently a $C_1$-$C_{20}$ monovalent hydrocarbon group which may contain a heteroatom. The monovalent hydrocarbon group may be straight, branched or cyclic. Examples thereof include alkyl groups such as methyl, ethyl, propyl, isopropyl, n-butyl, sec-butyl, tert-butyl, n-pentyl, tert-pentyl, n-hexyl, n-octyl, cyclopentyl, cyclohexyl, 2-ethylhexyl, cyclopentylmethyl, cyclopentylethyl, cyclohexylmethyl, cyclohexylethyl, norbornyl, oxanorbornyl, tricyclo[5.2.1.0$^{2,6}$]decanyl, and adamantyl, and aryl groups such as phenyl and naphthyl. In the foregoing groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl moiety, cyano moiety, carbonyl moiety, ether bond, ester bond, sulfonate bond, carbonate bond, lactone ring, sultone ring, carboxylic anhydride or haloalkyl moiety. Among others, $R^{101}$, $R^{102}$ and $R^{103}$ are preferably optionally substituted aryl groups.

Any two of $R^{101}$, $R^{102}$ and $R^{103}$ may bond together to form a ring with the sulfur atom to which they are attached. Examples of the cation in formula (3) involving cyclization are shown below.

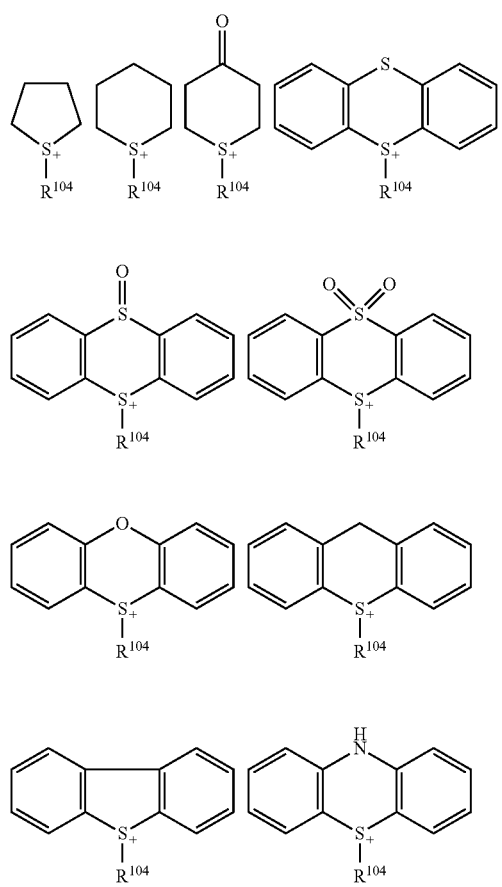

Herein $R^{104}$ is a $C_1$-$C_{20}$ monovalent hydrocarbon group which may contain a heteroatom. Examples of the monovalent hydrocarbon group are as exemplified above for $R^{101}$ to $R^{103}$.

Examples of the sulfonium cation in formula (3) are shown below, but not limited thereto.

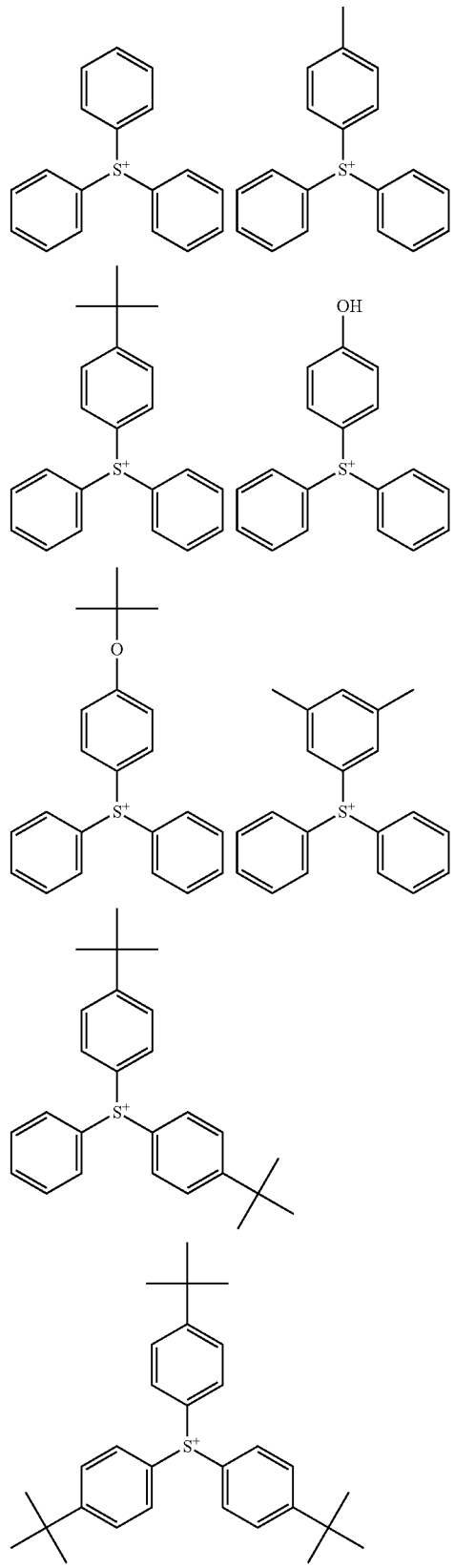

-continued

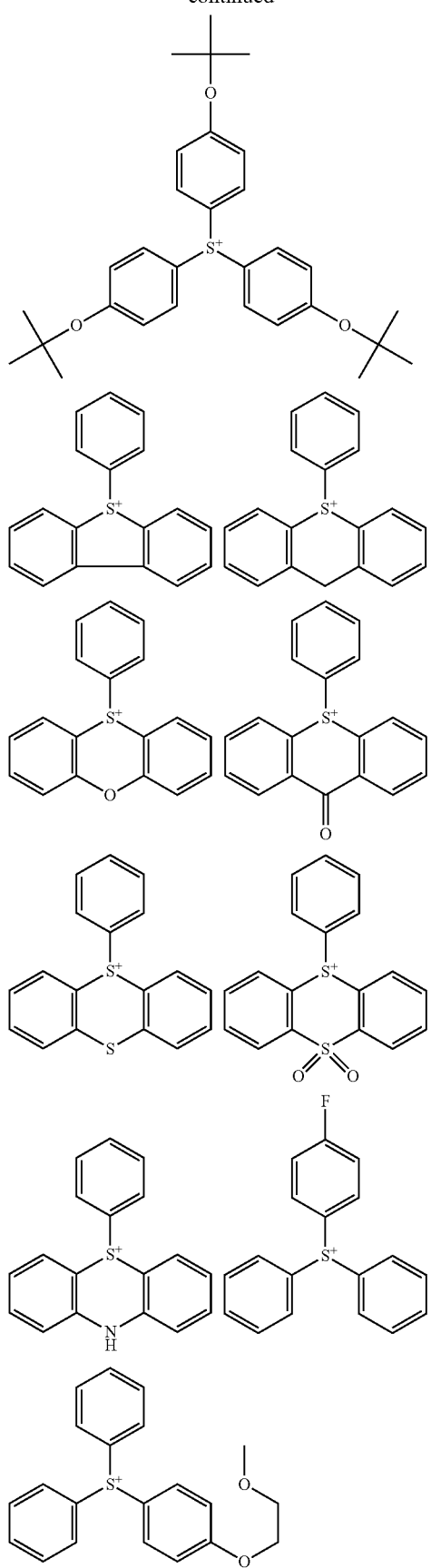

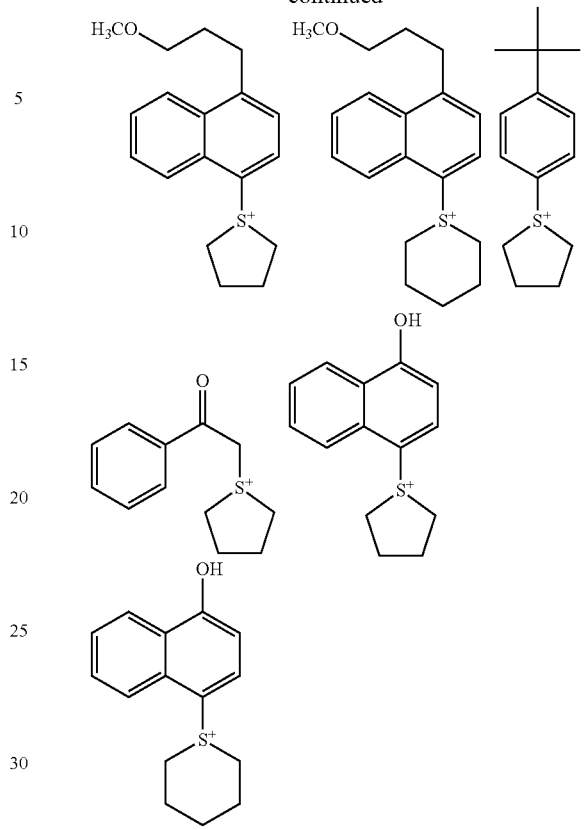

In formula (3), $X^-$ is an anion selected from the formulae (3A) to (3D).

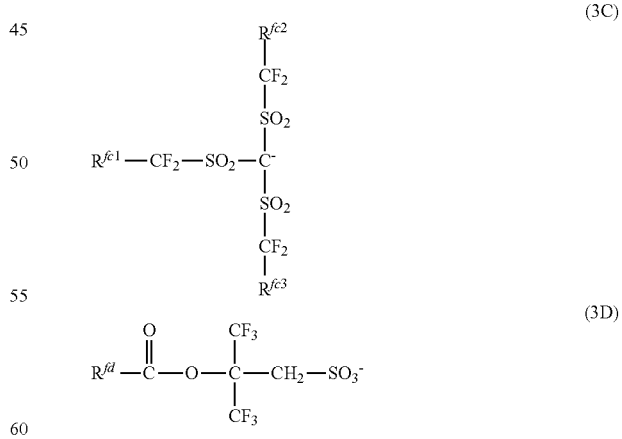

In formula (3A), $R^{fa}$ is fluorine or a $C_1$-$C_{40}$ monovalent hydrocarbon group which may contain a heteroatom. The monovalent hydrocarbon group may be straight, branched or cyclic. Preferred structures of the anion having formula (3A) include nonafluorobutane sulfonate, partially fluorinated sulfonates described in JP-A 2012-189977, paragraphs

[0247]-[0251], and partially fluorinated sulfonates described in JP-A 2013-101271, paragraphs [0261]-[0265].

Of the anions of formula (3A), a structure having formula (3A') is preferred.

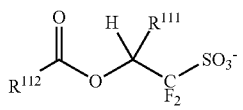
(3A')

In formula (3A'), $R^{111}$ is hydrogen or trifluoromethyl. $R^{112}$ is a $C_1$-$C_{30}$ monovalent hydrocarbon group which may contain a heteroatom. Suitable heteroatoms include oxygen, nitrogen, sulfur and halogen, with oxygen being preferred. Of the monovalent hydrocarbon groups, those of 6 to 30 carbon atoms are preferred because a high resolution is available in fine pattern formation. The monovalent hydrocarbon group may be straight, branched or cyclic and examples thereof include methyl, ethyl, propyl, isopropyl, butyl, isobutyl, sec-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, icosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (3A'), reference is made to JP-A 2007-145797, JP-A 2008-106045, JP-A 2009-007327, and JP-A 2009-258695.

Examples of the anion having formula (3A) are shown below, but not limited thereto. Herein Ac stands for acetyl.

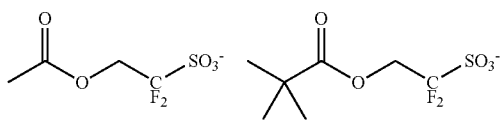

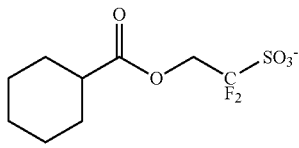

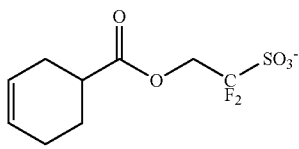

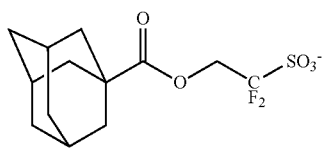

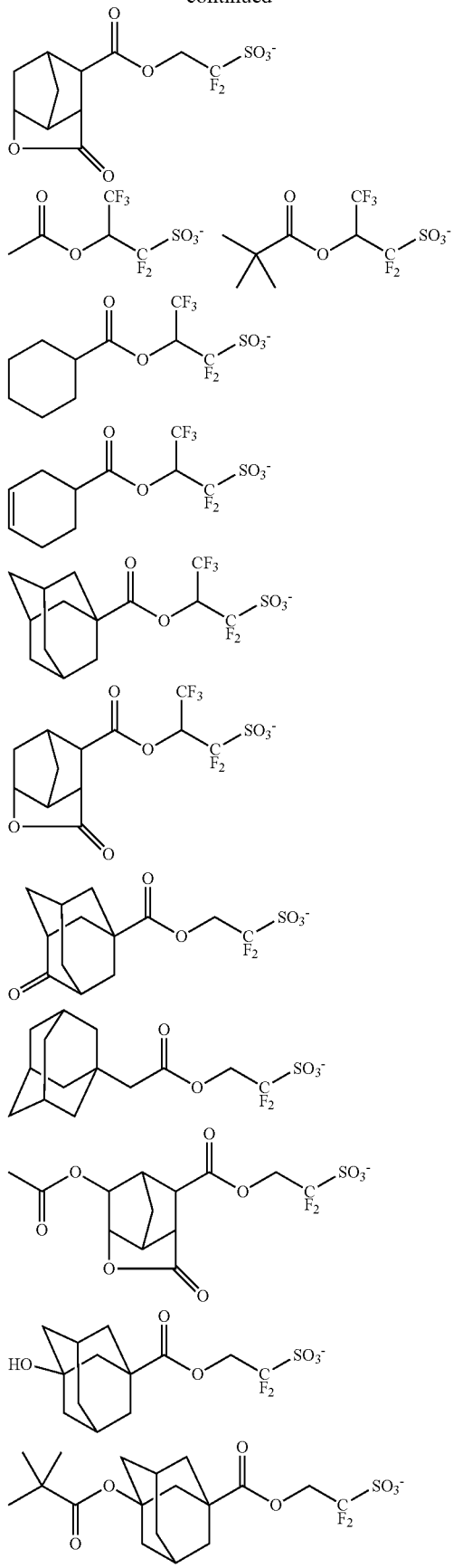

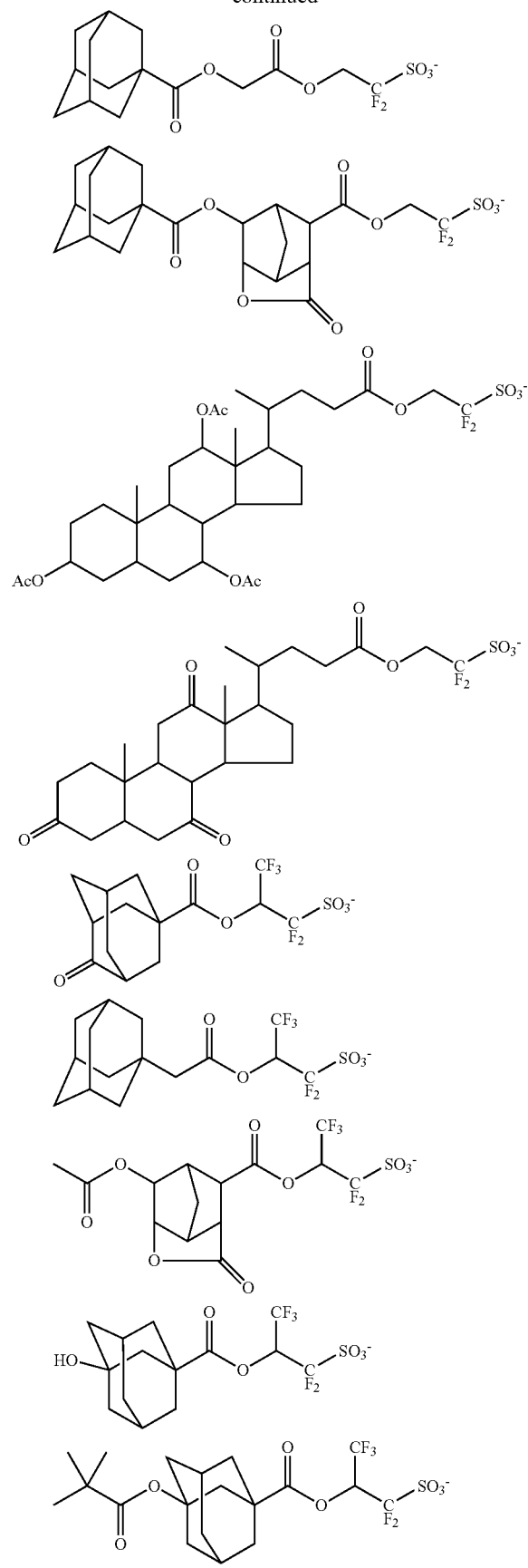
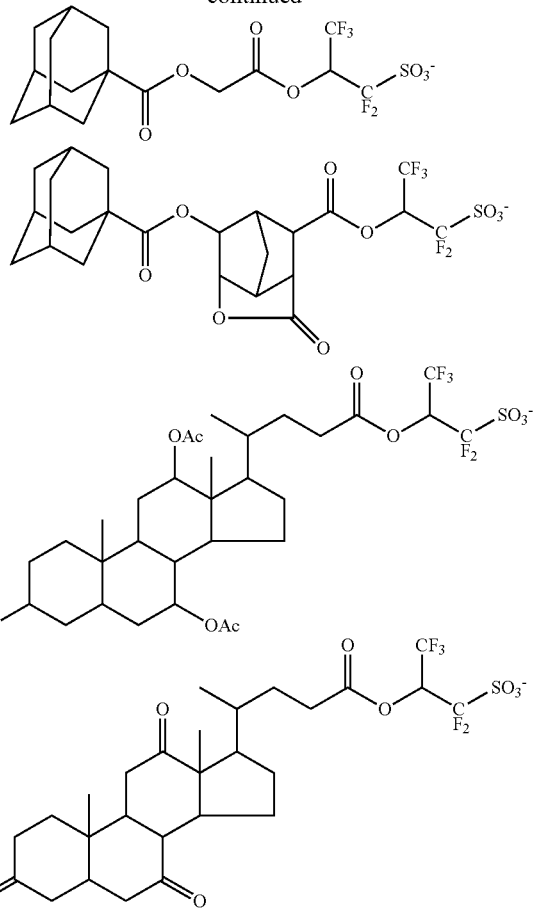

In formula (3B), $R^{fb1}$ and $R^{fb2}$ are each independently fluorine or a $C_1$-$C_{40}$ monovalent hydrocarbon group which may contain a heteroatom. The monovalent hydrocarbon group may be straight, branched or cyclic and examples thereof are as exemplified above for $R^{112}$. Preferably $R^{fb1}$ and $R^{fb2}$ each are fluorine or a $C_1$-$C_4$ straight fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group forming a ring structure.

In formula (3C), $R^{fc1}$, $R^{fc2}$ and $R^{fc3}$ are each independently fluorine or a $C_1$-$C_{40}$ monovalent hydrocarbon group which may contain a heteroatom. The monovalent hydrocarbon group may be straight, branched or cyclic and examples thereof are as exemplified above for $R^{112}$. Preferably $R^{fc1}$, $R^{fc2}$ and $R^{fc3}$ each are fluorine or a $C_1$-$C_4$ straight fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and preferably the pair is a fluorinated ethylene or fluorinated propylene group forming a ring structure.

In formula (3D), $R^{fd}$ is a $C_1$-$C_{40}$ monovalent hydrocarbon group which may contain a heteroatom. The monovalent hydrocarbon group may be straight, branched or cyclic and examples thereof are as exemplified above for $R^{112}$.

With respect to the synthesis of the sulfonium salt having an anion of formula (3D), reference is made to JP-A 2010-215608.

Examples of the anion having formula (3D) are shown below, but not limited thereto.

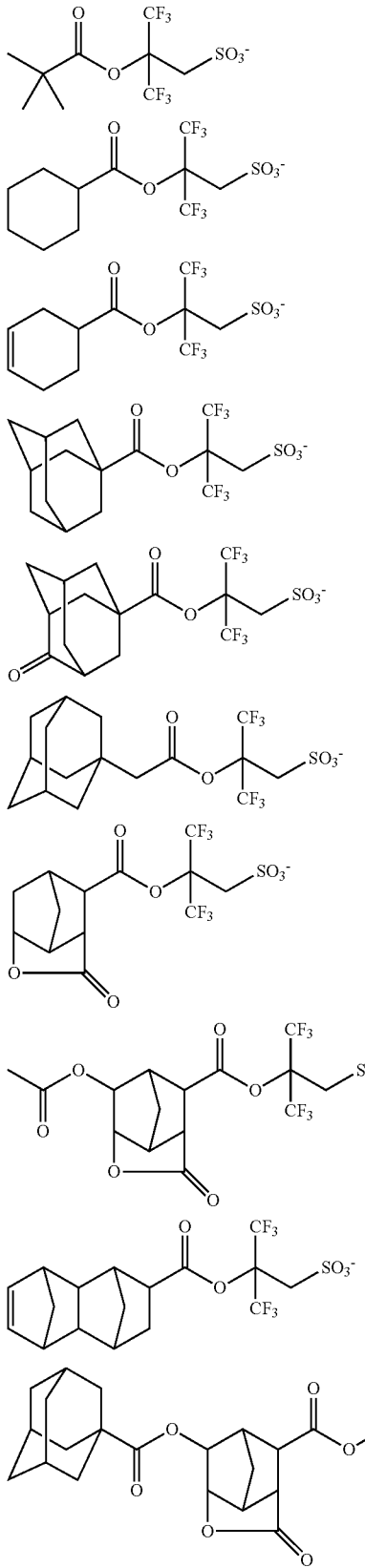

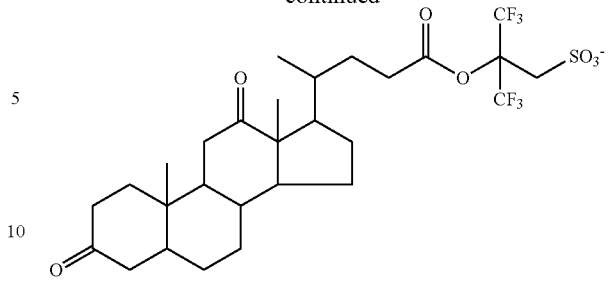

The compound having the anion of formula (3D) has a sufficient acid strength to cleave acid labile groups in the base resin because it is free of fluorine at α-position of sulfo group, but has two trifluoromethyl groups at 3-position. Thus the compound is a useful PAG.

As the other PAG (D), those compounds having the formula (4) are also preferred.

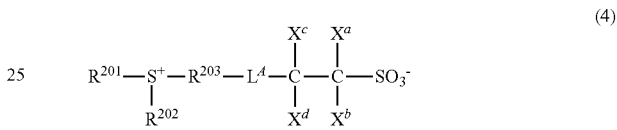

(4)

In formula (4), $R^{201}$ and $R^{202}$ are each independently a $C_1$-$C_{30}$ monovalent hydrocarbon group which may contain a heteroatom. $R^{203}$ is a $C_1$-$C_{30}$ divalent hydrocarbon group which may contain a heteroatom. Any two of $R^{201}$, $R^{202}$ and $R^{203}$ may bond together to form a ring with the sulfur atom to which they are attached. $L^4$ is a single bond, ether bond or a $C_1$-$C_{20}$ divalent hydrocarbon group which may contain a heteroatom. $X^a$, $X^b$, $X^c$ and $X^d$ are each independently hydrogen, fluorine or trifluoromethyl, with at least one thereof being fluorine or trifluoromethyl.

The monovalent hydrocarbon group represented by $R^{201}$ and $R^{202}$ may be straight, branched or cyclic. Examples thereof include methyl, ethyl, propyl, isopropyl, n-butyl, sec-butyl, tert-butyl, n-pentyl, tert-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl, and anthracenyl. In the foregoing groups, some hydrogen may be substituted by a moiety containing a heteroatom such as oxygen, sulfur, nitrogen or halogen, or a moiety containing a heteroatom such as oxygen, sulfur or nitrogen may intervene between carbon atoms, so that the group may contain a hydroxyl, cyano, carbonyl, ether bond, ester bond, sulfonate bond, carbonate bond, lactone ring, sultone ring, carboxylic anhydride or haloalkyl moiety.

The divalent hydrocarbon group $R^{203}$ may be straight, branched or cyclic. Examples thereof include linear alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic divalent hydrocarbon groups such as cyclopentanediyl, cyclohexanediyl, norbornanediyl, and adamantanediyl; and arylene groups such as phenylene and naphthylene. In the foregoing groups, some hydrogen may be substituted by an alkyl group such as methyl, ethyl, propyl, n-butyl or t-butyl, or some hydrogen may be substituted by a moiety containing a heteroatom such as oxygen, sulfur, nitrogen or halogen, or a moiety containing a heteroatom such as oxygen, sulfur or nitrogen may intervene between carbon atoms, so that the group may contain a hydroxyl, cyano, carbonyl, ether bond, ester bond, sulfonate bond, carbonate bond, lactone ring, sultone ring, carboxylic anhydride or haloalkyl moiety. Typical of the heteroatom is oxygen.

Of the PAGs of formula (4), a compound having the formula (4') is preferred.

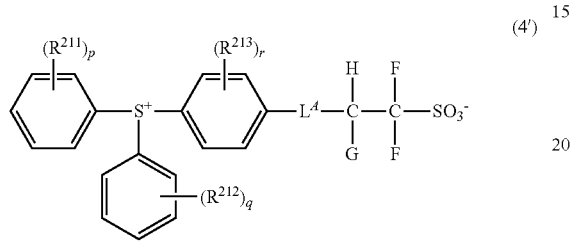

(4')

In formula (4'), $L^A$ is as defined above. G is hydrogen or trifluoromethyl, preferably trifluoromethyl. $R^{211}$, $R^{212}$ and $R^{213}$ are each independently hydrogen or a $C_1$-$C_{20}$ monovalent hydrocarbon group which may contain a heteroatom. The monovalent hydrocarbon group may be straight, branched or cyclic and examples thereof are as exemplified above for $R^{112}$. The subscripts p and q are each independently an integer of 0 to 5, and r is an integer of 0 to 4.

Examples of the PAG having formula (4) are given below, but not limited thereto. Herein G is as defined above.

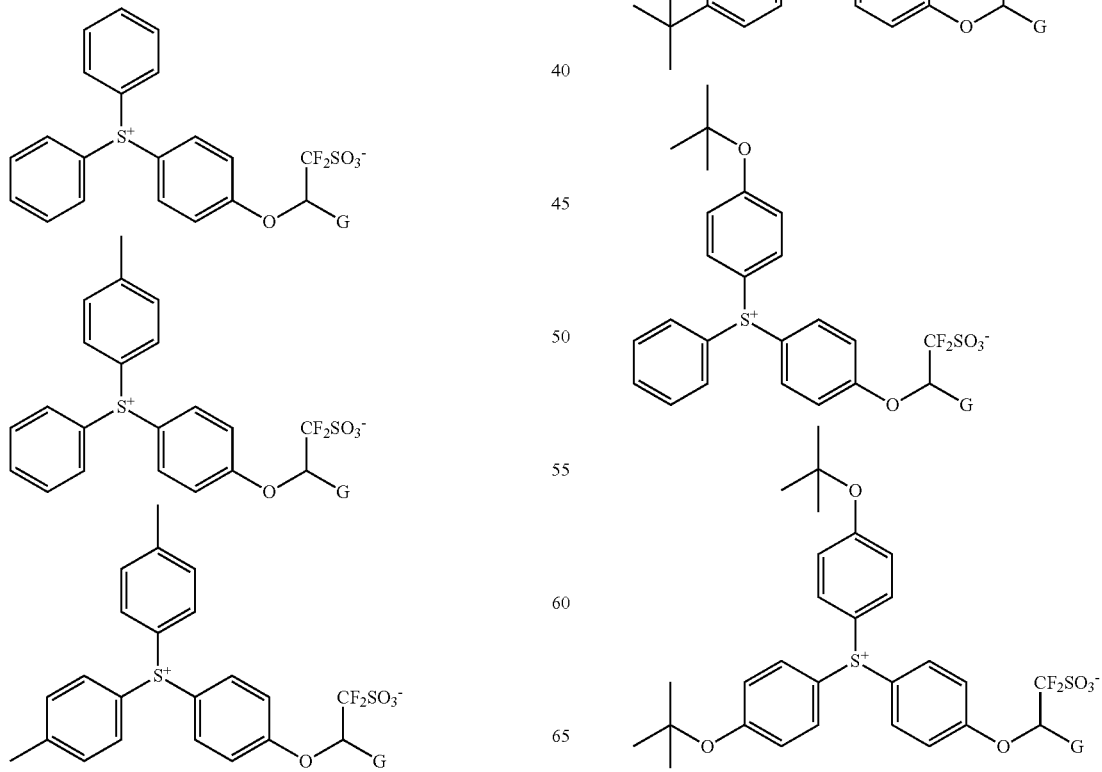

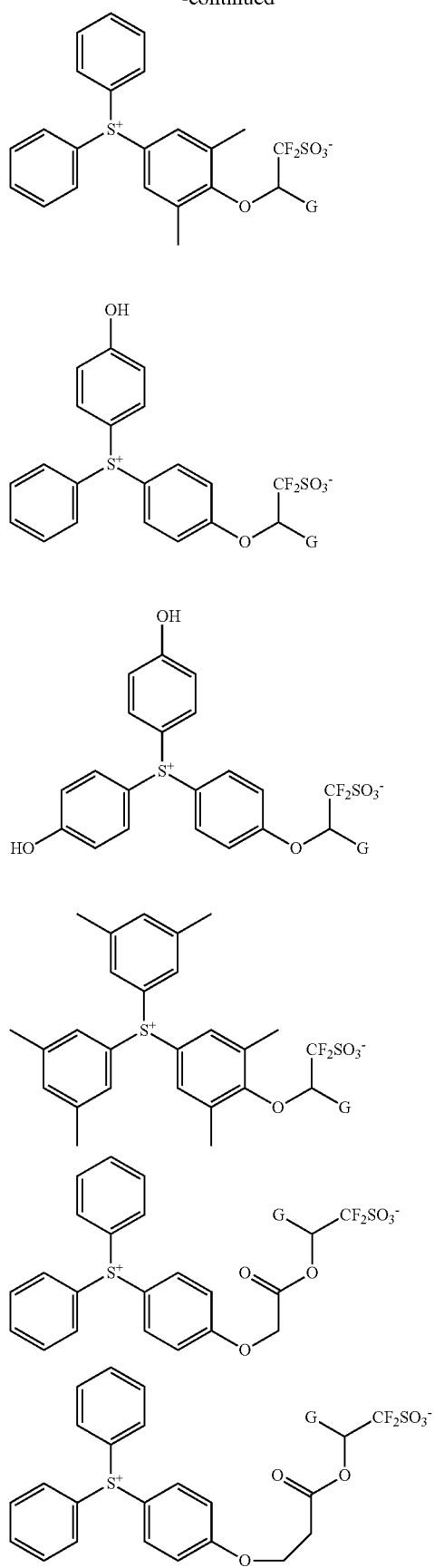
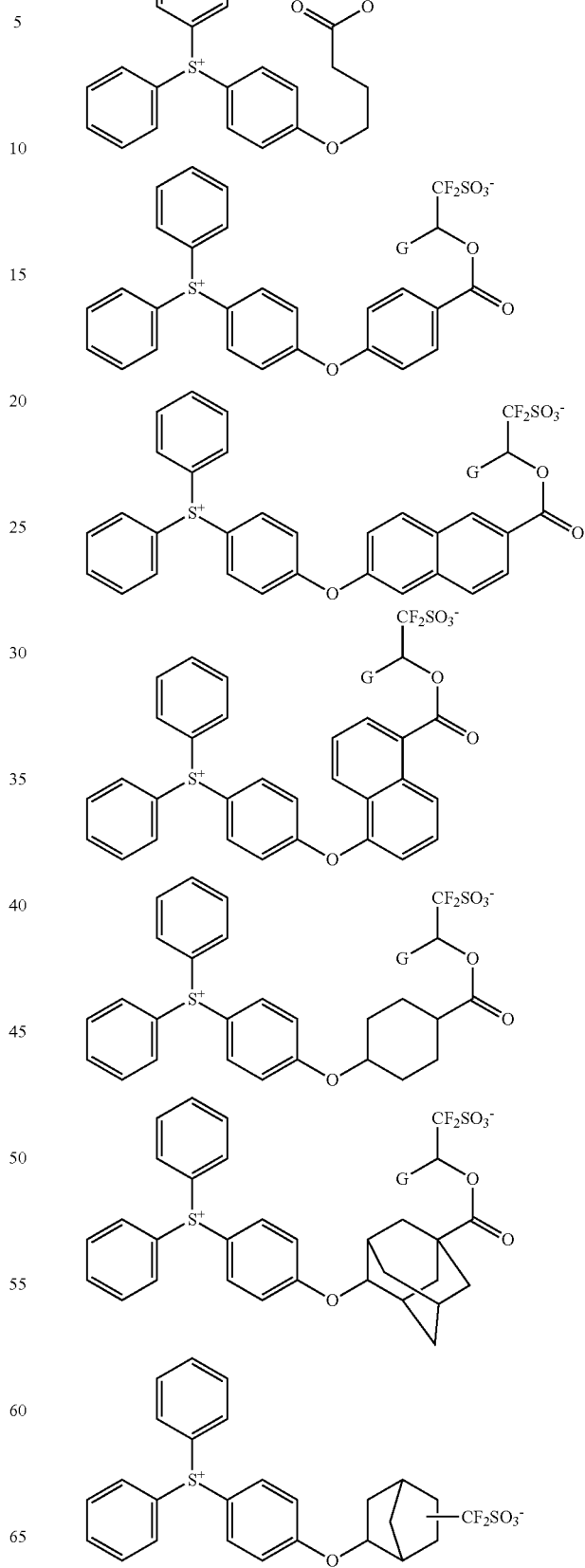

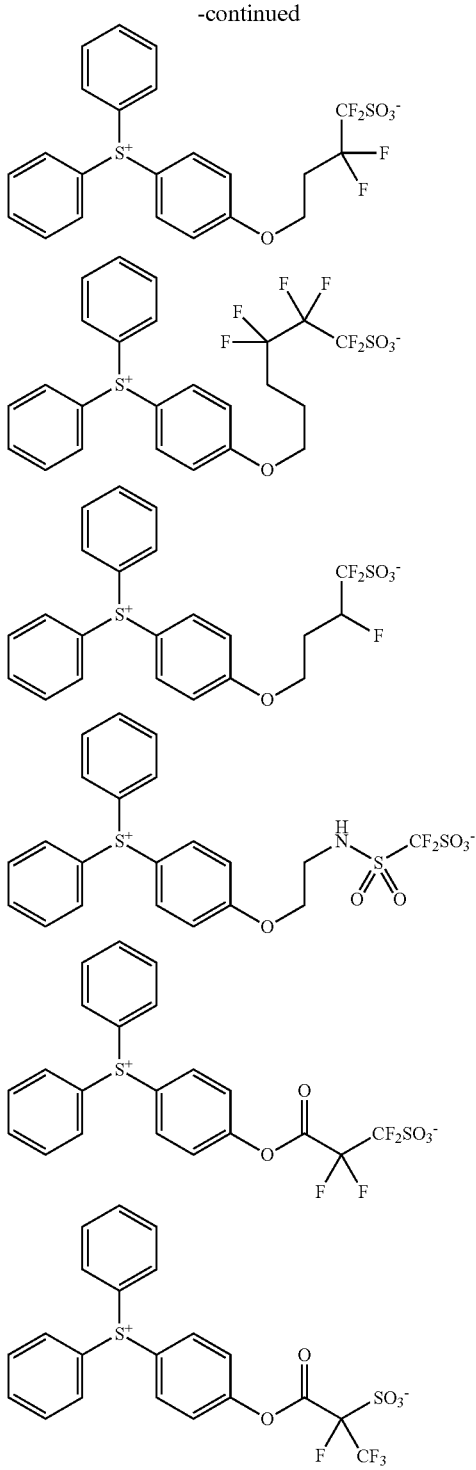

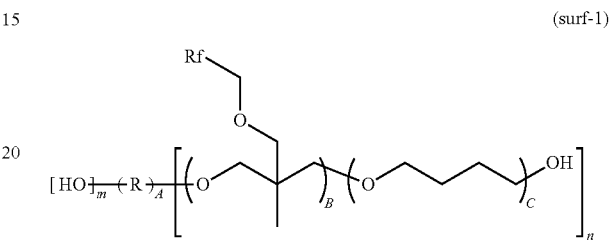

and soluble in alkaline developer, and/or a surfactant which is insoluble or substantially insoluble in water and alkaline developer. For the surfactant (F), reference should be made to those compounds described in JP-A 2010-215608 and JP-A 2011-016746.

While many examples of the surfactant which is insoluble or substantially insoluble in water and alkaline developer are described in the patent documents cited herein, preferred examples are FC-4430, Surflon® S-381, Surfynol E1004, KH-20 and KH-30, which may be used alone or in admixture. Partially fluorinated oxetane ring-opened polymers having the formula (surf-1) are also useful.

(surf-1)

$$[HO\!\!-\!\!]_m\!(R)_A\!\!\left[\!\left(O\diagdown\!\!\diagup\right)_{\!\!B}\!\!\left(O\diagdown\diagdown\diagup\right)_{\!\!C}\!\right]_{\!n}$$

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

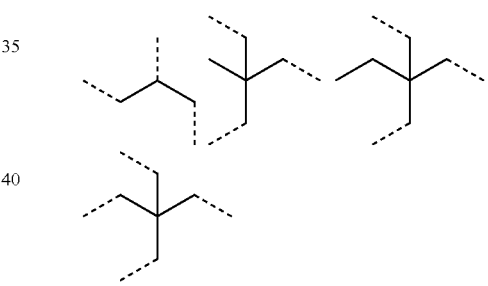

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on An amount of the other PAG (E) used is 0 to 40 parts, and when added, preferably 0.1 to 40 parts, more preferably 0.1 to 20 parts by weight per 100 parts by weight of the base resin (B). An amount in the range ensures good resolution and leaves no foreign particles after resist development or during stripping. The PAG (E) may be used alone or in admixture of two or more.

(F) Surfactant

The resist composition may further comprise (F) a surfactant which is insoluble or substantially insoluble in water the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage.

Suitable polymeric surfactants include those comprising recurring units of at least one type selected from the formulae (5A) to (5E).

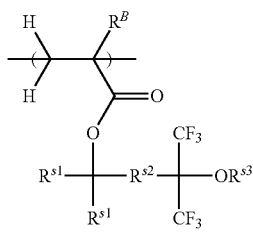

(5A)

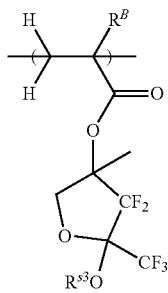

(5B)

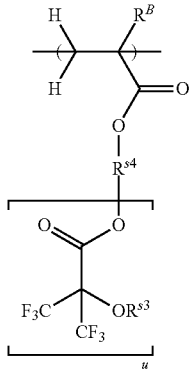

(5C)

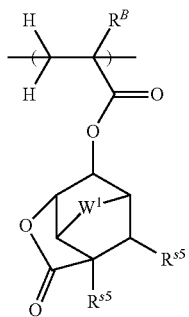

(5D)

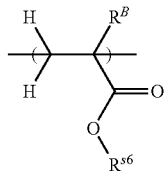

(5E)

Herein, $R^B$ is hydrogen, fluorine, methyl or trifluoromethyl. $W^1$ is —CH$_2$—, —CH$_2$CH$_2$— or —O—, or two separate —H. $R^{s1}$ is each independently hydrogen or a $C_1$-$C_{10}$ monovalent hydrocarbon group. $R^{s2}$ is a single bond or a $C_1$-$C_5$ straight or branched divalent hydrocarbon group. $R^{s3}$ is each independently hydrogen, a $C_1$-$C_{15}$ monovalent hydrocarbon or fluorinated hydrocarbon group, or an acid labile group. When $R^{s3}$ is a monovalent hydrocarbon or fluorinated hydrocarbon group, an ether bond (—O—) or carbonyl moiety (—C(=O)—) may intervene in a carbon-carbon bond. $R^{s4}$ is a $C_1$-$C_{20}$ (u+1)-valent hydrocarbon or fluorinated hydrocarbon group, and u is an integer of 1 to 3. $R^{s5}$ is each independently hydrogen or a group having the formula:

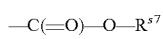

—C(=O)—O—$R^{s7}$ wherein $R^{s7}$ is a $C_1$-$C_{20}$ fluorinated hydrocarbon group. $R^6$ is a $C_1$-$C_{15}$ monovalent hydrocarbon or fluorinated hydrocarbon group in which an ether bond (—O—) or carbonyl moiety (—C(=O)—) may intervene in a carbon-carbon bond.

The monovalent hydrocarbon group represented by $R^{s1}$ may be straight, branched or cyclic and examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, cyclohexyl, n-heptyl, n-octyl, n-nonyl, n-decyl, adamantyl, and norbomyl. Inter alia, $C_1$-$C_6$ hydrocarbon groups are preferred.

The divalent hydrocarbon group represented by $R^{s2}$ may be straight, branched or cyclic and examples thereof include methylene, ethylene, propylene, butylene, and pentylene.

The monovalent hydrocarbon group represented by $R^{s3}$ or $R^{s6}$ may be straight, branched or cyclic and examples thereof include alkyl, alkenyl, and alkynyl groups, with the alkyl groups being preferred. Suitable alkyl groups include those exemplified for the monovalent hydrocarbon group represented by $R^{s1}$ as well as n-undecyl, n-dodecyl, tridecyl, tetradecyl, and pentadecyl. Examples of the monovalent fluorinated hydrocarbon group represented by $R^{s3}$ or $R^{s6}$ include the foregoing monovalent hydrocarbon groups in which some or all carbon-bonded hydrogen atoms are substituted by fluorine atoms. In these groups, an ether bond (—O—) or carbonyl moiety (—C(=O)—) may intervene in a carbon-carbon bond as mentioned above.

Examples of the acid labile group represented by $R^{s3}$ include groups of the above formulae (L1) to (L4), $C_4$-$C_{20}$, preferably $C_4$-$C_{15}$ tertiary alkyl groups, trialkylsilyl groups in which each alkyl moiety has 1 to 6 carbon atoms, and $C_4$-$C_{20}$ oxoalkyl groups.

The (u+1)-valent hydrocarbon or fluorinated hydrocarbon group represented by $R^{s4}$ may be straight, branched or cyclic and examples thereof include the foregoing monovalent hydrocarbon or fluorinated hydrocarbon groups from which the number (u) of hydrogen atoms are eliminated.

The fluorinated hydrocarbon group represented by $R^{s7}$ may be straight, branched or cyclic and examples thereof include the foregoing monovalent hydrocarbon groups in which some or all hydrogen atoms are substituted by fluorine atoms. Illustrative examples include trifluoromethyl, 2,2,2-trifluoroethyl, 3,3,3-trifluoro-1-propyl, 3,3,3-trifluoro-2-propyl, 2,2,3,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7-dodecafluoroheptyl, 2-(perfluorobutyl)ethyl, 2-(perfluorohexyl)ethyl, 2-(perfluorooctyl)ethyl, and 2-(perfluorodecyl)ethyl.

Examples of the recurring units having formulae (5A) to (5E) are shown below, but not limited thereto. Herein $R^B$ is as defined above.

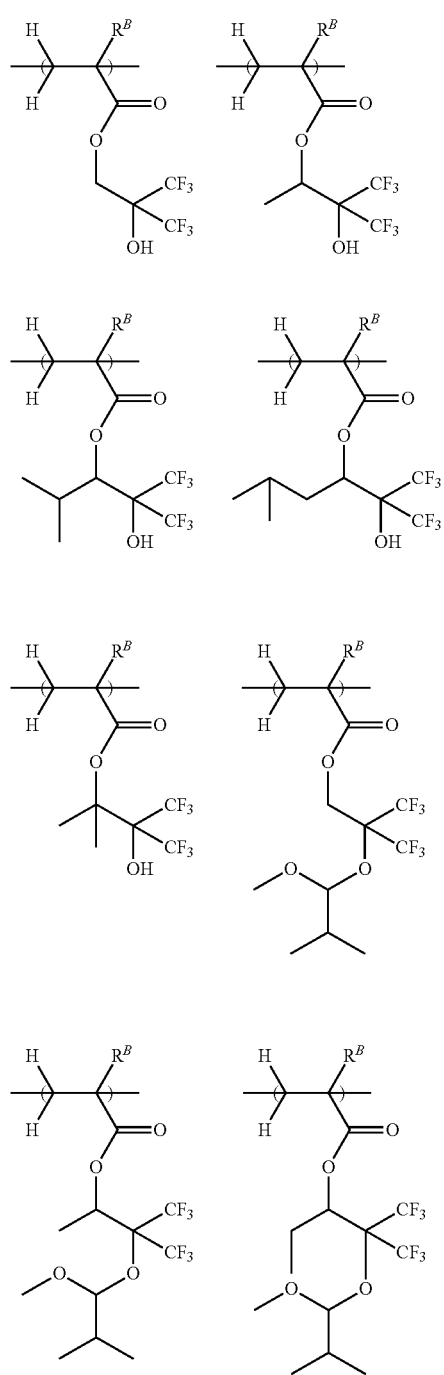

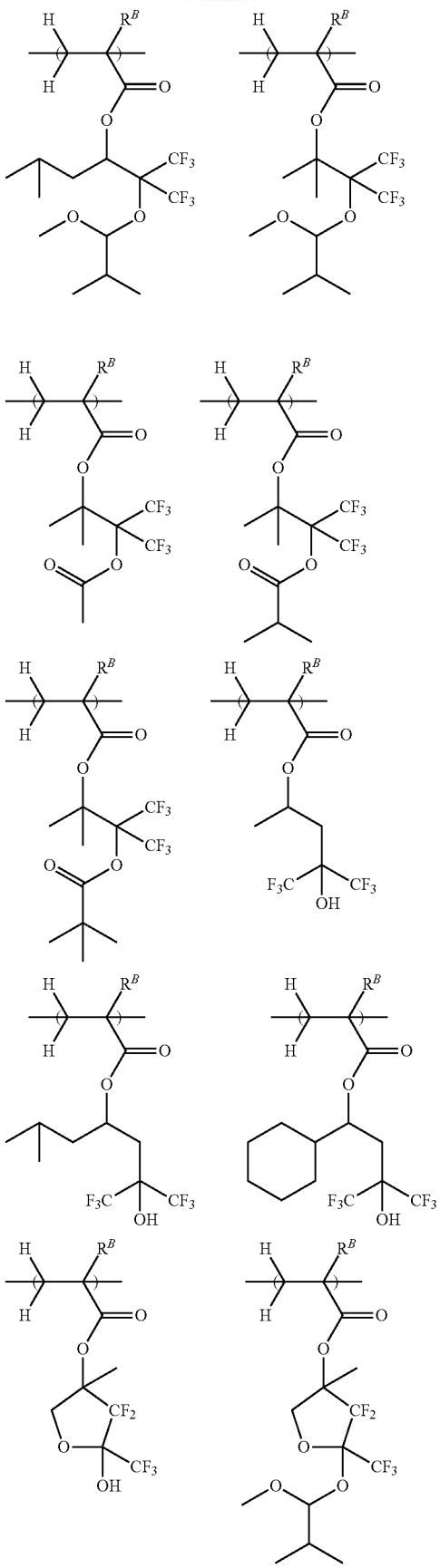

127
-continued
128
-continued
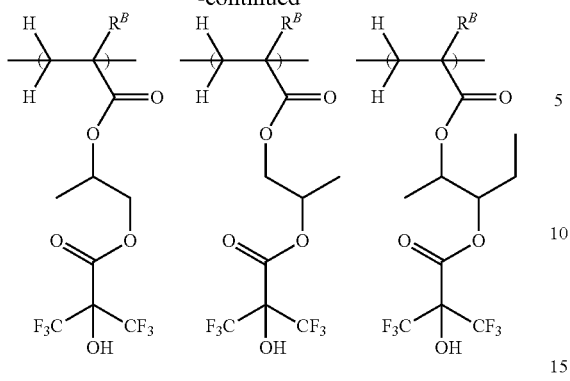
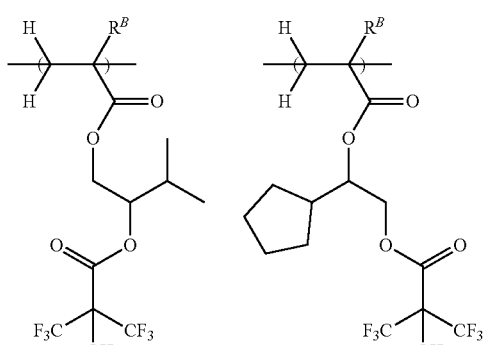
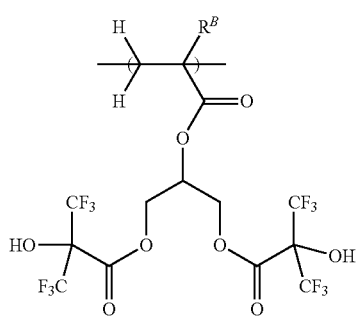
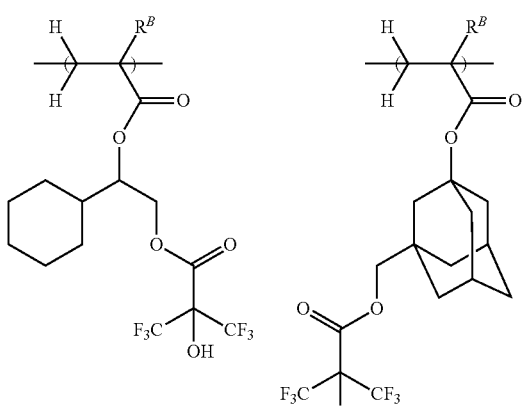
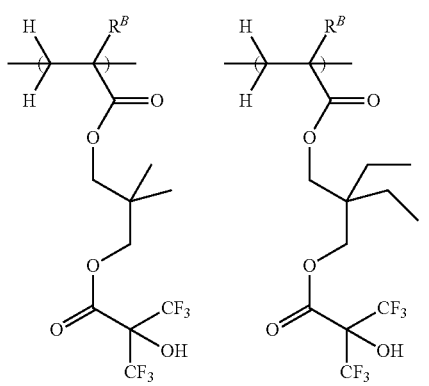
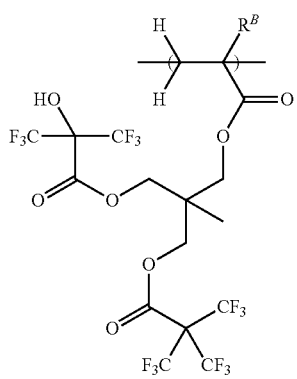

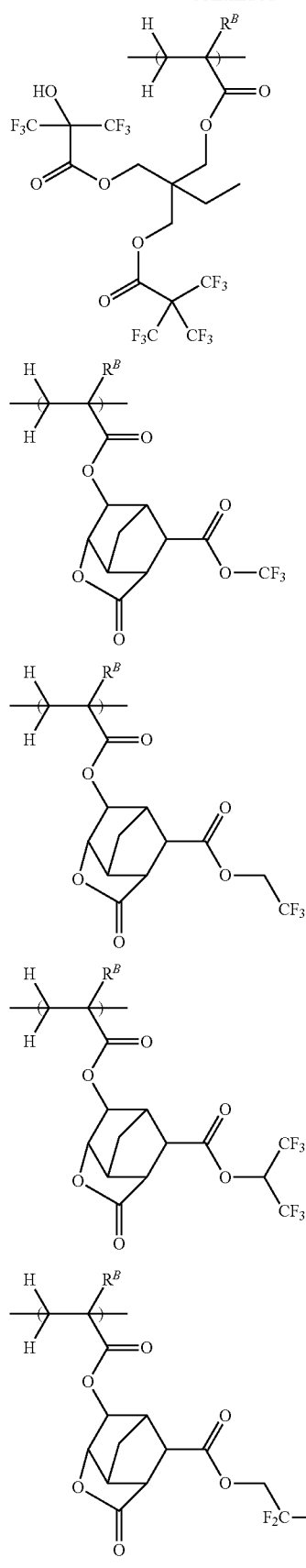
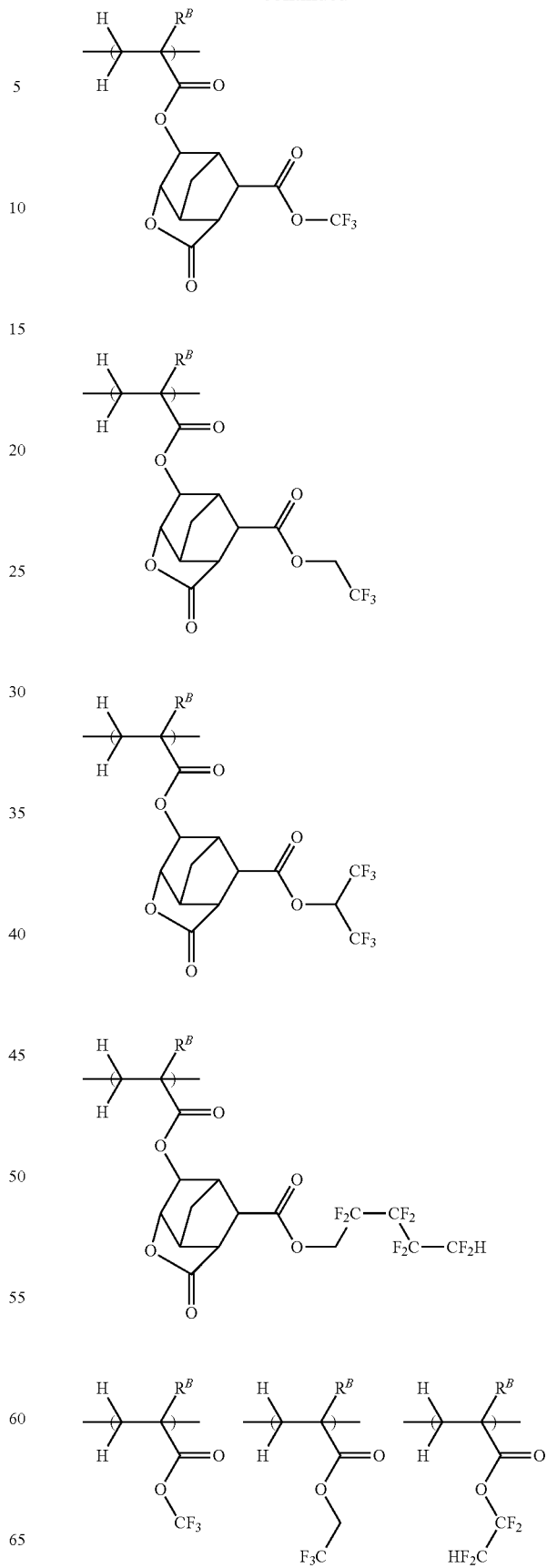

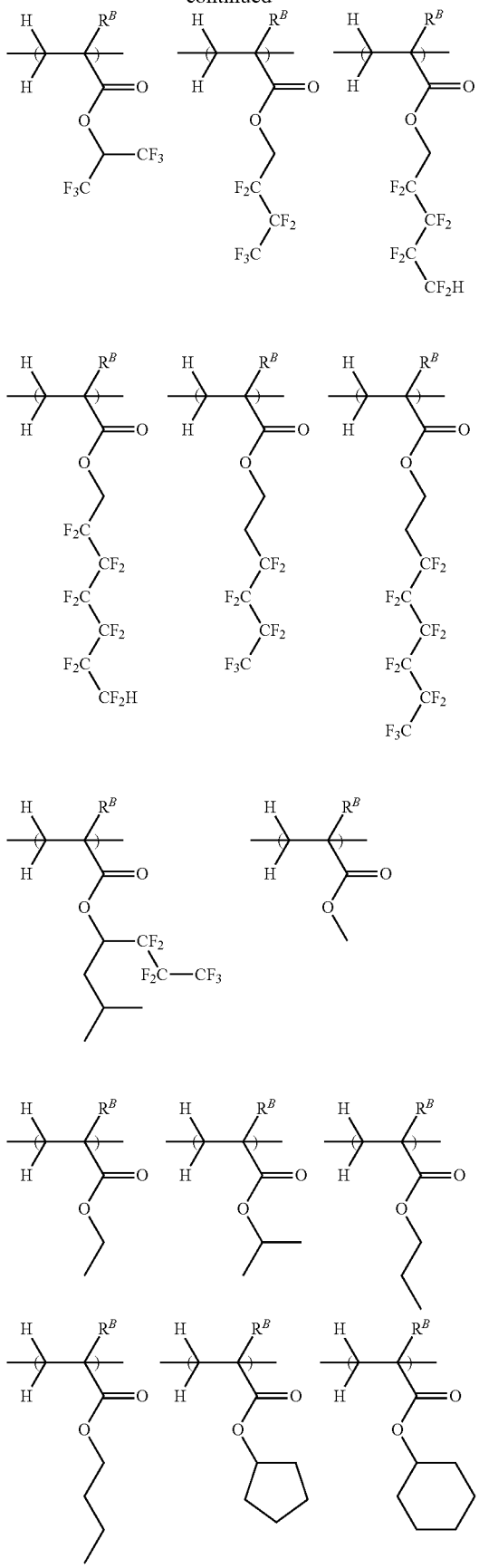

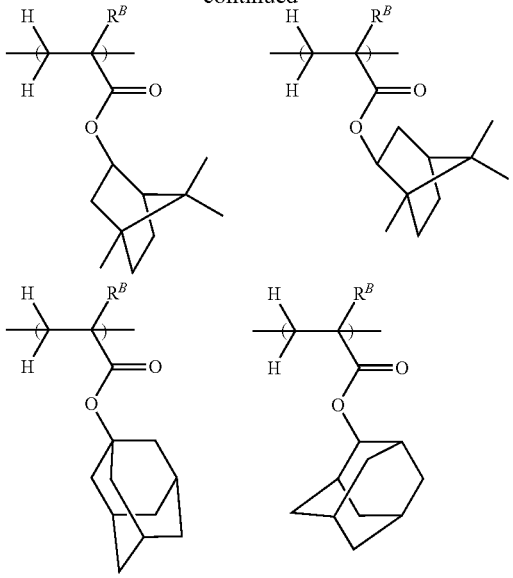

The polymeric surfactant preferably has a Mw of 1,000 to 500,000, more preferably 2,000 to 20,000. As long as Mw is in the range, a sufficient surface modifying effect may be exerted and development defects may be avoided.

For the surfactant which is insoluble or substantially insoluble in water and soluble in alkaline developer, reference may be made to JP-A 2008-122932, 2009-098638, 2009-191151, 2009-192784, 2009-276363, 2010-107695, 2010-134012, 2010-250105, and 2011-042789.

An appropriate amount of component (F) is 0 to 20 parts by weight per 100 parts by weight of the base resin (B). When used, the amount of component (F) is preferably at least 0.001 part, more preferably at least 0.01 part by weight and preferably up to 15 parts, more preferably up to 10 parts by weight.

Process

A further embodiment of the invention is a pattern forming process using the resist composition defined above. The preferred process includes the steps of applying the resist composition onto a substrate to form a resist film, exposing a selected region of the resist film to KrF excimer laser, ArF excimer laser, EB or EUV, and developing the exposed resist film in a developer. Any desired steps may be added to the process if necessary.

The substrate used herein may be a substrate for integrated circuitry fabrication, e.g., Si, $SiO_2$, SiN, SiON, TiN, WSi, BPSG, SOG, organic antireflective film, etc. or a substrate for mask circuitry fabrication, e.g., Cr, CrO, CrON, $MoSi_2$, $SiO_2$, etc.

The resist composition is applied onto a substrate by a suitable coating technique such as spin coating. The coating is prebaked on a hot plate preferably at a temperature of 60 to 150° C. for 1 to 10 minutes, more preferably at 80 to 140° C. for 1 to 5 minutes. The resulting resist film preferably has a thickness of 0.05 to 2 μm.

Then the resist film is exposed patternwise to excimer laser, EUV or EB. On use of KrF excimer laser, ArF excimer laser or EUV of wavelength 13.5 nm, the resist film is exposed through a mask having a desired pattern, preferably in a dose of 1 to 200 mJ/cm², more preferably 10 to 100 mJ/cm². On use of EB, a pattern may be written directly or through a mask having the desired pattern, preferably in a dose of 1 to 300 µC/cm², more preferably 10 to 200 µC/cm².

The exposure may be performed by conventional lithography whereas the immersion lithography may be employed if desired. In the immersion lithography, a liquid having a refractive index of at least 1.0 is held between the resist film and the projection lens. The liquid is typically water, and in this case, a protective film which is insoluble in water may be formed on the resist film.

While the water-insoluble protective film which is used in the immersion lithography serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB), for example, on a hotplate at 60 to 150° C. for 1 to 5 minutes, preferably at 80 to 140° C. for 1 to 3 minutes.

The resist film is then developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

Any desired step may be added to the pattern forming process. For example, after the resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also, a double patterning process may be used for pattern formation. The double patterning process includes a trench process of processing an underlay to a 1:3 trench pattern by a first step of exposure and etching, shifting the position, and forming a 1:3 trench pattern by a second step of exposure, for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, negative tone development may also be used. That is, an organic solvent may be used instead of the aqueous alkaline solution as the developer for developing and dissolving away the unexposed region of the resist film.

The organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLES

Synthesis Examples, Examples and Comparative Examples are given below by way of illustration and not by way of limitation. The abbreviation "pbw" is parts by weight. For all polymers, Mw and Mn are determined by GPC versus polystyrene standards using THF solvent. THF stands for tetrahydrofuran, and PGMEA for propylene glycol monomethyl ether acetate. Analysis is made by IR spectroscopy, $^1$H- and $^{19}$F-NMR spectroscopy, and time-of-flight mass spectrometry (TOF-MS) using analytic instruments as shown below.

IR: NICOLET 6700 by Thermo Fisher Scientific Inc.
$^1$H-NMR: ECA-500 by JEOL Ltd.
$^{19}$F-NMR: ECA-500 by JEOL Ltd.
MALDI-TOF-MS: S3000 by JEOL Ltd.

[1] Synthesis of Salt Compounds

Example 1-1

Synthesis of PAG-1

Example 1-1-1

Synthesis of Intermediate A

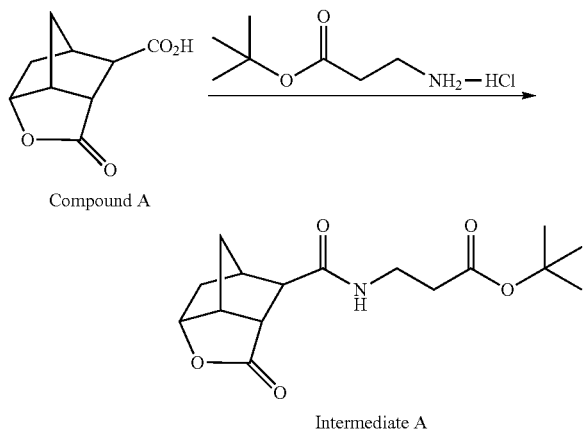

Compound A

Intermediate A

In 100 g of dichloromethane was dissolved 18 g of Compound A. To this solution, 20 g of β-alanine tert-butyl ester hydrochloride, 21 g of 1-ethyl-3-(3-dimethylaminopropyl)carbodiimide hydrochloride, and 20 g of N,N-dimethylaminopyridine were added. The solution was stirred at room temperature overnight. After the solution was ice cooled, 30 g of deionized water and 30 g of 10 wt % hydrochloric acid were added thereto to quench the reaction. The organic layer was washed with water. After separation, the organic layer was concentrated, obtaining 30 g of the desired compound, Intermediate A as brown oily matter. The compound was used in the subsequent step without further purification.

Example 1-1-2

Synthesis of Intermediate B

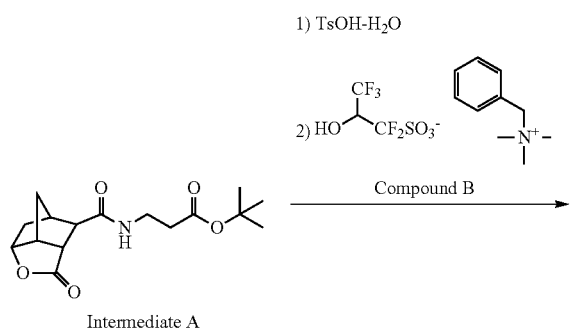

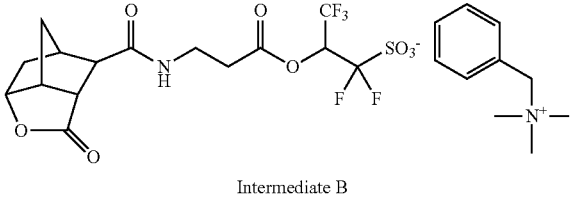

Intermediate B

To a solution of 30 g of Intermediate A in 100 g of acetonitrile, 2 g of p-toluenesulfonic acid monohydrate was added. The solution was heated at 80° C. and stirred overnight under reflux conditions. Then 37 g of Compound B, 22 g of 1-ethyl-3-(3-dimethylaminopropyl)carbodiimide hydrochloride, and 2 g of N,N-dimethylaminopyridine were added. The solution was stirred overnight, after which 100 g of dichloromethane and 30 g of deionized water were added to quench the reaction. The organic layer was washed with water, combined with 30 g of 10 wt % hydrochloric acid, and washed with water again. The resulting organic layer was concentrated in vacuum, obtaining an oily matter. This was followed by decantation using diisopropyl ether (DIPE) and vacuum concentration again, obtaining 30 g of the desired compound, Intermediate B (yield 68%).

Example 1-1-3

Synthesis of PAG-1

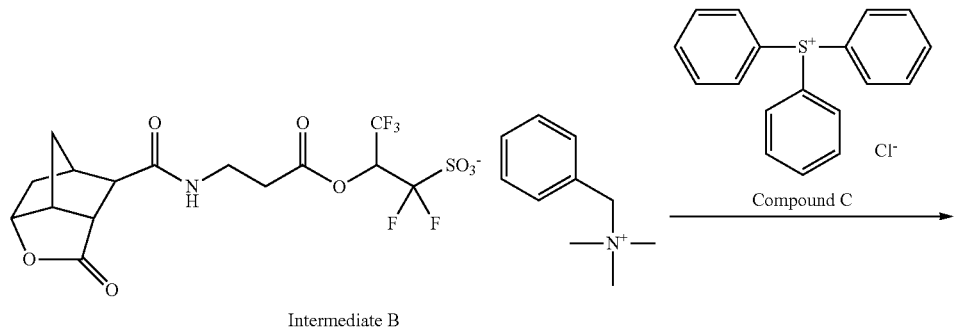

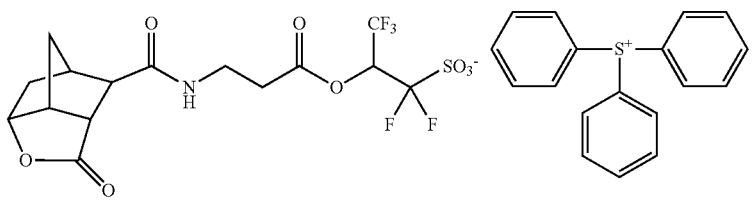

PAG-1

To a solution of 30 g of Intermediate B in 100 g of dichloromethane, 60 mL of a 10 wt % aqueous solution of Compound C was added. The solution was stirred for 1 hour and then separated. The organic layer was washed 5 times with deionized water. The organic layer was concentrated in vacuum, obtaining an oily matter. This was followed by decantation using DIPE and vacuum concentration again, obtaining 35 g of the target compound, PAG-1 (yield 91%).

The target compound was analyzed by IR spectroscopy and TOF-MS, with the data shown below. FIG. 1 is the $^1$H-NMR/DMSO-$d_6$ spectrum of the target compound.

IR (D-ATR): v=3502, 3321, 3066, 2971, 1767, 1666, 1542, 1477, 1448, 1370, 1319, 1266, 1243, 1173, 1088, 1073, 1033, 990, 930, 910, 842, 750, 684, 642, 596, 553 cm$^{-1}$

MALDI TOF-MS
Positive M$^+$ 263 (corresponding to $C_{18}H_{15}S^+$)
Negative M$^-$ 464 (corresponding to $C_{15}H_{15}F_5NO_8S^-$)

Example 1-2

Synthesis of PAG-2

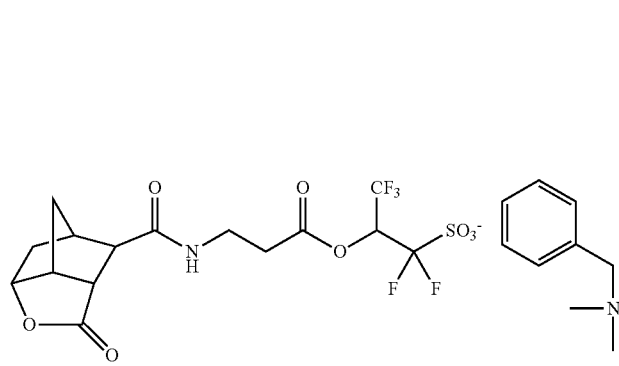

Intermediate B

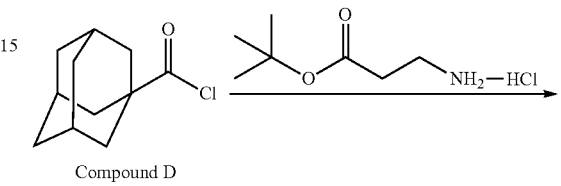

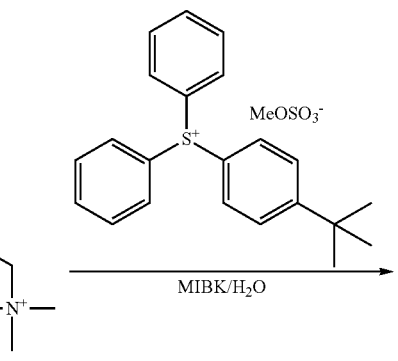

PAG-2

The same procedure as in Example 1-1-3 was followed aside from using 100 mL of a 10 wt % aqueous solution of (4-tert-butylphenyl)diphenylsulfonium methylsulfate instead of the aqueous solution of Compound C. There was obtained 37.8 g of PAG-2 as an oily matter (yield 99%).

Figure 2:
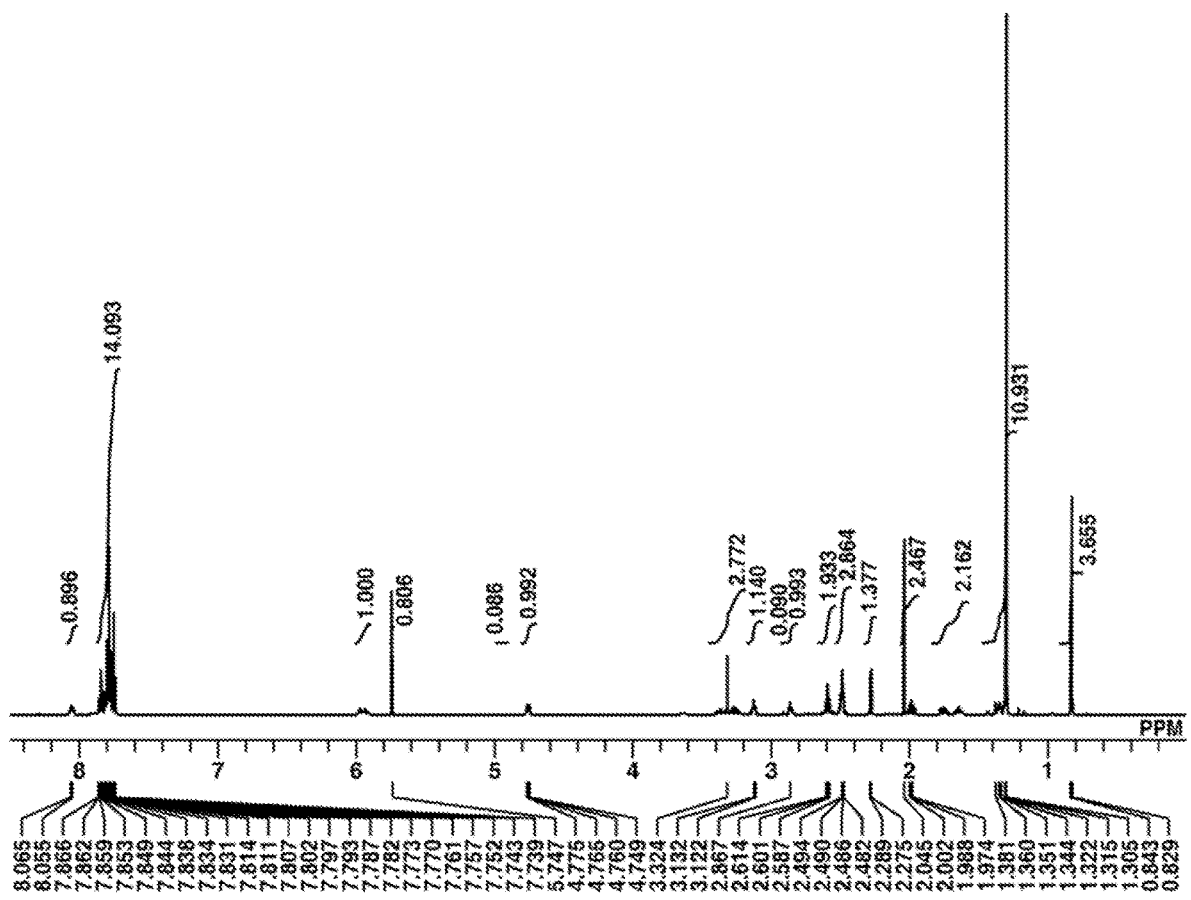
FIG. 2 is a diagram showing $^1$H-NMR spectrum of the compound in Example 1-2.

The target compound was analyzed by IR spectroscopy and TOF-MS, with the data shown below. FIG. 2 is the $^1$H-NMR/DMSO-$d_6$ spectrum of the target compound.

IR (D-ATR): v=3314, 3064, 2965, 2873, 1770, 1705, 1669, 1589, 1544, 1491, 1478, 1447, 1402, 1367, 1318, 1298, 1267, 1243, 1218, 1181, 1140, 1114, 1088, 1073, 1033, 990, 928, 909, 891, 874, 840, 751, 684, 642, 592, 554, 524 cm$^{-1}$

MALDI TOF-MS
Positive M$^+$ 319 (corresponding to $C_{22}H_{23}S^+$)
Negative M$^-$ 464 (corresponding to $C_{15}H_{15}F_5NO_8S^-$)

Example 1-3

Synthesis of PAG-3

Example 1-3-1

Synthesis of Intermediate C

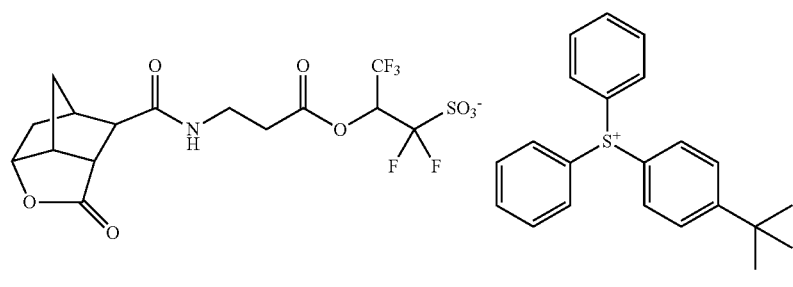

Compound D

-continued

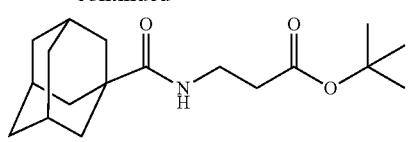

Intermediate C

Intermediate C was synthesized by the same procedure as in Example 1-1-1 aside from using Compound D as the starting reactant.

Example 1-3-2

Synthesis of PAG-3

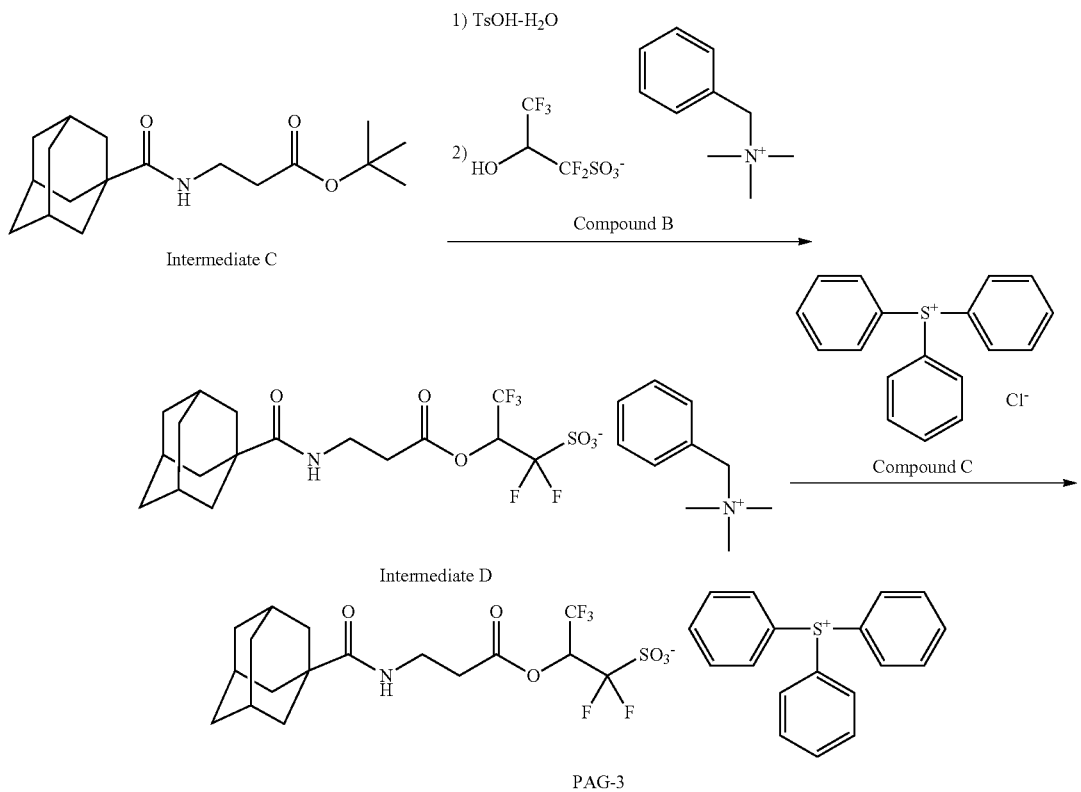

The same procedure as in Examples 1-1-2 and 1-1-3 was followed aside from using Intermediate C as the reactant. There was obtained PAG-3 (yield 67%).

Figure 3:
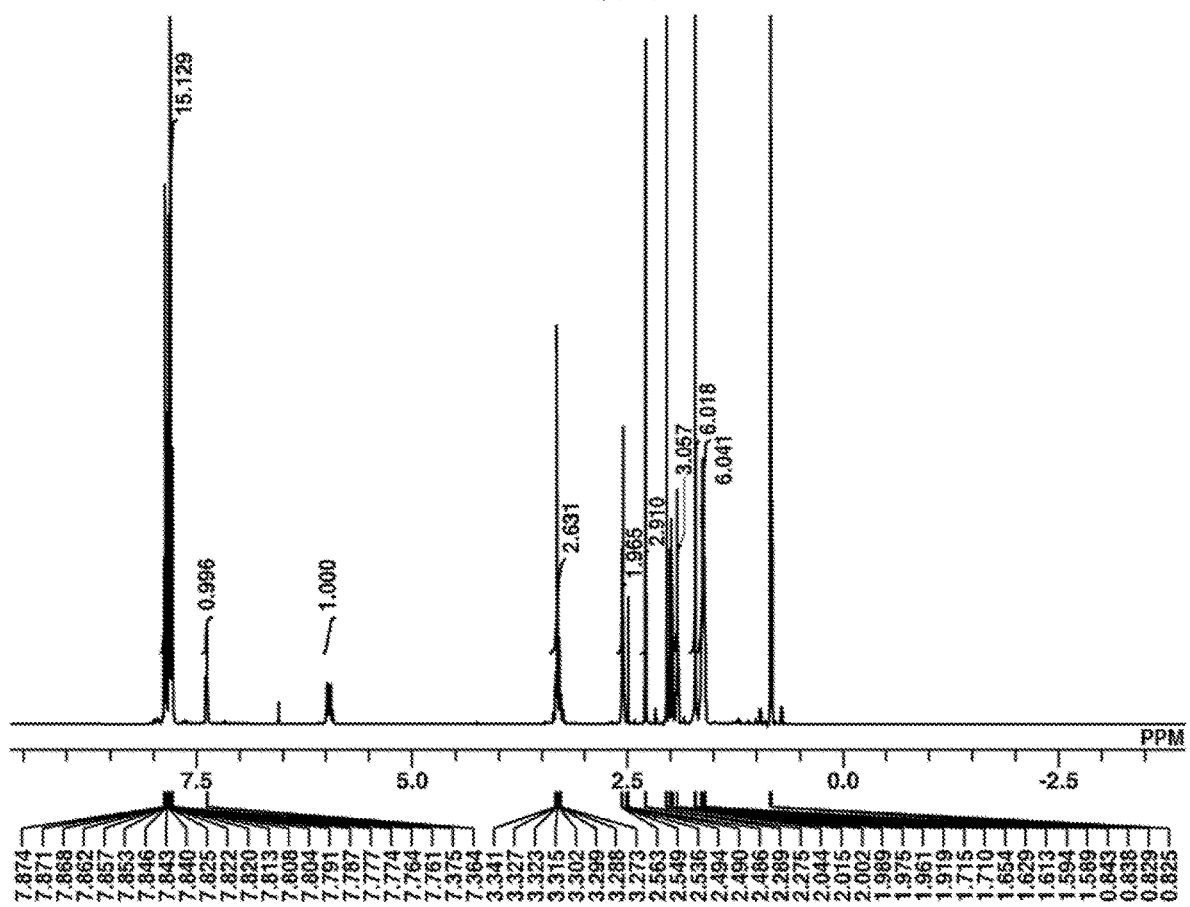
FIG. 3 is a diagram showing $^1$H-NMR spectrum of the compound in Example 1-3.

The target compound was analyzed by IR spectroscopy and TOF-MS, with the data shown below. FIG. 3 is the $^1$H-NMR/DMSO-$d_6$ spectrum of the target compound.

IR (D-ATR): ν=3363, 3063, 2905, 2851, 2658, 1770, 1645, 1581, 1525, 1477, 1448, 1370, 1330, 1265, 1247, 1183, 1171, 1118, 1091, 1074, 1023, 996, 910, 841, 750, 684, 642, 592, 553 cm$^{-1}$

MALDI TOF-MS

Positive M$^+$ 263 (corresponding to $C_{18}H_{15}S^+$)

Negative M$^-$ 462 (corresponding to $C_{17}H_{21}F_5NO_6S^-$)

Example 1-4

Synthesis of PAG-4

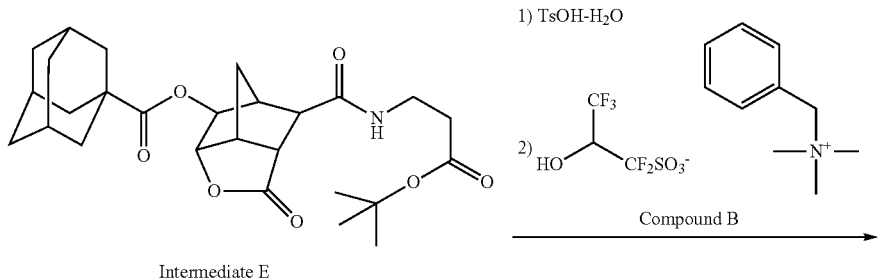

-continued

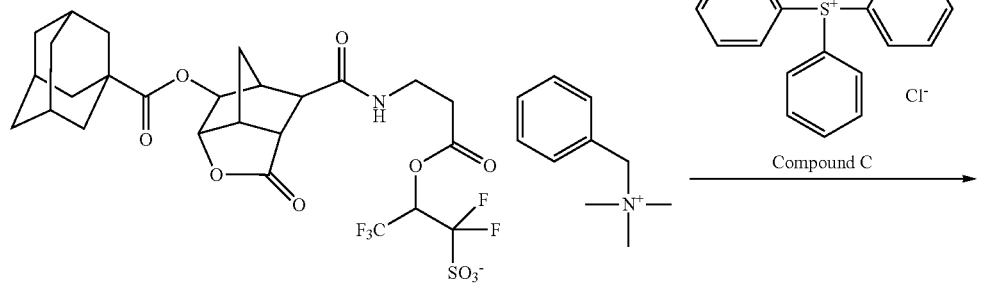

Intermediate F

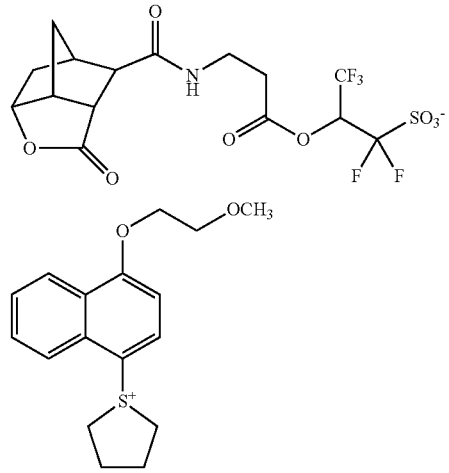

PAG-4

The same procedure as in Examples 1-1-2 and 1-1-3 was followed except that Intermediate E was used as the reactant. There was obtained PAG-4 (yield 74%).

Figure 4:
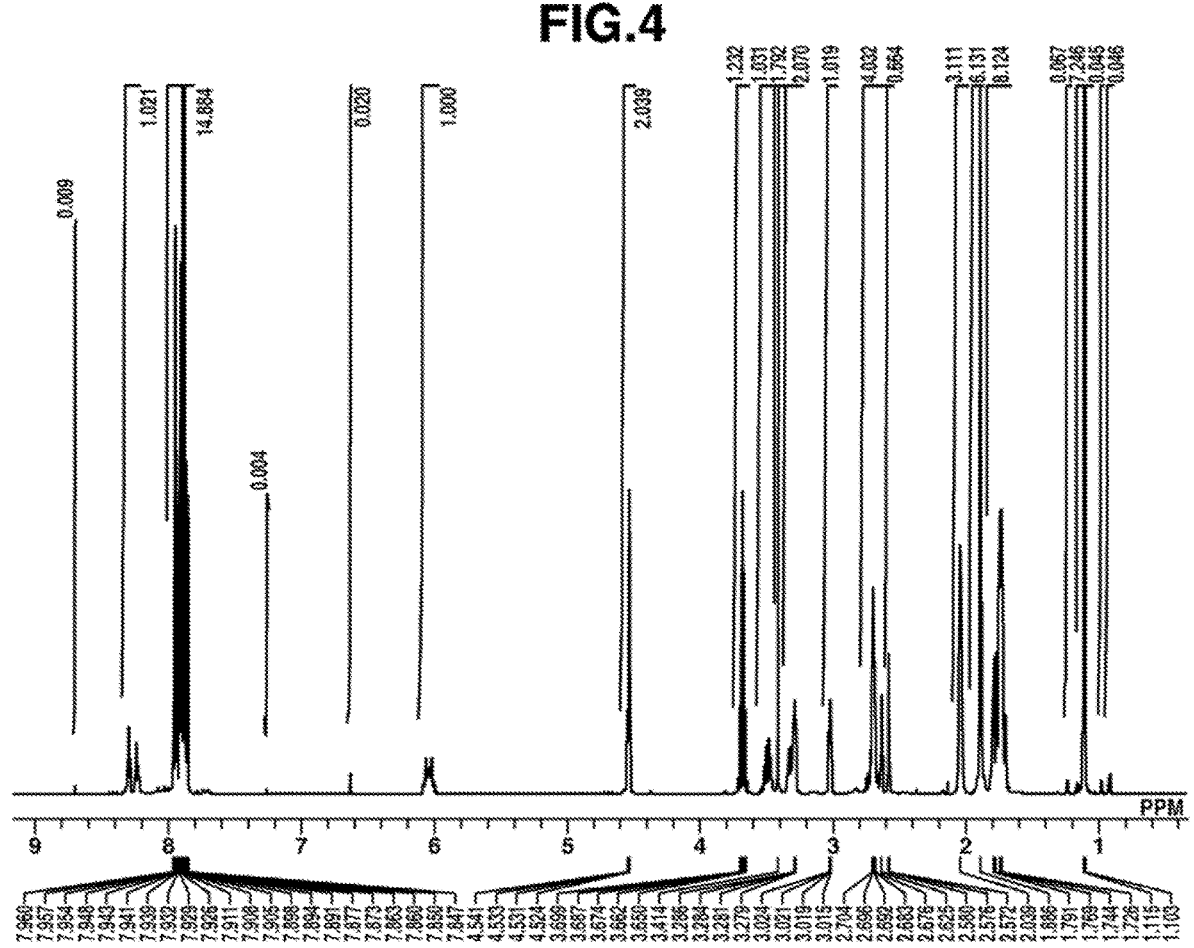
FIG. 4 is a diagram showing $^1$H-NMR spectrum of the compound in Example 1-4.

The target compound was analyzed by IR spectroscopy and TOF-MS, with the data shown below. FIG. 4 is the $^1$H-NMR/DMSO-$d_6$ spectrum of the target compound.

IR (D-ATR): ν=3310, 3066, 2972, 2908, 2853, 1778, 1727, 1672, 1545, 1477, 1448, 1369, 1326, 1270, 1240, 1172, 1104, 1077, 1038, 1010, 997, 937, 909, 842, 750, 684, 642, 592, 553 cm$^{-1}$

MALDI TOF-MS

Positive M$^+$ 263 (corresponding to $C_{18}H_{15}S^+$)
Negative M$^-$ 642 (corresponding to $C_{26}H_{29}F_5NO_{10}S^-$)

Examples 1-5 to 1-14

Synthesis of PAG-5 to PAG-14

PAG-5 to PAG-14 were synthesized by a well-known organic synthesis method using corresponding reactants.

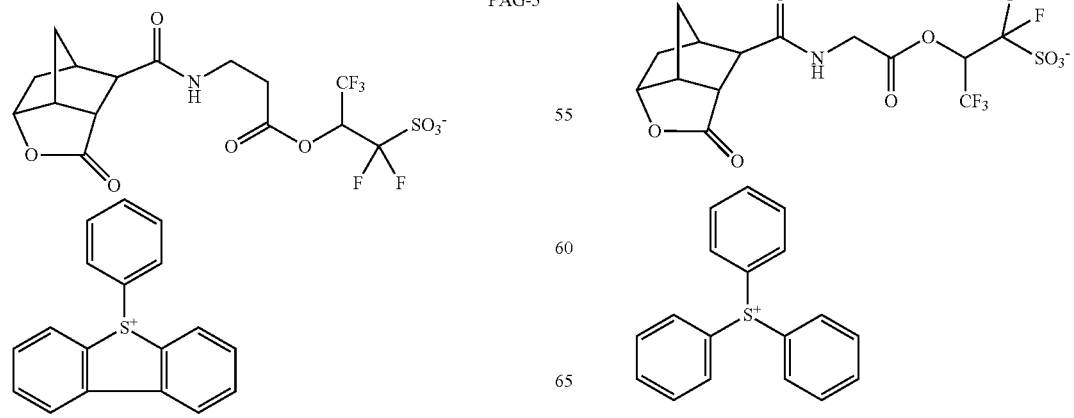

-continued

PAG-8
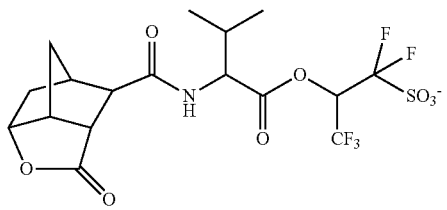

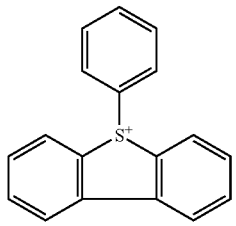

PAG-9

PAG-10
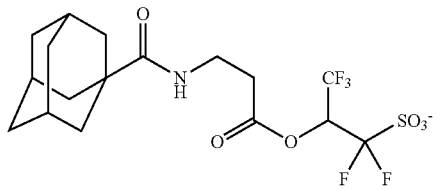

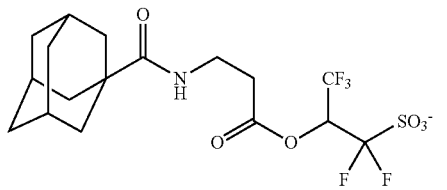

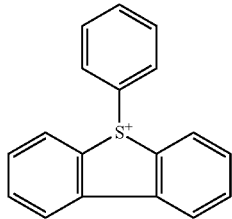

PAG-11
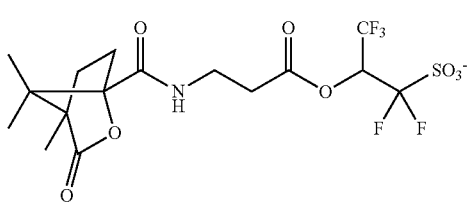

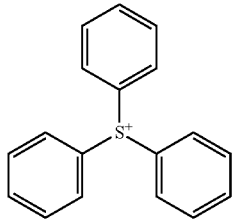

-continued

PAG-12
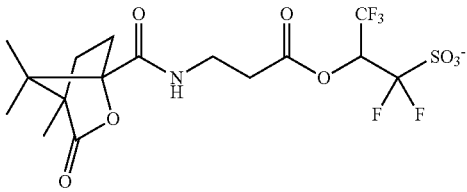

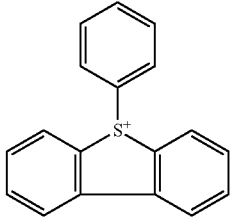

PAG-13
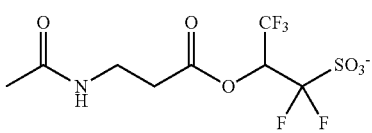

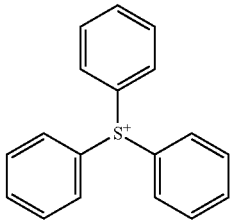

PAG-14
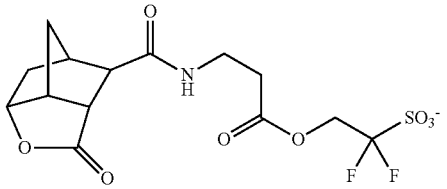

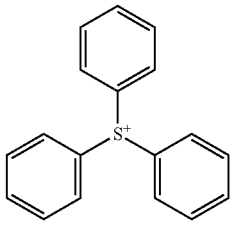

[2] Synthesis of Polymers

Polymers used in resist compositions within the scope of the invention were synthesized by the following procedure.

Synthesis Example 1

Synthesis of Polymer P-1

In a funnel under nitrogen atmosphere, 4.7 g of 3-hydroxy-1-adamantyl methacrylate, 6.7 g of α-methacryloxy-γ-butyrolactone, 5.4 g of 3-ethyl-3-exo-tetracyclo[4.4.0.$1^{2,5}.1^{7,10}$]dodecyl methacrylate, 14.4 g of 1-ethylcyclopentyl methacrylate, 8.8 g of 4,8-dioxatricyclo[4.2.1.0$^{3,7}$] nonan-5-on-2-yl methacrylate, 0.45 g of dimethyl 2,2'-azobis(2-methylpropionate) (V-601 by Wako Pure Chemical Industries, Ltd.), 0.39 g of 2-mercaptoethanol, and 56 g of PGMEA were combined to form a monomer/initiator solution. A flask in nitrogen atmosphere was charged with 19 g of PGMEA, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining Polymer P-1 in white powder form (amount 35.3 g, yield 88%). On GPC analysis, Polymer P-1 had a Mw of 8,100 and a Mw/Mn of 1.73.

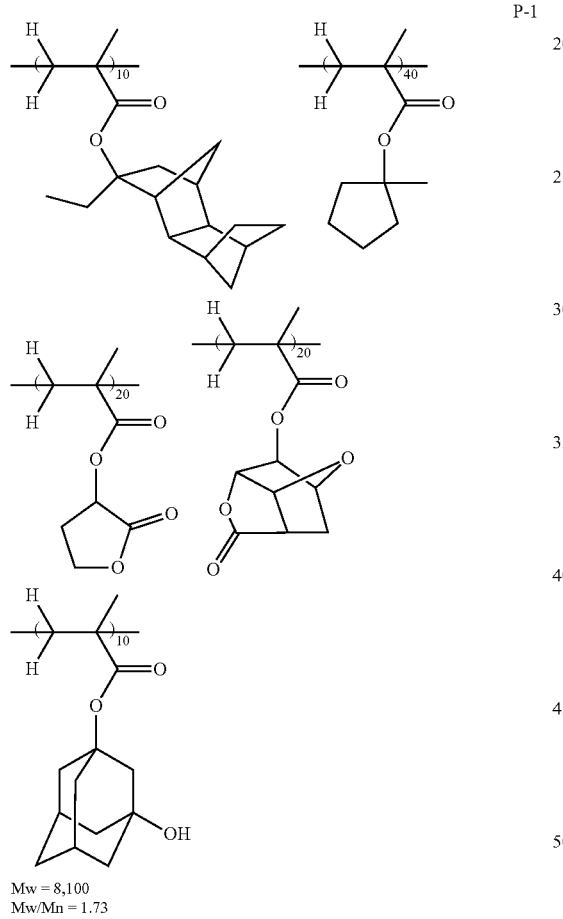

Synthesis Example 2

Synthesis of Polymer P-2

Polymers P-2 was synthesized by the same procedure as in Synthesis Example 1 aside from changing the type and amount of monomers. Polymer P-2 had a Mw of 8,500 and a Mw/Mn of 1.58.

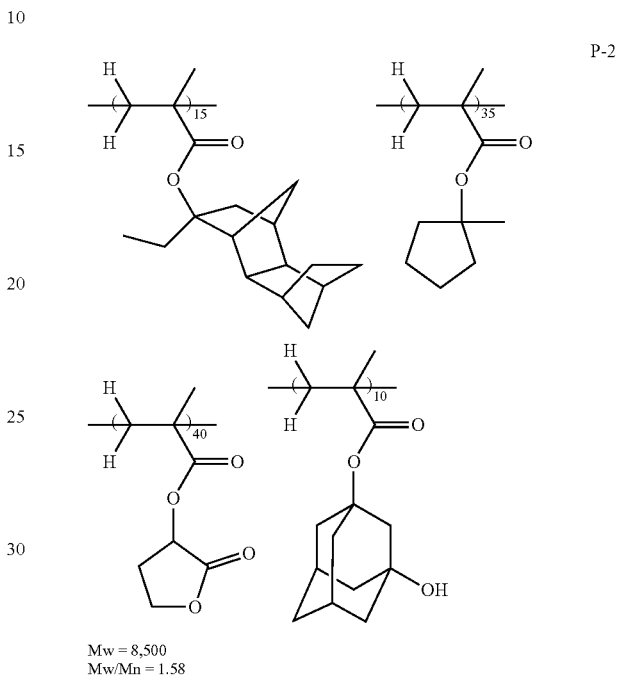

[3] Preparation of Chemically Amplified Resist Composition

Examples 2-1 to 2-28 and Comparative Examples 1-1 to 1-12

Chemically amplified resist compositions in solution form were prepared by dissolving a salt (PAG-1 to PAG-14) or comparative photoacid generator (PAG-A to PAG-F), polymer (P-1 or P-2), quencher (Q-1 to Q-4), and alkali-soluble surfactant (SF-1) in a solvent containing 0.01 wt % of surfactant A in accordance with the formulation shown in Tables 1 and 2, and filtering through a Teflon® filter with a pore size of 0.2 μm.

TABLE 1

| | | Resist composition | Polymer (pbw) | Photoacid generator (pbw) | Quencher (pbw) | Surfactant (pbw) | Solvent 1 (pbw) | Solvent 2 (pbw) |
|---|---|---|---|---|---|---|---|---|
| Example | 2-1 | R-01 | P-1 (80) | PAG-1 (6.0) | Q-1 (3.0) | SF-1 (3.0) | PGMEA (1,728) | GBL (192) |
| | 2-2 | R-02 | P-1 (80) | PAG-2 (6.0) | Q-1 (3.0) | SF-1 (3.0) | PGMEA (1,728) | GBL (192) |
| | 2-3 | R-03 | P-1 (80) | PAG-3 (6.0) | Q-1 (3.0) | SF-1 (3.0) | PGMEA (1,728) | GBL (192) |
| | 2-4 | R-04 | P-1 (80) | PAG-4 (6.0) | Q-1 (3.0) | SF-1 (3.0) | PGMEA (1,728) | GBL (192) |
| | 2-5 | R-05 | P-1 (80) | PAG-5 (6.0) | Q-1 (3.0) | SF-1 (3.0) | PGMEA (1,728) | GBL (192) |
| | 2-6 | R-06 | P-1 (80) | PAG-6 (6.0) | Q-1 (3.0) | SF-1 (3.0) | PGMEA (1,728) | GBL (192) |
| | 2-7 | R-07 | P-1 (80) | PAG-7 (6.0) | Q-1 (3.0) | SF-1 (3.0) | PGMEA (1,728) | GBL (192) |
| | 2-8 | R-08 | P-1 (80) | PAG-8 (6.0) | Q-1 (3.0) | SF-1 (3.0) | PGMEA (1,728) | GBL (192) |

TABLE 1-continued

|  | Resist composition | Polymer (pbw) | Photoacid generator (pbw) | Quencher (pbw) | Surfactant (pbw) | Solvent 1 (pbw) | Solvent 2 (pbw) |
|---|---|---|---|---|---|---|---|
| 2-9 | R-09 | P-1 (80) | PAG-9 (6.0) | Q-1 (3.0) | SF-1 (3.0) | PGMEA (1,728) | GBL (192) |
| 2-10 | R-10 | P-1 (80) | PAG-10 (6.0) | Q-1 (3.0) | SF-1 (3.0) | PGMEA (1,728) | GBL (192) |
| 2-11 | R-11 | P-1 (80) | PAG-11 (6.0) | Q-1 (3.0) | SF-1 (3.0) | PGMEA (1,728) | GBL (192) |
| 2-12 | R-12 | P-1 (80) | PAG-12 (6.0) | Q-4 (3.0) | SF-1 (3.0) | PGMEA (1,728) | GBL (192) |
| 2-13 | R-13 | P-1 (80) | PAG-13 (7.0) | Q-2 (3.5) | SF-1 (3.0) | PGMEA (1,728) | GBL (192) |
| 2-14 | R-14 | P-1 (80) | PAG-14 (6.0) | Q-4 (3.0) | SF-1 (3.0) | PGMEA (1,728) | GBL (192) |
| 2-15 | R-15 | P-2 (80) | PAG-1 (7.0) | Q-1 (3.5) | SF-1 (3.0) | PGMEA (1,728) | GBL (192) |
| 2-16 | R-16 | P-2 (80) | PAG-2 (7.0) | Q-1 (3.5) | SF-1 (3.0) | PGMEA (1,728) | GBL (192) |
| 2-17 | R-17 | P-2 (80) | PAG-3 (7.0) | Q-1 (3.5) | SF-1 (3.0) | PGMEA (1,728) | GBL (192) |
| 2-18 | R-18 | P-2 (80) | PAG-4 (7.0) | Q-1 (3.5) | SF-1 (3.0) | PGMEA (1,728) | GBL (192) |
| 2-19 | R-19 | P-2 (80) | PAG-5 (7.0) | Q-1 (3.5) | SF-1 (3.0) | PGMEA (1,728) | GBL (192) |
| 2-20 | R-20 | P-2 (80) | PAG-6 (7.0) | Q-1 (3.5) | SF-1 (3.0) | PGMEA (1,728) | GBL (192) |
| 2-21 | R-21 | P-2 (80) | PAG-7 (3.0) | Q-1 (3.5) | SF-1 (3.0) | PGMEA (1,728) | GBL (192) |
| 2-22 | R-22 | P-2 (80) | PAG-8 (7.0) | Q-1 (3.5) | SF-1 (3.0) | PGMEA (1,728) | GBL (192) |
| 2-23 | R-23 | P-2 (80) | PAG-9 (7.0) | Q-1 (3.5) | SF-1 (3.0) | PGMEA (1,728) | GBL (192) |
| 2-24 | R-24 | P-2 (80) | PAG-10 (7.0) | Q-1 (3.5) | SF-1 (3.0) | PGMEA (1,728) | GBL (192) |
| 2-25 | R-25 | P-2 (80) | PAG-11 (7.0) | Q-1 (3.5) | SF-1 (3.0) | PGMEA (1,728) | GBL (192) |
| 2-26 | R-26 | P-2 (80) | PAG-12 (7.0) | Q-2 (3.5) | SF-1 (3.0) | PGMEA (1,728) | GBL (192) |
| 2-27 | R-27 | P-2 (80) | PAG-13 (6.0) | Q-3 (3.0) | SF-1 (3.0) | PGMEA (1,728) | GBL (192) |
| 2-28 | R-28 | P-2 (80) | PAG-14 (7.0) | Q-1 (3.5) | SF-1 (3.0) | PGMEA (1,728) | GBL (192) |

TABLE 2

|  |  | Resist composition | Polymer (pbw) | Photoacid generator (pbw) | Quencher (pbw) | Surfactant (pbw) | Solvent 1 (pbw) | Solvent 2 (pbw) |
|---|---|---|---|---|---|---|---|---|
| Comparative Example | 1-1 | R-29 | P-1 (80) | PAG-A (7.0) | Q-1 (3.5) | SF-1 (3.0) | PGMEA (1,728) | GBL (192) |
|  | 1-2 | R-30 | P-1 (80) | PAG-B (7.0) | Q-1 (3.5) | SF-1 (3.0) | PGMEA (1,728) | GBL (192) |
|  | 1-3 | R-31 | P-1 (80) | PAG-C (7.0) | Q-1 (3.5) | SF-1 (3.0) | PGMEA (1,728) | GBL (192) |
|  | 1-4 | R-32 | P-1 (80) | PAG-D (7.0) | Q-1 (3.5) | SF-1 (3.0) | PGMEA (1,728) | GBL (192) |
|  | 1-5 | R-33 | P-1 (80) | PAG-E (7.0) | Q-1 (3.5) | SF-1 (3.0) | PGMEA (1,728) | GBL (192) |
|  | 1-6 | R-34 | P-1 (80) | PAG-F (7.0) | Q-1 (3.5) | SF-1 (3.0) | PGMEA (1,728) | GBL (192) |
|  | 1-7 | R-35 | P-2 (80) | PAG-A (3.0) | Q-1 (3.5) | SF-1 (3.0) | PGMEA (1,728) | GBL (192) |
|  | 1-8 | R-36 | P-2 (80) | PAG-B (3.0) | Q-1 (3.5) | SF-1 (3.0) | PGMEA (1,728) | GBL (192) |
|  | 1-9 | R-37 | P-2 (80) | PAG-C (7.0) | Q-1 (3.5) | SF-1 (3.0) | PGMEA (1,728) | GBL (192) |
|  | 1-10 | R-38 | P-2 (80) | PAG-D (7.0) | Q-1 (3.5) | SF-1 (3.0) | PGMEA (1,728) | GBL (192) |
|  | 1-11 | R-39 | P-2 (80) | PAG-E (7.0) | Q-1 (3.5) | SF-1 (3.0) | PGMEA (1,728) | GBL (192) |
|  | 1-12 | R-40 | P-2 (80) | PAG-F (7.0) | Q-1 (3.5) | SF-1 (3.0) | PGMEA (1,728) | GBL (192) |

The alkali-soluble surfactant SF-1, comparative photoacid generators PAG-A to PAG-F, quenchers Q-1 to Q-4, and surfactant A in Tables 1 and 2 are identified below.

Alkali-Soluble Surfactant SF-1:
poly(2,2,3,3,4,4,4-heptafluoro-1-isobutyl-1-butyl methacrylate/9-(2,2,2-trifluoro-1-trifluoroethyloxycarbonyl)-4-oxatricyclo[4.2.1.0$^{3,7}$]nonan-5-on-2-yl methacrylate)
Mw=7,700
Mw/Mn=1.82

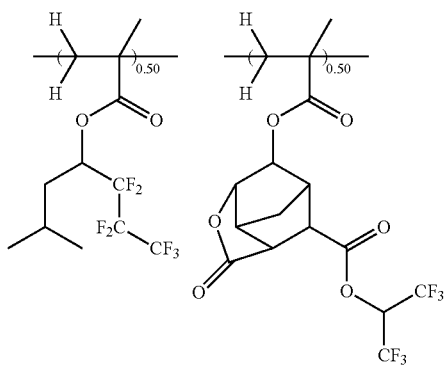

SF-1

Comparative Photoacid Generators PAG-A to PAG-F

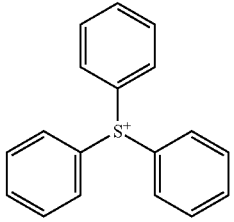

PAG-A

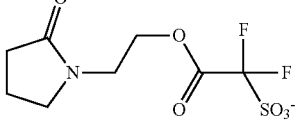

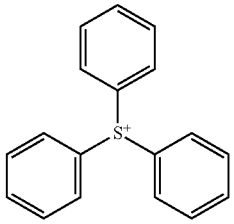

PAG-B

-continued
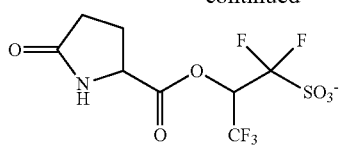
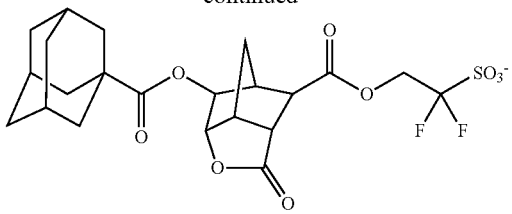
PAG-C
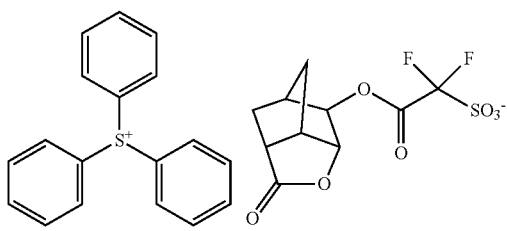
Quenchers Q-1 to Q-4
Q-1
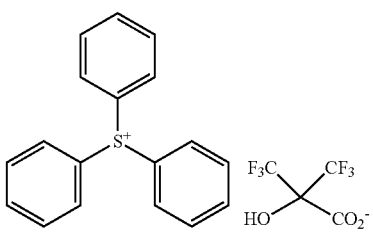
PAG-D
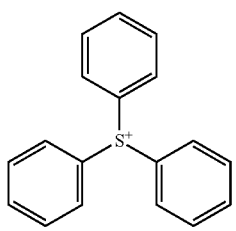
Q-2
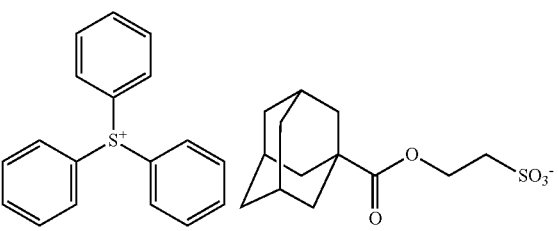
PAG-E
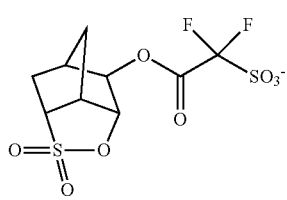
Q-3
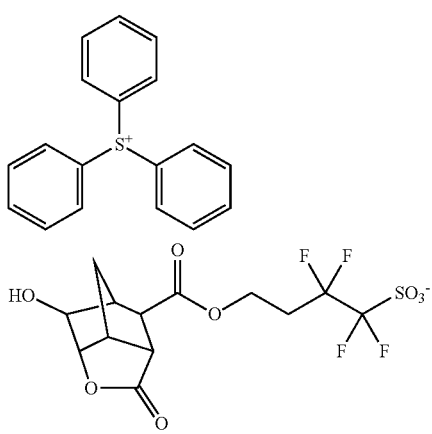
Q-4
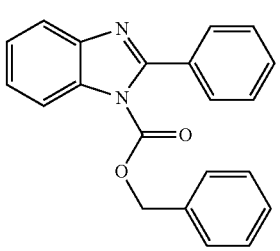
Surfactant A:
3-methyl-3-(2,2,2-trifluoroethoxymethyl)oxetane/tetrahydrofuran/2,2-dimethyl-1,3-propane diol copolymer (Omnova Solutions, Inc.)
PAG-F
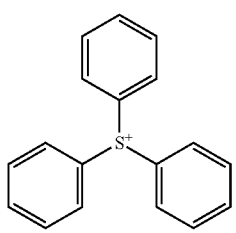
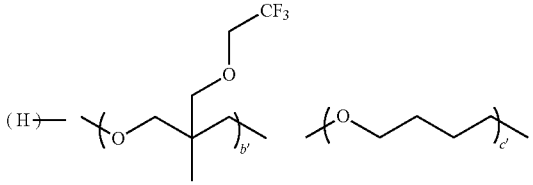

-continued

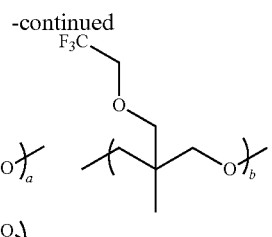

a: (b+b′):(c+c′) = 1:4-7:0.01-1 (molar ratio)
Mw = 1,500

[4] Evaluation of Chemically Amplified Resist Composition: ArF Lithography Patterning Test 1

Examples 3-1 to 3-14 and Comparative Examples 2-1 to 2-6

On a silicon substrate, an antireflective coating solution (ARC29A, Nissan Chemical Corp.) was coated and baked at 200° C. for 60 seconds to form an ARC of 100 nm thick. Each of the resist compositions (R-1 to R-14, R-29 to R-34) was spin coated on the ARC and prebaked on a hotplate at 100° C. for 60 seconds to form a resist film of 90 nm thick on the ARC. The wafer was exposed on an ArF excimer laser immersion lithography scanner (NSR-S610C by Nikon Corp., NA 1.30, dipole illumination) through a Cr mask having a line-and-space pattern with a line width of 40 nm and a pitch of 80 nm (on-wafer size), while varying the exposure dose and focus at a dose pitch of 1 mJ/cm$^2$ and a focus pitch of 0.025 μm. The immersion liquid used herein was water. After exposure, the resist film was baked (PEB) at the temperature shown in Table 3 for 60 seconds. The resist film was puddle developed in a 2.38 wt % tetramethylammonium hydroxide (TMAH) aqueous solution for 30 seconds, rinsed with deionized water and spin dried, forming a positive pattern.

The L/S pattern after development was observed under CD-SEM (CG5000 by Hitachi High-Technologies Corp.), whereupon sensitivity, EL, MEF, LWR, and profile were evaluated by the following methods. The results are shown in Table 3.

Evaluation of Sensitivity

The optimum exposure dose Eop (mJ/cm$^2$) which provided a L/S pattern having a line width of 40 nm and a pitch of 80 nm was determined as an index of sensitivity. A smaller dose value indicates a higher sensitivity.

Evaluation of exposure latitude (EL) The exposure dose which provided a L/S pattern with a space width of 40 nm+10% (i.e., 36 nm to 44 nm) was determined. EL (%) is calculated from the exposure doses according to the following equation:

$$EL\ (\%)=(|E1-E2|/Eop)\times 100$$

wherein E1 is an optimum exposure dose which provides a L/S pattern with a line width of 36 nm and a pitch of 80 nm, E2 is an optimum exposure dose which provides a L/S pattern with a line width of 44 nm and a pitch of 80 nm, and Eop is an optimum exposure dose which provides a L/S pattern with a line width of 40 nm and a pitch of 80 nm.

Evaluation of Mask Error Factor (MEF)

A L/S pattern was formed by exposure in the optimum dose Eop through the mask with the pitch fixed and the line width varied. MEF was calculated from the mask line width and a variation of the pattern line width according to the following equation:

$$MEF=(\text{pattern line width})/(\text{mask line width})-b$$

wherein b is a constant. A value closer to unity (1) indicates better performance.

Evaluation of Line Width Roughness (LWR)

A L/S pattern was formed by exposure in the optimum dose Eop. The line width was measured at longitudinally spaced apart 10 points, from which a 3-fold value (3σ) of standard deviation (a) was determined and reported as LWR. A smaller value of 3σ indicates a pattern having a lower roughness and more uniform line width.

Evaluation of Profile

A cross section of the L/S pattern printed at the optimum dose Eop was observed under SEM (S-4800 by Hitachi High Technologies Corp.). A resist film providing a line pattern of substantially rectangular profile is evaluated "Good". A resist film providing a pattern of rounded profile or T-top profile, i.e., a pattern with overhanging top is evaluated "NG".

TABLE 3

|  |  | Resist composition | PEB temp. (° C.) | Eop (mJ/cm$^2$) | EL (%) | MEF | LWR (nm) | Profile |
|---|---|---|---|---|---|---|---|---|
| Example | 3-1 | R-01 | 100 | 38 | 30 | 2.4 | 2.3 | Good |
|  | 3-2 | R-02 | 100 | 61 | 39 | 2.5 | 2.3 | Good |
|  | 3-3 | R-03 | 100 | 73 | 42 | 2.3 | 2.6 | Good |
|  | 3-4 | R-04 | 100 | 63 | 38 | 2.3 | 2.2 | Good |
|  | 3-5 | R-05 | 95 | 31 | 42 | 2.4 | 2.5 | Good |
|  | 3-6 | R-06 | 100 | 42 | 41 | 2.5 | 2.4 | Good |
|  | 3-7 | R-07 | 95 | 40 | 42 | 2.4 | 2.3 | Good |
|  | 3-8 | R-08 | 95 | 39 | 40 | 2.4 | 2.4 | Good |
|  | 3-9 | R-09 | 100 | 39 | 39 | 2.5 | 2.6 | Good |
|  | 3-10 | R-10 | 100 | 41 | 38 | 2.3 | 2.7 | Good |
|  | 3-11 | R-11 | 95 | 37 | 39 | 2.4 | 2.3 | Good |
|  | 3-12 | R-12 | 100 | 38 | 41 | 2.4 | 2.5 | Good |
|  | 3-13 | R-13 | 95 | 40 | 42 | 2.3 | 2.9 | Good |
|  | 3-14 | R-14 | 95 | 37 | 38 | 2.4 | 2.6 | Good |
|  | 2-1 | R-29 | 100 | 32 | 30 | 3.4 | 3.2 | NG |
|  | 2-2 | R-30 | 100 | 40 | 33 | 3.2 | 3.3 | NG |
|  | 2-3 | R-31 | 100 | 40 | 35 | 3.9 | 3.1 | Good |
| Comparative | 2-4 | R-32 | 100 | 39 | 33 | 3.8 | 3.1 | Good |
| Example | 2-5 | R-33 | 100 | 39 | 35 | 3.3 | 3.3 | NG |
|  | 2-6 | R-34 | 95 | 40 | 34 | 3.2 | 3.8 | NG |

As is evident from Table 3, the resist compositions containing salts within the scope of the invention exhibit a satisfactory sensitivity, improved values of EL, MEF and LWR and form patterns of good profile. The resist compositions are useful as the ArF immersion lithography material.

[5] Evaluation of Chemically Amplified Resist Composition: ArF Lithography Patterning Test 2

Examples 4-1 to 4-14 and Comparative Examples 3-1 to 3-6

On a substrate, a spin-on carbon film ODL-180 (Shin-Etsu Chemical Co., Ltd.) having a carbon content of 80 wt % was deposited to a thickness of 180 nm and a silicon-containing spin-on hard mask SHB-A941 having a silicon content of 43 wt % was deposited thereon to a thickness of 35 nm. On this substrate for trilayer process, each of the resist compositions (R-15 to R-28, R-35 to R-40) was spin coated, then baked on a hot plate at 100° C. for 60 seconds to form a resist film of 100 nm thick.

Using an ArF excimer laser immersion lithography scanner NSR-S610C (Nikon Corp., NA 1.30, σ 0.90/0.72, cross-pole opening 35 deg., cross-pole illumination, azimuthally polarized illumination), exposure was performed through a 6% halftone phase shift mask bearing a contact hole (CH) pattern with a hole size of 45 nm and a pitch of 110 nm (on-wafer size) while varying the dose and focus (dose pitch: 1 mJ/cm$^2$, focus pitch: 0.025 μm). The immersion liquid used herein was water. After the exposure, the substrate was baked (PEB) at the temperature shown in Table 4 for 60 seconds. Thereafter, the resist film was puddle developed in n-butyl acetate for 30 seconds, rinsed with 4-methyl-2-pentanol, and spin dried, obtaining a negative pattern. The CH pattern after development was observed under CD-SEM CG4000 (Hitachi High Technologies Corp.) whereupon sensitivity, MEF, CDU, and DOF were evaluated by the following methods. The results are shown in Table 4.

Evaluation of Sensitivity

The optimum dose Eop (mJ/cm$^2$) which provided a CH pattern with a hole size of 45 nm and a pitch of 110 nm in ArF lithography patterning test 2 was determined as an index of sensitivity. A smaller dose value indicates a higher sensitivity.

Evaluation of MEF

A CH pattern was formed by exposure at the optimum dose Eop by ArF lithography patterning test 2 with the pitch fixed and the mask size varied. MEF was calculated from the mask size and a variation of the CH pattern size according to the following equation:

MEF=(pattern size)/(mask size)−b wherein b is a constant. A value closer to unity (1) indicates better performance.

Evaluation of Critical Dimension Uniformity (CDU)

For the CH pattern formed by exposure at the optimum dose Eop in ArF lithography patterning test 2, the hole size was measured at 10 areas subject to an identical dose of shot (9 contact holes per area), from which a 3-fold value (3a) of standard deviation (a) was determined and reported as CDU. A smaller value of 3a indicates a CH pattern having improved CDU.

Evaluation of Depth of Focus (DOF)

As an index of DOF, a range of focus which provided a CH pattern with a size of 45 nm+10% (i.e., 41 to 49 nm) in ArF lithography patterning test 2 was determined. A greater value indicates a wider DOF.

TABLE 4

| | | Resist composition | PEB temp. (° C.) | Eop (mJ/cm$^2$) | MEF | CDU (nm) | DOF (nm) |
|---|---|---|---|---|---|---|---|
| Example | 4-1 | R-15 | 95 | 40 | 2.4 | 2.9 | 150 |
| | 4-2 | R-16 | 90 | 41 | 2.5 | 2.8 | 140 |
| | 4-3 | R-17 | 90 | 39 | 2.5 | 2.9 | 150 |
| | 4-4 | R-18 | 95 | 40 | 2.4 | 2.7 | 130 |
| | 4-5 | R-19 | 90 | 41 | 2.6 | 2.6 | 140 |
| | 4-6 | R-20 | 90 | 40 | 2.4 | 2.8 | 150 |
| | 4-7 | R-21 | 95 | 40 | 2.5 | 2.9 | 150 |
| | 4-8 | R-22 | 90 | 40 | 2.5 | 2.7 | 140 |
| | 4-9 | R-23 | 95 | 42 | 2.4 | 2.7 | 130 |
| | 4-10 | R-24 | 95 | 38 | 2.6 | 2.9 | 150 |
| | 4-11 | R-25 | 90 | 39 | 2.4 | 2.8 | 140 |
| | 4-12 | R-26 | 95 | 41 | 2.5 | 2.9 | 130 |
| | 4-13 | R-27 | 90 | 40 | 2.6 | 2.7 | 150 |
| | 4-14 | R-28 | 95 | 41 | 2.4 | 2.9 | 150 |
| Comparative Example | 3-1 | R-35 | 90 | 47 | 3.4 | 4.4 | 70 |
| | 3-2 | R-36 | 95 | 44 | 3.3 | 4.5 | 80 |
| | 3-3 | R-37 | 95 | 43 | 3.5 | 3.6 | 80 |
| | 3-4 | R-38 | 95 | 42 | 3.5 | 3.7 | 100 |
| | 3-5 | R-39 | 90 | 42 | 3.4 | 3.5 | 90 |
| | 3-6 | R-40 | 95 | 41 | 2.9 | 3.4 | 100 |

As is evident from Table 4, the resist compositions containing salts within the scope of the invention exhibit a satisfactory sensitivity and improved values of CDU, MEF and DOF in forming negative patterns via organic solvent development. The resist compositions are also useful in the organic solvent development process.

Japanese Patent Application No. 2018-214718 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A salt compound having the formula (A):

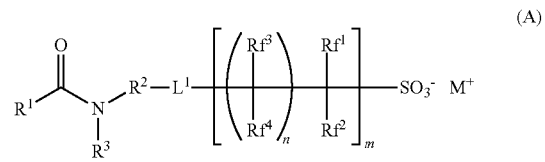

wherein $R^1$ is a $C_1$-$C_{20}$ monovalent hydrocarbon group which may contain a heteroatom, $R^2$ is a $C_1$-$C_{20}$ divalent hydrocarbon group which may contain a heteroatom, $R^3$ is hydrogen or a $C_1$-$C_{12}$ monovalent hydrocarbon group, $R^1$ and $R^3$ may bond together to form a ring with the carbon and nitrogen atoms to which they are attached, $R^{f1}$, $R^{f2}$, $R^{f3}$ and $R^{f4}$ are each independently hydrogen, fluorine or trifluoromethyl, at least one of $R^{f1}$, $R^{f2}$, $R^{f3}$ and $R^{f4}$ is fluorine or trifluoromethyl, $L^1$ is —CO—O—, —O—CO—, —O—CO—O— or —O—, $M^+$ is a monovalent organic cation, m is 1, and n is 1.

2. The salt compound of claim 1 wherein $R^{f1}$ and $R^{f2}$ are fluorine, $R^{f3}$ and $R^{f4}$ are hydrogen.

3. The salt compound of claim 1 wherein $R^{f1}$ and $R^{f2}$ are fluorine, $R^{f3}$ is trifluoromethyl, and $R^{f4}$ is hydrogen.

4. The salt compound of claim 1 wherein $R^1$ is a lactone structure-containing group.

5. The salt compound of claim 1 wherein M⁺ is a sulfonium cation having the formula (A1), an iodonium cation having the formula (A2) or an ammonium cation having the formula (A3):

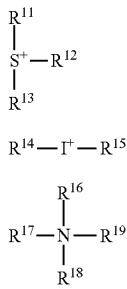

(A1)

(A2)

(A3)

wherein $R^{11}$ to $R^{19}$ are each independently a $C_1$-$C_{20}$ monovalent hydrocarbon group which may contain a heteroatom.

6. A photoacid generator comprising the salt compound of claim 1.

7. A chemically amplified resist composition comprising the photoacid generator of claim 6.

8. The resist composition of claim 7, further comprising a base resin containing a polymer comprising recurring units having the formula (a) and recurring units having the formula (b):

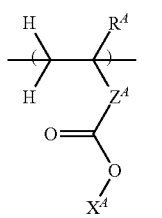

(a)

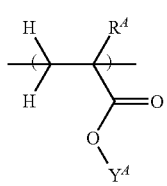

(b)

wherein $R^A$ is each independently hydrogen, fluorine, methyl or trifluoromethyl, $Z^A$ is a single bond, phenylene, naphthylene or (backbone)-C(=O)—O—Z'—, Z' is a $C_1$-$C_{10}$ alkanediyl group which may contain a hydroxyl moiety, ether bond, ester bond or lactone ring, or a phenylene or naphthylene group, $X^A$ is an acid labile group, and $Y^A$ is hydrogen or a polar group containing at least one structure selected from the group consisting of hydroxyl, cyano, carbonyl, carboxyl, ether bond, ester bond, sulfonate bond, carbonate bond, lactone ring, sultone ring and carboxylic anhydride.

9. The resist composition of claim 7, further comprising an organic solvent.

10. The resist composition of claim 7, further comprising a quencher.

11. The resist composition of claim 10 wherein the quencher contains a compound having the formula (1a) or (1b):

(1a)

(1b)

wherein $R^{q1}$ is hydrogen or a $C_1$-$C_{40}$ monovalent hydrocarbon group which may contain a heteroatom, excluding the hydrocarbon group in which the hydrogen atom bonded to the carbon atom at α-position relative to the sulfo group is substituted by fluorine or fluoroalkyl, $R^{q2}$ is hydrogen or a $C_1$-$C_{40}$ monovalent hydrocarbon group which may contain a heteroatom, and Mq⁺ is an onium cation.

12. The resist composition of claim 10 wherein the quencher contains an amine compound.

13. The resist composition of claim 7, further comprising a photoacid generator other than the photoacid generator.

14. The resist composition of claim 13 wherein the other photoacid generator has the formula (3) or (4):

(3)

wherein $R^{101}$, $R^{102}$ and $R^{103}$ are each independently a $C_1$-$C_{20}$ monovalent hydrocarbon group which may contain a heteroatom, any two of $R^{101}$, $R^{102}$ and $R^{103}$ may bond together to form a ring with the sulfur atom to which they are attached, and X⁻ is an anion selected from the following formulae (3A) to (3D):

(3A)

(3B)

(3C)

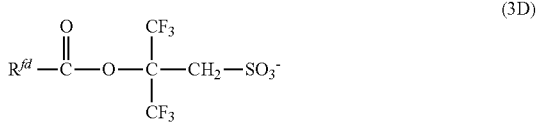

(3D)

wherein $R^{fa}$, $R^{fb1}$, $R^{fb2}$, $R^{fc1}$, $R^{fc2}$ and $R^{fc3}$ are each independently fluorine or a $C_1$-$C_{40}$ monovalent hydrocarbon group which may contain a heteroatom, or a pair of $R^{fb1}$ and $R^{fb2}$, or $R^{fc3}$ and $R^{fc2}$ may bond together to form a ring with the carbon atom to which they are attached and any intervening atoms, $R^{fd}$ is a $C_1$-$C_{40}$ monovalent hydrocarbon group which may contain a heteroatom,

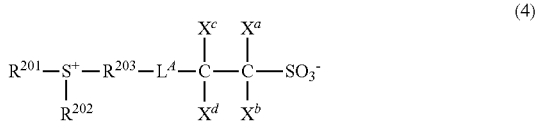

(4)

wherein $R^{201}$ and $R^{202}$ are each independently a $C_1$-$C_{30}$ monovalent hydrocarbon group which may contain a heteroatom, $R^{203}$ is a $C_1$-$C_{30}$ divalent hydrocarbon group which may contain a heteroatom, any two of $R^{201}$, $R^{202}$ and $R^{203}$ may bond together to form a ring with the sulfur atom to which they are attached, $L^A$ is a single bond, ether bond or a $C_1$-$C_{20}$ divalent hydrocarbon group which may contain a heteroatom, $X^a$, $X^b$, $X^c$ and $X^d$ are each independently hydrogen, fluorine or trifluoromethyl, at least one of $X^a$, $X^b$, $X^c$ and $X^d$ is fluorine or trifluoromethyl.

15. The resist composition of claim 7, further comprising a surfactant which is insoluble or substantially insoluble in water and soluble in alkaline developer, and/or a surfactant which is insoluble or substantially insoluble in water and alkaline developer.

16. A pattern forming process comprising the steps of applying the chemically amplified resist composition of claim 7 onto a substrate to form a resist film thereon, exposing a selected region of the resist film to KrF excimer laser, ArF excimer laser, EB or EUV, and developing the exposed resist film in a developer.

17. The pattern forming process of claim 16 wherein the developing step uses an alkaline aqueous solution as the developer, thereby forming a positive pattern in which an exposed region of the resist film is dissolved away and an unexposed region of the resist film is not dissolved.

18. The pattern forming process of claim 16 wherein the developing step uses an organic solvent as the developer, thereby forming a negative pattern in which an unexposed region of the resist film is dissolved away and an exposed region of the resist film is not dissolved.

19. The pattern forming process of claim 18 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

20. The process of claim 16 wherein the exposure step is carried out by immersion lithography while a liquid having a refractive index of at least 1.0 is held between the resist film and a projection lens.

21. The process of claim 20, further comprising the step of forming a protective film on the resist film prior to the exposure step, wherein immersion lithography is carried out while the liquid is held between the protective film and the projection lens.

* * * * *